(12) United States Patent
Jessell et al.

(10) Patent No.: US 7,632,679 B2
(45) Date of Patent: Dec. 15, 2009

(54) SYSTEMS AND METHODS FOR SCREENING FOR MODULATORS OF NEURAL DIFFERENTIATION

(75) Inventors: Thomas Jessell, Bronx, NY (US); Hynek Wichterle, New York, NY (US); Sara Wilson, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 183 days.

(21) Appl. No.: 10/789,308

(22) Filed: Feb. 26, 2004

(65) Prior Publication Data

US 2004/0224887 A1 Nov. 11, 2004

Related U.S. Application Data

(63) Continuation-in-part of application No. 10/196,882, filed on Jul. 16, 2002.

(51) Int. Cl.
*C12N 5/00* (2006.01)
*C12N 5/02* (2006.01)

(52) U.S. Cl. .................... 435/377; 435/325; 435/368

(58) Field of Classification Search .................. None
See application file for complete search history.

(56) References Cited

U.S. PATENT DOCUMENTS

| | | |
|---|---|---|
| 5,753,506 A | 5/1998 | Johe |
| 5,817,773 A | 10/1998 | Wilson et al. |
| 5,844,079 A * | 12/1998 | Ingham et al. ............... 530/350 |
| 5,851,832 A | 12/1998 | Weiss et al. |
| 5,980,885 A | 11/1999 | Weiss et al. |
| 6,040,180 A | 3/2000 | Johe |
| 6,277,820 B1 | 8/2001 | Rosenthal et al. |
| 6,294,346 B1 | 9/2001 | Weiss et al. |
| 6,432,711 B1 | 8/2002 | Dinsmore et al. |
| 6,552,016 B1 | 4/2003 | Baxter et al. |
| 6,613,798 B1 | 9/2003 | Porter et al. |
| 6,646,113 B1 | 11/2003 | Dreyfuss et al. |
| 6,683,108 B1 | 1/2004 | Baxter et al. |
| 6,683,192 B2 | 1/2004 | Baxter et al. |
| 6,833,269 B2 * | 12/2004 | Carpenter .................... 435/377 |
| 7,115,653 B2 | 10/2006 | Baxter et al. |
| 7,250,294 B2 | 7/2007 | Carpenter et al. |
| 7,390,659 B2 | 6/2008 | Jessell et al. |
| 2002/0009743 A1 | 1/2002 | Carpenter |
| 2002/0151056 A1 * | 10/2002 | Sasai et al. .................. 435/368 |
| 2003/0068819 A1 | 4/2003 | Zhang et al. |
| 2004/0023949 A1 | 2/2004 | Baxter et al. |
| 2004/0092012 A1 * | 5/2004 | Okano et al. ................. 435/366 |
| 2004/0224302 A1 | 11/2004 | Jessel et al. |
| 2005/0014796 A1 | 1/2005 | Baxter et al. |
| 2005/0019801 A1 | 1/2005 | Rubin et al. |
| 2005/0080138 A1 | 4/2005 | Guicherit et al. |
| 2005/0203014 A1 | 9/2005 | Rubin |
| 2005/0266555 A1 | 12/2005 | Lu et al. |
| 2007/0185024 A1 | 8/2007 | Jessell et al. |
| 2007/0224650 A1 | 9/2007 | Jessell et al. |

FOREIGN PATENT DOCUMENTS

| | | |
|---|---|---|
| WO | WO01/174344 | 10/2001 |
| WO | WO2004/007665 | 1/2004 |
| WO | WO2005/021720 | 3/2005 |
| WO | WO2005/081857 | 9/2005 |
| WO | WO2005/082002 | 9/2005 |

OTHER PUBLICATIONS

Abbondanzo et al., Derivation of embryonic stem cell lines. Methods Enzymol., 225: 803-823, 1993.
Akhurst and Derynck, TGF-beta signaling in cancer-a double-edged sword. Trends Cell Biol., 11(11): S44-51, 2001.
Alvarez-Buylla et al., A unified hypothesis on the lineage of neural stem cells. Nat. Rev. Neurosci., 2: 287-293, 2001.
Arber et al., Requirement for the homeobox gene Hb9 in the consolidation of motor neuron identity. Neuron, 23: 659-764, 1999.
Bain et al., Embryonic stem cells express neuronal properties in vitro. Dev. Biol., 168: 342-357, 1995.
Bak et al., The Hedgehog signaling pathway—implications for drug targets in cancer and neurodegenerative disorders. Pharmacogenomics, 4(4): 411-429, 2003.
Beers and Berkow, eds., The Merck Manual of Diagnosis and Therapy, 17th ed. Whitehouse Station, NJ: Merck Research Laboratories, 1999, chap. 183.
Belting et al., Multiple phases of expression and regulation of mouse Hoxc8 during early embryogenesis. J.Exp. Zool., 282: 196-222, 1998.
Bieri et al., Abnormal nerve conduction studies in mice expressing a mutant form of the POU transcription factor, SCIP. J. Neurosci. Res., 50:821-828, 1997.
Bloch-Gallego et al., Survival in vitro of motoneurons identified or purified by novel antibody-based methods is selectively enhanced by muscle-derived factors. Development, 111: 221-232, 1991.
Blumberg et al., An essential role for retinoid signaling in anteroposterior neural patterning. Development, 124: 373-379, 1997.
Botchkarev, V.A., Bone morphogenetic proteins and their antagonists in skin and hair follicle biology. Journal of Investigative Dermatology, 120: 36-47, 2003.

(Continued)

*Primary Examiner*—Daniel C Gamett
(74) *Attorney, Agent, or Firm*—John P. White; Cooper & Dunham LLP

(57) ABSTRACT

The present invention provides in vitro systems for use in identifying modulators of neural differentiation. Also provided are modulators identified by these systems. The present invention further provides methods for identifying a modulator of neural differentiation, a modulator of a Wnt signalling pathway, a modulator of Wnt-dependent neural differentiation, a modulator of a BMP signalling pathway, a modulator of BMP-dependent neural differentiation, a modulator of a Hh signalling pathway, and a modulator of Hh-dependent neural differentiation. Also provided are modulators identified by these methods.

7 Claims, 16 Drawing Sheets

OTHER PUBLICATIONS

Brazelton et al., From marrow to brain: expression of neuronal phenotypes in adult mice. Science, 290: 1775-1779, 2000.

Briscoe and Ericson, Specification of neuronal fates in the ventral neural tube. Curr. Opin. Neurobiol., 11:43-49, 2001.

Briscoe et al., A homeodomain protein code specifies progenitor cell identity and neuronal fate in the ventral neural tube. Cell, 101: 435-445, 2000.

Byrd et al., Hedgehog is required for murine yolk sac angiogenesis. Development, 129: 361-372, 2002.

Cadigan and Nusse, Wnt signaling: a common theme in animal development. Genes Dev., 11(24): 3286-3305, 1997.

Camu et al., Purification of embryonic rat motoneurons by panning on a monoclonal antibody to the low-affinity NGF receptor. J. Neurosci. Methods, 44: 59-70, 1992.

Chambon, P., The molecular and genetic dissection of the retinoid signaling pathway. Recent Prog. Horm. Res., 50: 317-332, 1995.

Chambon, P., The retionoid signaling pathway: molecular and genetic analysis. Semin. Cell Biol., 5(2): 115-125, 1994.

Chiang et al., Cyclopia and defective axial patterning in mice lacking Sonic hedgehog gene function. Nature, 383: 407-413, 1996.

Chiba et al., Distinct retinoid X receptor—retinoic acid receptor heterodimers are differentially involved in the control of expression of of retinoid target genes in F9 embryonal carcinoma cells. Mol. Cell Biol., 17: 3013-3020, 1997.

Choi et al., A generic intron increases gene expression in transgenic mice. Mol. Cell Biol., 11: 3070-3074, 1991.

Cross and Claesson-Welsh, FGF and VEGF function in angiogenesis: signaling pathways, biological responses and therapeutic inhibition. Trends Pharmacol. Sci., 22(4): 201-207, 2001.

Danielsen and Maihle, The EGF/ErbB receptor family and apoptosis. Growth Factors, 20(1): 1-15, 2002.

Davis and Joyner, Expression patterns of the homeobox-containing genes En-1 and En-2 and the proto-oncogene int-1 diverge during mouse development. Genes Dev., 2: 1736-1744, 1988.

Durston et al., Retinoids and related signals in early development of the vertebrate central nervous system. Curr. Top Dev. Biol., 40: 111-175, 1998.

Dyer et al., Indian hedgehog activities hematopoiesis and vasculogenesis and can respecify prospective neurectomdermal cell fate in the mouse embryo. Development, 128: 1717-1730, 2001.

Ericson et al., Pax6 controls progenitor cell identity and neuronal fate in response to graded SHh signaling. Cell, 90: 169-180, 1997.

Ericson et al., Two critical periods of Sonic Hedgehog signaling required for the specification of motor neuron identity. Cell, 87: 661-673, 1996.

Falls, D.L., Neuregulins: functions, forms, and signaling strategies. Exp. Cell Res., 284(1) 14-30, 2003.

Frank-Kamenetsky et al., Small-molecule modulators of Hedgehog signaling: Identification and characterization of Smoothened agonists and antagonists. J. Biol. 1(2): 10, 2002.

Gage, F. H., Mammalian neural stem cells. Science, 287: 1433-1438, 2000.

Giles et al., Caught up in a Wnt storm: Wnt signaling in cancer. Biochim. Biophys. Acta., 1653(1): 1-24, 2003.

Goodwin and D'Amore, Wnt signaling in the vasculature. Angiogenesis, 5(1-2): 1-9, 2002.

Gratsch et al., Noggin and chordin have distinct activities in promoting lineage commitment of mouse embryonic stem (ES) cells. Dev. Biol., 245: 83-94, 2002.

Hatsell et al., Beta-catenin and Tcfs in mammary development and cancer. J. Mammary Gland Biol. Neoplasia., 8:145-158, 2003.

Hollyday et al., An autoradiographic study of the formation of the lateral motor column in the chick embryo. Brain Res., 132: 197-208, 1977.

Hsieh et al., Biochemical characterization of Wnt-frizzled interactions using a soluble, biologically active vertebrate Wnt protein. Proc. Natl. Acad. Sci. USA, 96: 3546-3551, 1999.

Imondi and Thomas, Neuroscience: the ups and downs of Wnt signaling. Science, 302: 1903-1904, 2003.

Lee et al., The specification of dorsal cell fates in the vertebrate central nervous system. Annu. Rev. Neurosci., 22: 261-294, 1999.

Lemaire and Kessel, Gastrulation and homeobox genes in chick embryos. Mech. Dev., 67: 3-16, 1997.

Jessell et al., Neuronal specification in the spinal cord: inductive signals and transcriptional codes. Nat. Rev. Genet., 1: 20-29, 2000.

Kalderon, D., Hedgehog signaling: Costal-2 bridges the transduction gap. Curr. Biol., 14(2): R67-69, 2004.

Kania et al., Coordinate roles for LIM homeobox genes in directing the dorsoventral trajectory of motor axons in the vertebrate limb. Cell, 102: 161-173, 2000.

Katoh, M., Genome-wide search of human genes implicated in Wnt signaling pathway using bioinformatics. Genome Informatics, 13:367-368, 2002.

Kawasaki et al., Induction of midbrain dopaminergic neurons from ES cells by stromal cell-dervied inducing activity. Neuron, 28: 31-40, 2000.

Kyba et al., HoxB4 confers definitive lymphoid-myeloid engraftment potential on embryonic stem cell and yolk sac hematopoietic progenitors. Cell, 109: 29-37, 2002.

Lauta, V. M., A review of the cytokine network in multiple myeloma: diagnostic, prognostic, and therapeutic implications. Cancer, 97(10): 2440-2452, 2003.

Lee et al., Transcriptional networks regulating neuronal identity in the developing spinal cord. Nat. Neurosci., 4 Suppl. : 1183-1191, 2001.

Lee et al., Efficient generation of midbrain and hindbrain neurons from mouse embryonic stem cells. Nat. Biotechnol., 18: 675-679, 2000.

Liu et al., Assigning the positional identity of spinal motor neurons. Rostrocaudal patterning of Hox-c expression by FGFs, Gdf11, and retinoids. Neuron, 32: 997-1012, 2001.

Lu et al., Common developmental requirement for Olig function indicates a motor neuron/oligodendrocyte connection. Cell, 109: 75-86, 2002.

Malbon et al., Wnt signaling and heterotrimeric G-proteins: strange bedfellows or a classic romance? Biochem. Biophys. Res. Commun., 287(3): 589-593, 2001.

Mallamaci et al., OTX2 homeoprotein in the developing central nervous system and migratory cells of the olfactory area. Mech. Dev., 58: 165-178, 1996.

Massague et al., TGFbeta signaling in growth control, cancer, and heritable disorders. Cell, 103: 295-309, 2000.

McMahon, A. P., More surprises in the hedgehog signaling pathway. Cell, 100: 185-188, 2000.

Mezey et al., Turning blood into brain: cells bearing neuronal antigens generated in vivo from bone marrow. Science, 290: 1779-1782, 2000.

Miyazono et al., Divergence and convergence of TGF-beta/BMP signaling. J. Cell Physiol., 187(3): 265-276, 2001.

Miyazono, K., Positive and negative regulation of TGF-beta signaling. J. Cell Sci., 113(7): 1101-1109, 2000.

Mizuguchi et al., Combinatorial roles of olig2 and neurogenin2 in the coordinated induction of pan-neuronal and subtype-specific properties of motoneurons. Neuron, 31: 757-771, 2001.

Moon et al., The promise and perils of Wnt signaling through beta-catenin. Science, 296(5573): 1644-1646, 2002.

Muhr et al., Convergent inductive signals specify midbrain, hindbrain, and spinal cord identity in gastrula stage chick embryos. Neuron, 23: 689-702, 1999.

Munoz-Sanjuan et al., Neural induction, the default model and embryonic stem cells. Nat. Rev. Neurosci., 3: 271-280, 2002.

Nordstrom et al., Progressive induction of caudal neural character by graded Wnt signaling. Nat. Neurosci., 5(6): 525-532, 2002.

Novitch et al., Coordinate regulation of motor neuron subtype identity and pan-neuronal properties by the bHLH repressor Olig2. Neuron, 31:773-789, 2001.

Nusse, R., Wnts and hedgehogs: lipid-modified proteins and similarities in signaling mechanisms at the cell surface. Development, 130(22): 5297-5305, 2003.

O'Brien et al., Development and survival of thoracic motonerons and hindlimb musculature following transplantation of the thoracic neural tube to the lumbar region in the chick embryo: anatomical aspects. J. Neurobiol., 21:313-340, 1990.

Ornitz and Itoh, Fibroblast growth factors. Genome. Biol., 2(3): Reviews3005, 2001.
Pandur et al., Increasingly complex: new players enter the Wnt signaling network. Bioessays, 24(10): 881-884, 2002.
Pattyn et al., Control of hindbrain motor neuron differentiation by the homeobox gene Phox2b. Development, 127: 1349-1358, 2000.
Pevny et al., Generation of purified neural precursors from embryonic stem cells by lineage selection. Curr. Biol., 8: 971-974, 1998.
Pfaff et al., Requirement for LIM homeobox gene Isl1 in motor neuron generation reveals a motor neuron-dependent step in interneuron differentiation. Cell, 84: 309-320, 1996.
Pierani et al., Control of interneuron fate in the developing spinal cord by the progenitor homeodomain protein Dbx1. Neuron, 29(2): 367-384, 2001.
Postigo, A.A., Opposing functions of ZEB proteins in the regulation of the TGF/BMP signaling pathway. EMBO J., 22: 2443-2452, 2003.
Povelones and Nusse, Wnt signaling sees spots. Nat. Cell Biol., 4(11): E249-250, 2002.
Raju et al., SANE, a novel lem domain protein, regulates bone morphogenetic protein signaling through interaction with smad1. J. Biol. Chem., 278(1): 428-437, 2003.
Rathjen et al., Directed differentiation of pluripotent cells to neural lineages: homogenous formation and differentiation of a neurectoderm population. Development, 129: 2649-2661, 2002.
Renoncourt et al., Neurons derived in vitro from ES cells express homeoproteins characteristic of motoneurons and interneurons. Mech. Dev., 79: 185-197, 1998.
Reubinoff et al., Nueral progenitors from human embryonic stem cells. Nat. Biotechnol., 19: 1134-1140, 2001.
Ring and Cho, Specificity in transforming growth factor-beta signaling pathways. Am. J. Hum. Genet., 64: 691-697, 1999.
Roelink et al., Floor plate and motor neuron induction by different concentrations of the amino-terminal cleavage product of sonic hedgehog auto proteolysis. Cell, 81: 445-455, 1995.
Sander et al., Ventral neural patterning by Nkx homeobox genes: Nkx6.1 controls somatic motor neuron and ventral interneuron fates. Genes Dev., 14: 2134-2139, 2000.
Schuldine et al., Induced neuronal differentiation of human embryonic stem cells. Brain Res., 913: 201-205, 2001.
Sharma et al., Genetic and epigenetic mechanisms contribute to motor neuron pathfinding. Nature, 406: 515-519, 2000.
Sharma et al., LIM homeodomain factors Lhx3 and Lhx5 assign subtype identities for motor neurons. Cell, 95: 817-828, 1998.
Shibamoto et al., Cytoskeletal reorganization by soluble Wnt-3a protein signaling. Genes Cells, 3: 659-670, 1998.
Streit et al., Initiation of neural induction by FGF signaling before gastrulation. Nature, 406: 74-78, 2000.
Tanabe et al., Specification of motor neuron identity by the MNR2 homeodomain protein. Cell, 95: 67-80, 1998.
Temple, S., The development of neural stem cells. Nature, 414:112-117, 2001.
Terada et al., Bone marrow cells adopt the phenotype of other cells by spontaneous cell fusion. Nature, 416: 542-545, 2002.
Thaler et al., Active suppression of interneuron programs within developing motor neurons revealed by analysis of homeodomain factor HB9. Neuron, 23: 675-687, 1999.
Tropepe et al., Direct neural fate specification from embryonic stem cells: a primitive mammalian neural stem cell stage acquired through a default mechanism. Neuron, 30: 65-78, 2001.
Tsuchida et al., Topographic organization of embryonic motor neurons defined by expression of LIM homeobox genes. Cell, 79: 957-970, 1994.
Uchida et al., Direct isolation of human central nervous system stem cells. Proc. Natl. Acad. Sci. USA, 97: 14720-14725, 2000.
Vallstedt et al., Different levels of repressor activity assign redundant and specific roles to NKx6 genes in motor neuron and interneuron specification. Neuron, 31: 743-755, 2001.
Van Es et al., You Wnt some, you lose some: oncogenes in the Wnt signaling pathway. Curr. Opin. Genet. Dev., 13(1): 28-33, 2003.
Van Gijn et al., The Wnt-frizzled cascade in cardovascular disease. Cardiovasc. Res., 1: 16-24, 2002.
Veeman et al., A second canon: functions and mechanisms of beta-catenin-independent Wnt signaling. Dev. Cell 5(3): 367-377, 2003.
Waxman and Bennett, Relative conduction velocities of small myelinated and nonmyelinated fibres in the central nervous system. Nature New Biol., 238:217, 1972.
Weston et al., Revisiting the role of retinoid signaling in skeletal development. Birth Defects Res. Part C Embryo Today, 69(2): 156-173, 2003.
Wetmore, C., Sonic hedgehog in normal and neoplastic proliferation: insight gained from human tumors and animal models. Curr. Opin. Genet. Dev., 13(1): 34-42, 2003.
Wilson et al., Neural induction: toward a unifying mechanism. Nat. Neurosci., 4th Suppl.: 1161-1168, 2001.
Wilson et al., An early requirement for FGF signaling in the acquisition of neural cell fate in the chick embryo. Curr. Biol., 10: 421-429, 2000.
Wilson et al., The status of Wnt signaling regulates neural and epidermal fates in the chick embryo. Nature, 411: 325-330, 2001.
Wodarz and Nusse, Mechanisms of Wnt signaling in development. Annu. Rev. Cell Dev. Biol., 14: 59-88, 1998.
Wood et al., Comparative expression of the mouse Sox1, Sox2 and Sox3 genes from pre-gastrulation to early somite stages. Mech. Dev., 86: 197-201, 1999.
Wrana, J., Regulation of Smad activity. Cell, 100: 189-192, 2000.
Xian et al., Peering in to early neurogenesis with embyronic stem cells. Trends Neurosci., 24: 685-686, 2001.
Yamada et al., Control of cell pattern in the developing nervous system: polarizing activity of the floor plate and notochord. Cell, 64: 635-647, 1991.
Yamaguchi et al., XIAP, a cellular member of the inhibitor of apoptosis protein family, links the receptors to TAB1-TAK1 in the BMP signaling pathway. EMBO J., 18(1): 179-187, 1999.
Ying et al., Changing potency by spontaneous fusion. Nature, 416: 545-548, 2002.
Yu et al., Platelet-derived growth factor signaling and human cancer. J. Biochem. Mol. Biol., 36(1): 49-59, 2003.
Zhang et al., In vitro differentiation of transplantable neural precursors from human embryonic stem cells. Nat. Biotechnol., 19: 1129-1133, 2001.
Zhou et al., The bHLH transcription factors OLIG2 and OLIG1 couple neruonal and glial subtype specification. Cell, 109: 61-73, 2002.
Ericson, et al., 1996, "Two critical periods of Sonic Hedgehog signaling required for the specification of motor neuron identity," Cell. Nov. 15;87(4):661-73.
Gross, et al., 1996, "Bone morphogenetic proteins promote astroglial lineage commitment by mammalian subventricular zone progenitor cells," Neuron 17(4):595-606.
Lillien, et al., 2000, "BMP and FGF regulate development of EGF-responsive neural progenitor cells," Development, 127(22):4993-5005.
Carpenter, et al., 2001, "Enrichment of neurons and neural precursors from human embryonic stem cells," Experimental Neurology, 172(2):383-397.
Frank-Kamenetsky, et al., 2002, "Small-molecule modulators of Hedgehog signaling: identification and characterization of Smoothened agonists and antagonists," J Biol. 1(2):10.
Wichterle, et al. 2002, "Directed differentiation of embryonic stem cells into motor neurons," Cell. 2002 110(3):385-97.
Howard Huges Medical Institute, Jul. 2002, "Researchers produce motor neurons from embryonic stem cells," Scienceblog.com; http://www.scienceblog.com/community.
Howard Hughes Medical Institute Research News, Jul. 2002, "Researchers produce motor neurons from embryonic stem cells," HHMI News.
Novitch, et al. 2003, "A requirement for retinoic acid-mediated transcriptional activation in ventral neural patterning and motor neuron specification," Neuron. 25; 40(1):81-95.
Shin, et al., 2005, "Human Motor Neuron Differentiation from Human Embryonic Stem Cells," Stem Cells and Development, (14): 266-269.
Li, et al., 2005, "Specification of motoneurons from human embryonic stem cells," Nat Biotechnol.23(2):215-21.

ALS, 2005, "Details discovered on How Human Stem Cells become Nerve Cells in Research Funded By The ALS Association; Findings Suggest Routes to New Therapies for Lou Gehrig's Disease," Business Wire.

Lim, et al., 2006, "Derivation of Motor Neurons from three Clonal Human Embryonic Stem Cell Lines" Curr Neurovasc Res. 3(4):281-8.

Alex S. Kiselyov, 2006 Targeting the Hedgehog Signaling Pathway with Small Molecules, Anti-Cancer Agents in Medicinal Chemistry, 6, 445-449.

Deshpande, et al., 2006 "Recovery from paralysis in adult rats using embryonic stem cells" Annals of Neurology, vol. 60, 1 ,32-44.

Soundararajan, et al. 2007, "Easy and Rapid Differentiation of Embryonic Stem Cells into Functional Motoneurons Using Sonic Hedgehog Producing Cells," Stemm Cells 25(7) 1697-1707.

Arnold et al., "Construction of a Plasmid Containing Human SMN, the SMA Determining Gene, Coupled to EGFP." Plasmid, 47(2): 79-87, 2002.

Bjorklund et al., "Embryonic stem cells develop into functional dopaminergic neurons . . . in a Parkinson rat model." Proc Natl Acad Sci USA, 99: 2344-2349, 2002.

Briscoe et al., "Homeobox gene Nkx2.2 and specification of neuronal identity by graded Sonic hedgehog signaling." Nature, 398: 622-627, 1999.

Chung et al., "Deubiquitinating enzymes: their diversity and emerging roles." Biochem Biophys Res Commun., 266:633-640, 1999.

Clontech, "New Living ColorsTM GFP Mammalian Vectors", CLONTECHniques, Jul. 1996.

Corse et al., "Preclinical Testing of Neuroprotective Neurotrophic Factors in a Model of Chronic Motor Neuron Degeneration." Neurobiology of Disease, 58(7): 335-346, 1999.

Derby et al., "GDNF is trophic for mouse motoneurons that express a mutant superoxide dismutase (SOD-1) gene." ALS and Other Motor Neuron Disorders, I(2): 113-122, 2000.

Fraichard et al., "In vitro differentiation of embryonic stem cells into glial cells and functional neurons." J. Cell Sci., 108: 3181-3188, 1995.

Geisert et al., "The neuronal response to injury as visualized by immunostaining of class IL-I beta-tubulin in the rat." Neurosci Lett., 102: 137-141, 1989.

Ghosh et al., "Distinct roles for bFGF and NT-3 in the regulation of cortical neurogenesis." Neuron, 15(1): 89-103, 1995.

Goueli et al., "A novel and simple method to assay the activity of individual protein kinase in crude tissue extracts." Anal Biochem, 225(10):10-17, 1995.

Hsieh-Li et al., "A mouse model for spinal muscular atrophy." Nat Genet., 24: 66-70, 2000.

Hynes et al., "Specification of dopaminergic and serotonergic neurons in the vertebrate CNS." Review. Curr. Opin. Neurobiol., 9: 26-36, 1999.

Lee and Jessell, "The specification of dorsal cell fates in the vertebrate central nervous system." Annu. Rev. Neurosci. 22: 261-294, 1999.

Jessell et al., "The decade of the developing brain." Curr. Opin. Neurobiol., 10:599-611, 2001.

Kawasaki et al., "Induction of midbrain dopaminergic neurons from ES cells by stromal cell-derived inducing activity." Neuron, 28: 31-40, 2000.

Lee et al., BIOSIS Accession No. 2004:197764, Abstract from the Meeting of the Society for Neurocience, Nov. 8-12, 2003.

Lee et al., BIOSIS Accession No. 200400198323, "Motoneuronal differentiation of human ES cells." Abstract from the Meeting of the Society for Neurocience, Nov. 8-12, 2003.

Li et al., "Generation of purified neuronal precursors from embryonic stem cells by lineage selection." Curr Biol., 8:971-974, 1998.

Marquardt et al., "Cracking the transcriptional code for cell specification in the neural tube." Cell, 106: 651-654, 2001.

Mettling et al., Survival of newly postmitotic motoneurons is independent of exogenous trophic support.: J Neurosci.15(4):3128-3137, 1995.

Monani et al., "Animal models of spinal muscular atrophy." Review. Hum Mol Genet., 9(16): 2451-2457, 2000.

Muhr et al., "Assignment of early caudal identity to neural plate cells by a signal from caudal paraxial mesoderm." Neuron, 19: 487-502, 1997.

Mullen et al., "NeuN, a neuronal specific nuclear protein in vertebrates." Development, 116: 201-211, 1992.

Nagai et al., "Rats expressing human cytosolic copperzinc superoxide dismutase transgenes . . . develop motor neuron disease." J. Neurosci., 21: 9246-9254, 2001.

Nicholson et al., "Mice, the motor system, and human motor neuron pathology." Review. Mamm Genome, 11: 1041-1052, 2000.

Pevny et al., "A role for SOX1 in neural determination." Development, 125: 1967-1978, 1998.

Simeoni et al., "Motoneuronal cell death . . . androgen receptors containing an elongated polyglutamine tract." Human Molecular Genetics, 9(1): 133-144, 2000.

Sockanathan et al., "Motor neuron-derived retinoid signalling specifies the subtype identity of spinal motor neurons." Cell, 94: 503-514, 1998.

Spinella-Jaegle et al., "Sonic hedgehog . . . pluripotent mesenchymal cells . . . osteoblastic lineage . . . adipocytic differentiation."J Cell Sci., 114: 2085-2094, 2001.

Talbot et al., "Characterization of a gene encoding Survival Motor Neuron (Smn)-related protein . . . spliceosome complex."Human Molecular Genetics, 7(13): 2149-2156, 1998.

Turgeon et al., "Prevention of Thrombin-Induced Motoneuron Degeneration with Different Neurotrophic Factors in Highly Enriched Cultures." J Neurobiol., 38(4): 571-580, 1999.

Vallier et al., "An efficient system for conditional gene expression in embryonic stem cells . . . differentiated derivatives." Proc Natl Acad Sci USA, 98: 2467-2472, 2001.

Weinstein et al., "Neural induction." Annu Rev Cell Dev Biol., 15: 411-433. 1999.

Westmoreland et al., "Neuronal development of embryonic stem cells: a model of GABAergic neuron differentiation." Biochem Biophys Res Commun., 284: 674-680, 2001.

Zhu et al., "Sonic hedgehog and BMP2 exert opposing actions on proliferation and differentiation of embryonic neural progenitor cells." Dev Biol., 215(1): 118-129, 1999.

The American Heritage Dictionary of the English Language. 4th Ed. (2000). Term: "Motoneuron".

Office Action issued by the United States Patent and Trademark Office on Jul. 19, 2004 in connection with U.S. Appl. No. 10/196,882.

Office Action issued by the United States Patent and Trademark Office on Oct. 1, 2004 in connection with U.S. Appl. No. 10/196,882.

Office Action issued by the United States Patent and Trademark Office on May 3, 2005 in connection with U.S.A. Appl. No. 10/196,882.

Office Action issued by the United States Patent and Trademark Office on Feb. 22, 2006 in connection with U.S. Appl. No. 10/196,882.

Office Action issued by the United States Patent and Trademark Office on Aug. 14, 2006 in connection with U.S. Appl. No. 10/789,266.

Final Office Action issued by the United States Patent and Trademark Office on Oct. 27, 2006 in connection with U.S. Appl. No. 10/196,882.

Office Action issued by the United States Patent and Trademark Office on Apr. 30, 2007 in connection with U.S. Appl. No. 10/789,266.

Office action issued by the United States Patent and Trademark Office on Jun. 22, 2007 in connection with U.S. Appl. No. 10/196,882.

Office Action issued by the United States Patent and Trademark Office on Apr. 30, 2008 in connection with U.S. Appl. No. 11/510,038.

Office Action issued by the United States Patent and Trademark Office on May 9, 2008 in connection with U.S. Appl. No. 11/510,366.

Office Action issued by the United States Patent and Trademark Office on Dec. 12, 2008 in connection with U.S. Appl. No. 11/510,038.

Office Action issued by the United States Patent and Trademark Office on Dec. 17, 2008 in connection with U.S. Appl. No. 11/510,366.

PCT International Preliminary Examination Report issued Apr. 4, 2005, in connection with PCT/US2003/20399, filed Jun. 26, 2003.

PCT International Search Report issued Oct. 7, 2004 in connection with PCT/US2003/20399, filed Jun. 26, 2003.

Written Opinion of International Searching Authority issued Jun. 14, 2007 in connection with PCT/US2005/05166, filed Feb. 18, 2005.

PCT International Search Report issued Jun. 14, 2007 in connection with PCT/US2005/05166, filed Feb. 18, 2005.

PCT International Preliminary Report on Patentability issued Jul. 10, 2007 in connection with PCT/US2005/05166, filed Feb. 18, 2005.

Written Opinion of International Searching Authority issued Jun. 26, 2007 in connection with PCT/US2005/005877, filed Feb. 22, 2005.

PCT International Search Report issued Jun. 26, 2007 in connection with PCT/US2005/005877, filed Feb. 22, 2005.

PCT International Preliminary Report on Patentability issued Jul. 17, 2007 in connection with PCT/US2005/005877, filed Feb. 22, 2005.

Castelo-Branco et al., (2003) "Differential regulation of midbrain dopaminergic neruon development by Wnt-1, Wnt-3a, and Wnt-5a" PNAS, 100(22): 12747-12752.

Dann et al., (2001) "Insights into Wnt binding and signaling from the structures of two Frizzeled cysteine-rich domains" Nature, 412: 86-90.

Muryoama et al., (2004) "Wnt proteins promote neuronal differentiation in neural stem cell culture" Biochemical and Biophysical Research Communications, 313: 915-921.

Supplementary European Search Report issued Jun. 19, 2009 in connection with European Patent Application No. 05723654.9-2406.

* cited by examiner

SYSTEMS AND METHODS FOR SCREENING FOR MODULATORS OF NEURAL DIFFERENTIATION

RELATED APPLICATION

This application is a continuation-in-part of U.S. patent application Ser. No. 10/196,882, filed on Jul. 16, 2002.

BACKGROUND OF THE INVENTION

Hundreds of distinct neuronal types are generated during the development of the vertebrate central nervous system (CNS), establishing a cellular diversity that is essential for the formation of neuronal circuits. The selective degeneration of specific types or classes of CNS neurons underlies many neurological disorders. This realization has generated interest in defining populations of progenitor cells that may serve as replenishable sources of neurons, with a view to treating neurodegenerative disorders. Directing such progenitor cells along specific pathways of neuronal differentiation in a systematic manner has proved difficult, not merely because the normal developmental pathways that generate most classes of CNS neurons remain poorly defined.

Studies of the neurogenic potential of progenitor cells have focused on three major classes of cells: (1) neural progenitors derived from embryonic or adult nervous tissue (Alvarez-Buylla et al., A unified hypothesis on the lineage of neural stem cells. *Nat. Rev. Neurosci.*, 2:287-93, 2001; Gage, F. H., Mammalian neural stem cells. *Science*, 287:1433-38, 2000; Temple, S., The development of neural stem cells. *Nature*, 414:112-17,2001; Uchida et al., Direct isolation of human central nervous system stem cells. *Proc. Natl. Acad. Sci. USA*, 97:14720-725, 2000); (2) non-neural progenitor cells derived from other tissues and organs (Brazelton et al., From marrow to brain: expression of neuronal phenotypes in adult mice. *Science*, 290:1775-79, 2000; Mezey et al., Turning blood into brain: cells bearing neuronal antigens generated in vivo from bone marrow. *Science*, 290:1779-82, 2000; Terada et al., Bone marrow cells adopt the phenotype of other cells by spontaneous cell fusion. *Nature*, 416:542-45, 2002; Ying et al., Changing potency by spontaneous fusion. *Nature*, 416: 545-48, 2002); and (3) embryonic stem (ES) cells (Bain et al., Embryonic stem cells express neuronal properties in vitro. *Dev. Biol.*, 168:342-57, 1995; Reubinoff et al., Neural progenitors from human embryonic stem cells. *Nat. Biotechnol.*, 19:1134-40, 2001; Schuldiner et al., Induced neuronal differentiation of human embryonic stem cells. *Brain Res.*, 913: 201-05,2001; Zhang et al., In vitro differentiation of transplantable neural precursors from human embryonic stem cells. *Nat. Biotechnol.*, 19:1129-33, 2001; Rathjen et al., Directed differentiation of pluripotent cells to neural lineages: homogenous formation and differentiation of a neurectoderm population. *Development*, 129:2649-61, 2002). ES cells possess the capacity to generate both neurons and neuroglial cells, and, in some instances, express cell-type markers characteristic of specific classes of neurons, including midbrain dopaminergic neurons (Kawasaki et al., Induction of midbrain dopaminergic neurons from ES cells by stromal cell-derived inducing activity. *Neuron*, 28:31-40, 2000; Lee et al., Efficient generation of midbrain and hindbrain neurons from mouse embryonic stem cells. *Nat. Biotechnol.*, 18:675-79, 2000). Despite these advances, however, it was not known, prior to the present invention, that ES cells can readily generate specific neuronal cell types, nor that they can recapitulate normal programs of neurogenesis.

Spinal motor neurons represent one CNS neuronal subtype for which many of the relevant pathways of neuronal specification have been defined (Jessell et al., Neuronal specification in the spinal cord: inductive signals and transcriptional codes. *Nat. Rev. Genet.*, 1:20-29, 2000; Lee et al., Transcriptional networks regulating neuronal identity in the developing spinal cord. *Nat. Neurosci.*, 4 Suppl.: 1183-91, 2001). The generation of spinal motor neurons appears to involve several developmental steps. Initially, ectodermal cells acquire a rostral neural character—a process achieved through the regulation of BMP (bone morphogenetic protein), FGF, and Wnt signalling (Munoz-Sanjuan et al., Neural induction, the default model and embryonic stem cells. *Nat. Rev. Neurosci.*, 3:271-80, 2002; Wilson et al., Neural induction: toward a unifying mechanism. *Nat. Neurosci.*, 4 Suppl.:1161-68, 2001). These rostral neural progenitors acquire a spinal positional identity in response to caudalizing signals that include retinoic acid (RA) (Blumberg et al., An essential role for retinoid signaling in anteroposterior neural patterning. *Development*, 124:373-79, 1997; Durston et al., Retinoids and related signals in early development of the vertebrate central nervous system. *Curr. Top. Dev. Biol.*, 40:111-75, 1998; Muhr et al., Convergent inductive signals specify midbrain, hindbrain, and spinal cord identity in gastrula stage chick embryos. *Neuron*, 23:689-702, 1999). Subsequently, spinal progenitor cells acquire a motor neuron progenitor identity in response to the ventralizing action of Sonic hedgehog protein (SHh) (Briscoe et al., Specification of neuronal fates in the ventral neural tube. *Curr. Opin. Neurobiol.*, 11:43-49, 2001).

Specification of motor neuron progenitor identity by SHh signalling is mediated through the establishment of a dorsoventral pattern of expression of homeodomain (HD) and basic helix-loop-helix (bHLH) transcription factors (Briscoe et al., supra). At a relatively high level of SHh signalling, a discrete progenitor domain—termed the pMN domain—is established; within this domain, cells appear committed to the generation of motor neurons rather than interneurons (Briscoe et al., A homeodomain protein code specifies progenitor cell identity and neuronal fate in the ventral neural tube. *Cell*, 101:435-45, 2000).

Progenitor cells in the pMN domain are characterized by the expression of two HD proteins (Pax6 and Nkx6.1) and a bHLH protein (Olig2) (Ericson et al., Pax6 controls progenitor cell identity and neuronal fate in response to graded SHh signaling. *Cell*, 90:169-80, 1997; Sander et al., Ventral neural patterning by Nkx homeobox genes: Nkx6.1 controls somatic motor neuron and ventral interneuron fates. *Genes Dev.*, 14:2134-39, 2000; Vallstedt et al., Different levels of repressor activity assign redundant and specific roles to Nkx6 genes in motor neuron and interneuron specification. *Neuron*, 31:743-55, 2001; Novitch et al., Coordinate regulation of motor neuron subtype identity and pan-neuronal properties by the bHLH repressor Olig2. *Neuron*, 31:773-89, 2001; Mizuguchi et al., Combinatorial roles of olig2 and neurogenin2 in the coordinated induction of pan-neuronal and subtype-specific properties of motoneurons. *Neuron*, 31:757-71, 2001). Each of these three transcription factors has an essential role in the specification of spinal motor neuron identity (Ericson et al., Pax6 controls progenitor cell identity and neuronal fate in response to graded SHh signaling. *Cell*, 90:169-80, 1997; Sander et al., Ventral neural patterning by Nkx homeobox genes: Nkx6.1 controls somatic motor neuron and ventral interneuron fates. *Genes Dev.*, 14:2134-39, 2000; Vallstedt et al., Different levels of repressor activity assign redundant and specific roles to Nkx6 genes in motor neuron and interneuron specification. *Neuron*, 31:743-55, 2001; Novitch et al., Coordinate regulation of motor neuron subtype identity and pan-neuronal properties by the bHLH repressor Olig2. *Neuron,* 31:773-89, 2001; Mizuguchi et al., Combinatorial roles of olig2 and neurogenin2 in the coordinated induction of pan-neuronal and subtype-specific properties of motoneurons. *Neuron,* 31:757-71, 2001; Zhou et al., The bHLH transcription factors OLIG2 and OLIG1 couple neuronal and glial subtype specification. *Cell,* 109:61-73, 2002; Lu et al., Common developmental requirement for Olig function indicates a motor neuron/oligodendrocyte connection. *Cell,* 109:75-86, 2002). Moreover, their combined activities drive motor neuron progenitors out of the cell cycle (Novitch et al., Coordinate regulation of motor neuron subtype identity and pan-neuronal properties by the bHLH repressor Olig2. *Neuron,* 31:773-89, 2001; Mizuguchi et al., Combinatorial roles of olig2 and neurogenin2 in the coordinated induction of pan-neuronal and subtype-specific properties of motoneurons. *Neuron,* 31:757-71, 2001), and direct the expression of downstream transcription factors (notably the HD protein, HB9) that consolidate the identity of post-mitotic motor neurons (Pfaff et al., Requirement for LIM homeobox gene Isl1 in motor neuron generation reveals a motor neuron-dependent step in interneuron differentiation. *Cell,* 84:309-20, 1996; Arber et al., Requirement for the homeobox gene Hb9 in the consolidation of motor neuron identity. *Neuron,* 23:659-764, 1999; Thaler et al., Active suppression of interneuron programs within developing motor neurons revealed by analysis of homeodomain factor HB9. *Neuron,* 23:675-87, 1999).

The above findings suggest that insights into normal pathways of neurogenesis can be applied in a rational manner to direct heterologous sets of progenitor cells, such as ES cells, into specific CNS neuronal subtypes. ES cells have been reported to generate cells with some of the molecular characteristics of motor neurons (Renoncourt et al., Neurons derived in vitro from ES cells express homeoproteins characteristic of motoneurons and interneurons. *Mech. Dev.,* 79:185-97, 1998). However, prior to the present invention, neither the pathway of generation of these neurons, nor their in vivo developmental potential, has been adequately explored.

SUMMARY OF THE INVENTION

The inventors have examined whether the extracellular signalling factors that operate along the rostrocaudal and dorsoventral axes of the neural tube, and which specify motor neuron fate in vivo, can be harnessed in vitro to direct the differentiation of mouse ES cells into functional spinal motor neurons. As disclosed herein, the inventors have determined that the exposure of neuralized ES cells to RA induces the differentiation of spinal progenitor cells, and that the activation of hedgehog (Hh) signalling directs these cells to generate motor neurons. The inventors have also shown that the intrinsic molecular pathway of motor neuron differentiation triggered by Hh signalling mimics that involved in motor neuron generation in vivo. The use of a GFP-based motor neuron marking method permitted the characterization of pure populations of ES-cell-derived motor neurons. Such motor neurons can repopulate the embryonic spinal cord in vivo, extend axons into the periphery, and undergo synaptic differentiation at sites of contact with skeletal muscles. Thus, normal pathways of neurogenesis can be subverted in a rational manner to direct ES cells into specific subclasses of CNS neurons.

Accordingly, the present invention provides an in vitro system for use in identifying a modulator of neural differentiation, comprising: (a) a collection of embryonic stem cells; (b) a rostralizing or caudalizing embryonic signalling factor; and (c) optionally, a dorsalizing or ventralizing embryonic signalling factor. In one embodiment, the embryonic stem cells are murine embryonic stem cells. In another embodiment, the embryonic stem cells are human embryonic stem cells. Also provided is a modulator identified by this system.

The present invention further provides a method for identifying a modulator of neural differentiation, by: (a) contacting an in vitro system, for use in identifying a modulator of neural differentiation of embryonic stem cells, with a candidate modulator; and (b) determining if the candidate modulator has an effect on neural differentiation of embryonic stem cells, wherein the in vitro system comprises: (a) a collection of embryonic stem cells; (b) a rostralizing or caudalizing embryonic signalling factor; and (c) optionally, a dorsalizing or ventralizing embryonic signalling factor. In one embodiment, the embryonic stem cells are murine embryonic stem cells. In another embodiment, the embryonic stem cells are human embryonic stem cells. Also provided is a modulator identified by this method.

Additionally, the present invention provides an in vitro system for use in identifying a modulator of neural differentiation, comprising a collection of embryonic stem cells that has been contacted with: (a) a rostralizing or caudalizing embryonic signalling factor, to produce a collection of neural progenitor cells; and (b) optionally, a dorsalizing or ventralizing embryonic signalling factor. In one embodiment, the embryonic stem cells are murine embryonic stem cells. In another embodiment, the embryonic stem cells are human embryonic stem cells. Also provided is a modulator identified by this system.

The present invention further provides a method for identifying a modulator of neural differentiation, by: (a) contacting an in vitro system, for use in identifying a modulator of neural differentiation of neural progenitor cells, with a candidate modulator; and (b) determining if the candidate modulator has an effect on neural differentiation of neural progenitor cells, wherein the in vitro system comprises a collection of embryonic stem cells that has been contacted with: (a) a rostralizing or caudalizing embryonic signalling factor, to produce a collection of neural progenitor cells; and (b) optionally, a dorsalizing or ventralizing embryonic signalling factor. In one embodiment, the embryonic stem cells are murine embryonic stem cells. In another embodiment, the embryonic stem cells are human embryonic stem cells. Also provided is a modulator identified by this method.

Additionally, the present invention provides a method for identifying a modulator of neural differentiation, by: (a) obtaining or generating a collection of embryonic stem cells; (b) contacting the embryonic stem cells simultaneously with a rostralizing or caudalizing embryonic signalling factor and a dorsalizing or ventralizing embryonic signalling factor, in the presence of a candidate modulator; and (c) determining if the candidate modulator modulates neural differentiation of the embryonic stem cells. In one embodiment, the embryonic stem cells are murine embryonic stem cells. In another embodiment, the embryonic stem cells are human embryonic stem cells. The method may further comprise the step of contacting the embryonic stem cells in step (b) with at least one neurotrophic factor. Alternatively, the method may further comprise the step of contacting the embryonic stem cells in step (b) with at least one conditioned medium. Also provided are modulators identified by these methods.

The present invention further provides a method for identifying a modulator of neural differentiation, by: (a) obtaining or generating a first collection of embryonic stem cells and a second collection of embryonic stem cells; (b) contacting the first collection of embryonic stem cells with a rostralizing or caudalizing embryonic signalling factor and a dorsalizing or ventralizing embryonic signalling factor, in the presence of a candidate modulator; (c) contacting the second collection of embryonic stem cells with a rostralizing or caudalizing embryonic signalling factor and a dorsalizing or ventralizing embryonic signalling factor, in the absence of the candidate modulator; and (d) determining if the candidate modulator in step (b) modulates neural differentiation of embryonic stem cells by comparing neural differentiation of the embryonic stem cells in step (b) with neural differentiation of the embryonic stem cells in step (c). In one embodiment, the embryonic stem cells are murine embryonic stem cells. In another embodiment, the embryonic stem cells are human embryonic stem cells. Also provided is a modulator identified by this method.

The present invention further provides a method for identifying a modulator of neural differentiation, by: (a) obtaining or generating a collection of embryonic stem cells; (b) contacting the collection of embryonic stem cells with an amount of a rostralizing or caudalizing embryonic signalling factor effective to produce neural progenitor cells; (c) contacting the neural progenitor cells with a dorsalizing or ventralizing embryonic signalling factor, in the presence of a candidate modulator; and (d) determining if the candidate modulator modulates neural differentiation of the embryonic stem cells. In one embodiment, the embryonic stem cells are murine embryonic stem cells. In another embodiment, the embryonic stem cells are human embryonic stem cells. Also provided is a modulator identified by this method.

Additionally, the present invention provides a method for identifying a modulator of a Wnt signalling pathway, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a Wnt signalling pathway; (d) contacting the second collection of cells with an activator of a Wnt signalling pathway; and (e) determining if the candidate modulator in step (b) modulates neural differentiation by comparing neural differentiation of the cells in step (b) with neural differentiation of the cells in step (c), wherein modulation of neural differentiation is indicative of modulation of a Wnt signalling pathway. Also provided is a modulator identified by this method.

The present invention further provides a method for identifying a modulator of neural differentiation, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a Wnt signalling pathway; (d) contacting the second collection of cells with an activator of a Wnt signalling pathway; and (e) determining if the candidate modulator in step (b) modulates neural differentiation by comparing neural differentiation of the cells in step (b) with neural differentiation of the cells in step (c). Also provided is a modulator identified by this method.

Furthermore, the present invention provides a method for identifying a modulator of Wnt-dependent neural differentiation, by: (a) obtaining or generating a collection of cells selected from the group consisting of embryonic stem cells (e.g., murine or human embryonic stem cells), embryoid bodies, and neural progenitor cells; (b) contacting the collection of cells with a candidate modulator; and (c) determining if the candidate modulator modulates Wnt-dependent neural differentiation of the cells in the collection. In one embodiment of the present invention, the collection of cells in step (b) is further contacted with the candidate modulator in the presence of an activator of a Wnt signalling pathway. Also provided is a modulator identified by this method.

The present invention also provides a method for identifying a modulator of a BMP (bone morphogenetic protein) signalling pathway, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a BMP signalling pathway; (d) contacting the second collection of cells with an activator of a BMP signalling pathway; and (e) determining if the candidate modulator in step (b) modulates neural differentiation by comparing neural differentiation of the cells in step (b) with neural differentiation of the cells in step (c), wherein modulation of neural differentiation is indicative of modulation of a BMP signalling pathway. Also provided is a modulator identified by this method.

Additionally, the present invention provides a method for identifying a modulator of neural differentiation, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a BMP signalling pathway; (d) contacting the second collection of cells with an activator of a BMP signalling pathway; and (e) determining if the candidate modulator in step (b) modulates neural differentiation by comparing neural differentiation of the cells in step (b) with neural differentiation of the cells in step (c). Also provided is a modulator identified by this method.

The present invention further provides a method for identifying a modulator of BMP-dependent neural differentiation, by: (a) obtaining or generating a collection of cells selected from the group consisting of embryonic stem cells (e.g., murine or human embryonic stem cells), embryoid bodies, and neural progenitor cells; (b) contacting the collection of cells with a candidate modulator; and (c) determining if the candidate modulator modulates BMP-dependent neural differentiation of the cells in the collection. In one embodiment of the present invention, the collection of cells in step (b) is further contacted with the candidate modulator in the presence of an activator of a BMP signalling pathway. Also provided is a modulator identified by this method.

The present invention also provides a method for identifying a modulator of a Hh signalling pathway, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a Hh signalling pathway; (d) contacting the second collection of cells with an activator of a Hh signalling pathway; and (e) determining if the candidate modulator in step (b) modulates neural differentiation by comparing neural differentiation of the cells in step (b) with neural differentiation of the cells in step (c), wherein modulation of neural differentiation is indicative of modulation of a Hh signalling pathway. Additionally, the present invention provides a modulator identified by this method.

The present invention further provides a method for identifying a modulator of neural differentiation, by: (a) obtaining or generating a first collection of cells selected from the group consisting of embryonic stem cells (e.g., murine or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a Hh signalling pathway; (d) contacting the second collection of cells with an activator of a Hh signalling pathway; and (e) determining if the candidate modulator in step (b) modulates neural differentiation by comparing neural differentiation of the cells in step (b) with neural differentiation of the cells in step (c). Also provided is a modulator identified by this method.

In addition, the present invention provides a method for identifying a modulator of Hh-dependent neural differentiation, by: (a) obtaining or generating a collection of cells selected from the group consisting of embryonic stem cells (e.g., murine or human embryonic stem cells), embryoid bodies, and neural progenitor cells; (b) contacting the collection of cells with a candidate modulator; and (c) determining if the candidate modulator modulates Hh-dependent neural differentiation of the cells in the collection. In one embodiment of the present invention, the collection of cells in step (b) is further contacted with the candidate modulator in the presence of an activator of a Hh signalling pathway. Also provided is a modulator identified by this method.

Additional aspects of the present invention will be apparent in view of the description which follows.

DETAILED DESCRIPTION OF THE INVENTION

Figure 1:
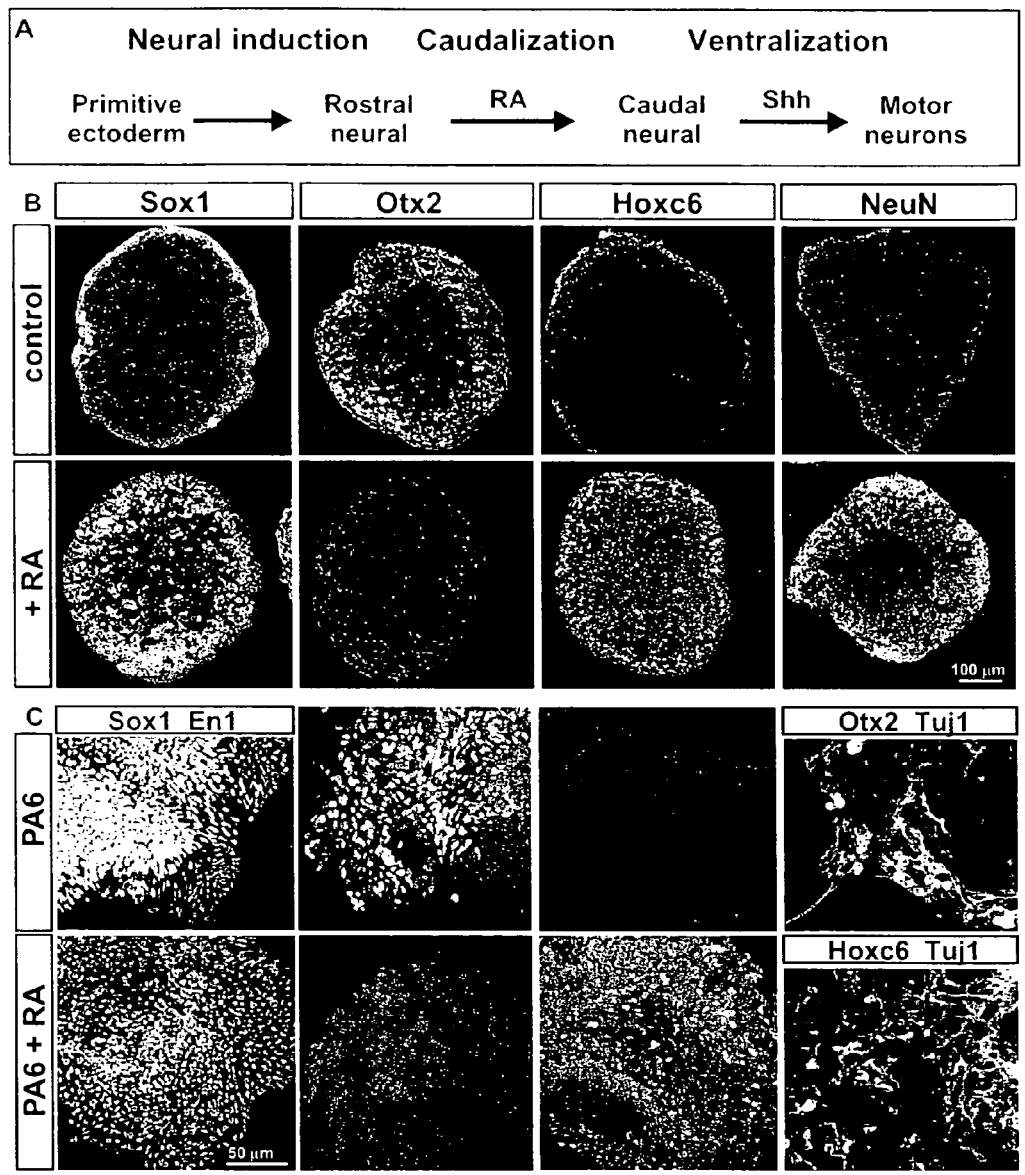
FIG. 1 demonstrates that retinoic acid induces caudal positional identity in neuralized embryoid bodies. (A) Progressive steps in the specification of spinal motor neuron identity. Neural inductive signals convert primitive ectodermal cells to a neural fate. During the initial phases of neural induction, progenitor cells express an anterior identity. Extrinsic signals, including retinoic acid (RA), convert rostral neural plate cells to progressively-more-caudal identities. Caudal neural progenitors are converted to motor neurons under the influence of sonic hedgehog (SHh) signalling. (B) Expression of pan-neural and rostrocaudal markers in embryoid bodies (EBs) grown in the presence or absence of RA (2 μM). The expression of early neural plate marker, Sox1, was increased in EBs cultured for 3 days in the presence of RA. Otx2 expression was present in EBs grown in the absence of RA for 3 days, but was extinguished in the presence of RA. Hoxc6 was expressed in EBs exposed to RA for 5 days. Large numbers of post-mitotic neurons, marked by NeuN expression, were observed when EBs were grown for 5 days in the presence of RA. (C) ES cells cultured on PA6 cells for 6 days expressed neuronal marker, Sox1. Many Sox1$^+$cells co-expressed En1, but did not express Hoxc6. Many TuJ1$^+$ neurons co-expressed Otx2. Addition of RA (2 μM) to ES cells grown on PA6 cells resulted in the extinction of En1 and Otx2 expression, and the expression of Hoxc6 in progenitor cells and TuJ1$^+$ post-mitotic neurons. Many of these neurons expressed HB9, and, therefore, were motor neurons. (See FIG. 9.)

During development, neural cells are generated from embryonic stem cells through a series of developmental steps involving the regulation of signalling factors that impart to the stem cells a particular directional or positional character. Initially, ectodermal cells may acquire a rostral or caudal neural character, and differentiate into rostral or caudal neural progenitor cells, through the regulation of rostralizing and/or caudalizing embryonic signalling factors. Thereafter, the neural progenitor cells may differentiate further, acquiring the identity of a subtype of progenitor cells, or becoming a fully-differentiated neural cell, in response to the action of dorsalizing and/or ventralizing embryonic signalling factors.

For example, a motor neuron may develop from an ES cell in response to a variety of signalling factors. Initially, the regulation of BMP, FGF, and Wnt signalling will cause ectodermal cells to acquire a rostral neural character. The resulting rostral neural progenitors then acquire a spinal positional identity in response to caudalizing signals that include retinoic acid (RA). The specification of motor neuron progenitor identity by SHh signalling is mediated through the establishment of a dorsoventral pattern of expression of homeodomain (HD) and basic helix-loop-helix (bHLH) transcription factors. At a relatively high level of SHh signalling, a discrete progenitor domain—termed the pMN domain—is established. Within this domain, cells appear committed to the generation of motor neurons, rather than interneurons. Progenitor cells in the pMN domain are characterized by the expression of two HD proteins, Pax6 and Nkx6.1, and a bHLH protein, Olig2. Each of these three transcription factors has an essential role in the specification of spinal motor neuron identity. Moreover, their combined activities drive motor neuron progenitors out of the cell cycle, and direct the expression of downstream transcription factors (notably the HD protein, HB9) that consolidate the identity of post-mitotic motor neurons.

Spinal motor neurons play an essential role in the control of motor behavior, and their degeneration underlies many neurological disorders. Inductive signals and transcription factors involved in motor-neuron generation have been identified, suggesting that insights into normal development can be used to direct stem cells to a motor neuron fate in a rational manner. The inventors demonstrate herein that mouse embryonic stem (ES) cells can be induced by extrinsic signalling factors to differentiate initially into spinal progenitor cells, and subsequently into spinal motor neurons. The molecular pathway of motor neuron generation from ES-cell-derived neural progenitors recapitulates that deployed in vivo. ES-cell-derived motor neurons introduced into the embryonic spinal cord populate the ventral horn, extend axons into the periphery, and undergo synaptic differentiation at sites of contact with target skeletal muscles. Thus, inductive signals involved in normal pathways of neurogenesis can direct ES cells to form specific classes of CNS neurons.

As discussed in detail in the Examples below, the inventors have examined whether the delineation of extracellular inductive signals and transcription factors, which are involved in the conversion of neural progenitor cells to specific neuronal subtypes in vivo, permits a rational, embryology-based approach to the differentiation of ES cells into specific classes of CNS neurons. The inventors' findings show that mouse ES cells can generate spinal motor neurons at high efficiency, and that the pathway of motor neuron generation from ES cells recapitulates the steps of motor neuron generation in vivo. ES-cell-derived motor neurons repopulate the ventral spinal cord in vivo, extend axons into the periphery, and form synapses with muscle targets. These studies establish the feasibility of applying insights into normal developmental signalling cascades, particularly the control of extracellular inductive signals, to direct the differentiation of ES cells into specific classes of CNS neurons. The ability of ES-cell-derived motor neurons to innervate target muscle cells offers the potential for a systematic evaluation of the use of such neurons to restore motor function in mammalian models of spinal cord injury and motor neuron degenerative diseases.

The specification of motor neuron fate in vivo can be considered in three sequential steps: (a) the primary neuralization of ectodermal cells; (b) the secondary caudalization of neural cells; and (c) the ventralization of caudalized neural cells (Jessell et al., Neuronal specification in the spinal cord: inductive signals and transcriptional codes. *Nat. Rev. Genet.*, 1:20-29, 2000; Wilson et al., Neural induction: toward a unifying mechanism. *Nat. Neurosci.*, 4th Suppl.: 1161-68, 2001). The inventors' results, discussed herein, provide evidence that the pathway of differentiation of ES cells into motor neurons resembles the normal programs involved in the caudalization and ventralization of neural cells.

Neural plate cells, regardless of their final positional identities, appear initially to possess a rostral character (Munoz-Sanjuan et al., Neural induction, the default model and embryonic stem cells. *Nat. Rev. Neurosci.*, 3:271-80, 2002). The subsequent imposition of a spinal cord character appears to involve RA-mediated signals provided by the paraxial mesoderm (Muhr et al., Convergent inductive signals specify midbrain, hindbrain, and spinal cord identity in gastrula stage chick embryos. *Neuron*, 23:689-702, 1999; Wilson et al., Neural induction: toward a unifying mechanism. *Nat. Neurosci.*, 4 Suppl.: 1161-68, 2001). In particular, RA has been shown to specify spinal cord character at the expense of midbrain or rostral hindbrain identity (Muhr et al., Convergent inductive signals specify midbrain, hindbrain, and spinal cord identity in gastrula stage chick embryos. *Neuron*, 23:689-702, 1999). The inventors have found that ES cells that have been neuralized by exposure to PA6 cell activity express a midbrain positional character (see, also, Kawasaki et al., Induction of midbrain dopaminergic neurons from ES cells by stromal cell-derived inducing activity. *Neuron*, 28:31-40, 2000), but can be converted to a cervical spinal positional identity upon exposure to RA. The requirement for RA exposure in motor-neuron generation described in these studies is complemented by an RA-mediated inhibition of midbrain dopaminergic neuronal differentiation (Kawasaki et al., Induction of midbrain dopaminergic neurons from ES cells by stromal cell-derived inducing activity. *Neuron*, 28:31-40, 2000). Together, these findings support the view that RA promotes spinal cord positional identity in neuralized EBs in a manner that parallels its normal role in patterning the rostrocaudal axis of the neural tube.

Why do the spinal cord cells, induced by RA in EBs, possess a rostral cervical positional identity? A likely reason for this comes from the finding that, at times after the specification of a generic spinal progenitor identity, the rostrocaudal positional identity of spinal cord cells continues to be influenced by ongoing RA signalling (Liu et al., Assigning the positional identity of spinal motor neurons. Rostrocaudal patterning of Hox-c expression by FGFs, Gdf11, and retinoids. *Neuron*, 32:997-1012, 2001). In particular, RA-mediated signalling promotes the acquisition of rostral cervical spinal positional character, at the expense of thoracic and lumbar positional identities (Liu et al., Assigning the positional identity of spinal motor neurons. Rostrocaudal patterning of Hox-c expression by FGFs, Gdf11, and retinoids. *Neuron*, 32:997-1012, 2001). Thus, the exposure of neuralized ES cells to RA is likely to account both for the emergence of an initial spinal positional character, and for the restriction of these cells to a rostral cervical identity.

ES cells that have acquired a spinal progenitor identity also appear to follow a normal pathway of motor neuron progenitor specification. One line of evidence for this is the sensitivity of these cells to Hh signalling. Motor-neuron generation from ES-cell-derived spinal progenitors, as in vivo (Chiang et al., Cyclopia and defective axial patterning in mice lacking Sonic hedgehog gene function. *Nature*, 383:407-13, 1996), is completely dependent on Hh signalling. Thus, the generation of a few motor neurons in the absence of added Hh appears to result from expression of low levels of endogenous Hh activity in EBs, possibly mediated by IHh or SHh (Byrd et al., Hedgehog is required for murine yolk sac angiogenesis. *Development*, 129:361-72, 2002; Dyer et al., Indian hedgehog activates hematopoiesis and vasculogenesis and can respecify prospective neurectodermal cell fate in the mouse embryo. *Development*, 128:1717-30, 2001). Conversely, elevating the level of Hh signalling in EBs markedly enhances motor neuron generation.

A second line of evidence is provided by the profile of expression of progenitor transcription factors elicited in EBs by Hh signalling. In the absence of Hh signalling, spinal progenitors in EBs exhibit a dorsal and intermediate neural progenitor identity. Activation of Hh signalling extinguishes the expression of dorsal progenitor determinants in a concentration-dependent manner that closely mimics the response of primary spinal progenitor cells (Briscoe et al., Specification of neuronal fates in the ventral neural tube. *Curr. Opin. Neurobiol.*, 11 (1):43-49, 2001). Moreover, high levels of Hh signalling activity induce the expression of Nkx6.1 and Olig2—the two progenitor cell transcription factors most intimately linked with motor-neuron generation in vivo (Sander et al., Ventral neural patterning by Nkx homeobox genes: Nkx6.1 controls somatic motor neuron and ventral interneuron fates. *Genes Dev.*, 14:2134-39, 2000; Vallstedt et al., Different levels of repressor activity assign redundant and specific roles to Nkx6 genes in motor neuron and interneuron specification. *Neuron*, 31:743-55, 2001; Novitch et al., Coordinate regulation of motor neuron subtype identity and pan-neuronal properties by the bHLH repressor Olig2. *Neuron*, 31:773-89, 2001; Mizuguchi et al., Combinatorial roles of olig2 and neurogenin2 in the coordinated induction of pan-neuronal and subtype-specific properties of motoneurons. *Neuron*, 31:757-71, 2001). Taken together, these findings indicate that neuralized ES cells respond both to rostrocaudal and dorsoventral patterning signals in a manner that closely resembles the behavior of primary neural plate cells, initially generating spinal cord progenitor cells, and subsequently generating motor neuron progenitors.

The inventors' studies also implicate the steps involved in the initial phase of neural differentiation from ES cells. In vivo, neural induction appears to depend on the blockade BMP signalling (Munoz-Sanjuan et al., Neural induction, the default model and embryonic stem cells. *Nat. Rev. Neurosci.*, 3:271-80, 2002), and, at least in chick, on exposure to FGFs (Streit et al., Initiation of neural induction by FGF signalling before gastrulation. *Nature*, 406:74-78, 2000; Wilson et al., An early requirement for FGF signalling in the acquisition of neural cell fate in the chick embryo. *Curr. Biol.*, 10421-429, 2000; Wilson et al., The status of Wnt signalling regulates neural and epidermal fates in the chick embryo. *Nature*, 411:325-30, 2001). Recent studies have suggested a role for inhibition of BMP signalling in neural induction in ES cells (Gratsch et al., Noggin and chordin have distinct activities in promoting lineage commitment of mouse embryonic stem (ES) cells. *Dev. Biol.*, 245:83-94, 2002; Tropepe et al., Direct neural fate specification from embryonic stem cells: a primitive mammalian neural stem cell stage acquired through a default mechanism. *Neuron*, 30:65-78, 2001). However, additional studies are needed to determine how closely the early steps of neural specification in ES cells conform to pathways of neural induction in vivo.

Several observations indicate that ES-cell-derived motor neurons also behave in vivo in a manner that resembles their embryonic counterparts. Firstly, eGFP$^+$ motor neurons are typically restricted to the ventral spinal cord, often in a ventrolateral position—which is characteristic of endogenous motor neurons. In contrast, ES cell-derived spinal interneurons are scattered throughout the dorsoventral axis of the spinal cord. These observations suggest that ES-cell-derived motor neurons and interneurons undergo an active process of segregation after their introduction into the host spinal cord. An alternative possibility is that motor neurons that fail to populate the ventral spinal cord die or extinguish eGFP expression. One argument against this later possibility is that motor neurons generated in the dorsal spinal cord in response to misexpression of Nkx6 or MNR2 proteins do survive and differentiate in an ectopic dorsal position (Tanabe et al., Specification of motor neuron identity by the MNR2 homeodomain protein. *Cell*, 95:67-80, 1998; Briscoe et al., A homeodomain protein code specifies progenitor cell identity and neuronal fate in the ventral neural tube. *Cell*, 101:435-45, 2000).

Secondly, ES-cell-derived motor neurons project axons out of the spinal cord via the ventral root, and select the major peripheral pathways taken by somatic motor neurons. The projection of the axons of ES-cell-derived motor neurons into the limb is notable, since very few of these neurons express a LIM HD code appropriate for limb-projecting LMC neurons (Tsuchida et al., Topographic organization of embryonic motor neurons defined by expression of LIM homeobox genes. *Cell*, 79:957-70, 1994). A similar mismatch between the LIM HD code of motor neurons and peripheral axonal trajectories is found in two other experimental contexts. Overexpression of Lhx3 confers an MMC molecular identity to motor neurons at limb levels of the spinal cord; yet, many of these motor neurons still project axons into the limb (Sharma et al., Genetic and epigenetic mechanisms contribute to motor neuron pathfinding. *Nature*, 406:515-19, 2000). In addition, thoracic level motor neurons that have been placed at limb levels of the spinal cord can still project into the limb (O'Brien et al., Development and survival of thoracic motoneurons and hindlimb musculature following transplantation of the thoracic neural tube to the lumbar region in the chick embryo: anatomical aspects. *J. Neurobiol.*, 21:313-40, 1990). Thus, the projection of the axons of ES-cell-derived motor neurons into the limb is likely to reflect the fact that the LIM HD code can be overridden in circumstances in which motor neurons face an altered or restricted choice of peripheral pathways.

Thirdly, on arrival at target muscles, the axons of ES-cell-derived motor neurons exhibit many signs of pre-synaptic differentiation, notably the expression of cholinergic neurotransmitter properties. Moreover, these presynaptic specializations are found in alignment with focal clusters of ACh receptors on the post-synaptic muscle membrane, suggesting that the synaptic contacts formed between ES-cell-derived motor neurons and skeletal muscles are functional. Together, these in vivo studies show that ES-cell-derived motor neurons are able to negotiate successive steps in the normal developmental program through which a newly-generated motor neuron in the spinal cord innervates its skeletal muscle target.

Finally, the efficiency with which inductive signals are able to convert ES cells into motor neurons suggests a general strategy for generating other predefined classes of CNS neurons, through systematic variation in the identity and concentration of rostrocaudal and dorsoventral patterning signals to which ES cells are exposed. The ability to direct cell fate solely through the use of extracellular factors, without the need to manipulate ES cells genetically (see, e.g., Kyba et al., HoxB4 confers definitive lymphoid-myeloid engraftment potential on embryonic stem cell and yolk sac hematopoietic progenitors. *Cell*, 109:29-37, 2002), may permit a direct extension of this strategy to human ES cells and other classes of neural progenitor cells.

In accordance with the foregoing, the present invention provides a method for inducing neural differentiation of: an embryonic stem cell (e.g., inducing differentiation of an embryonic stem cell into a differentiated neural cell), and a differentiated neural cell produced by this method. As used herein, the term "inducing differentiation of an embryonic stem cell" means activating, initiating, or stimulating an embryonic stem cell to undergo differentiation—the cellular process by which cells become structurally and functionally specialized during development. As further used herein, the term "neural differentiation" refers to the series of events that specifies the process whereby embryonic stem cells, embryoid bodies, neural progenitor cells, other early-stage neural cells, and any other starting material capable of differentiating into a neural cell, differentiate into partially-differentiated neural cells, fully-differentiated neural cells, and other later-stage neural cells. The term "neural differentiation" includes the series of events that specifies the differentiation of neural progenitor cells of one character/identity into later-stage neural progenitor cells of another character/identity.

Embryonic stem (ES) cells are cultured cells, derived from the pluripotent inner cell mass of blastocyst stage embryos, that are capable of replicating indefinitely. In general, ES cells have the potential to differentiate into other cells (i.e., they are pluripotent); thus, they may serve as a continuous source of new cells. ES cells in culture are known to form complex structures called "embryoid bodies" (EBs). EBs are clumps of ES cells that develop in a manner that is analogous to the manner in which cells develop during the early stages of embryo development. In certain embodiments, the ES cells of the present invention may form EBs.

The ES cells of the present invention may be obtained from any animal, but are preferably obtained from a mammal (e.g., human, domestic animal, or commercial animal). In one embodiment of the present invention, the ES cells are murine embryonic stem cells. In another (preferred) embodiment, the ES cells are obtained from a human.

As used herein, a "neural cell", "neuronal cell", or "neuron", is a conducting or nerve cell of the nervous system that typically consists of a cell body (perikaryon) that contains the nucleus and surrounding cytoplasm; several short, radiating processes (dendrites); and one long process (the axon), which terminates in twig-like branches (telodendrons), and which may have branches (collaterals) projecting along its course. Examples of neurons include, without limitation, neurons of the dorsal root ganglia (DRG), motor neurons, peripheral neurons, sensory neurons, neurons of the spinal cord, and ventral interneurons, all of which may be cholinergic, dopaminergic, or serotonergic. As further used herein, a "differentiated neural cell" is a partially-differentiated or fully-differentiated neural cell of the central nervous system (CNS) or peripheral nervous system (PNS), and includes, without limitation, a fully-differentiated ganglion cell, glial (or neuroglial) cell (e.g., an astrocyte, oligodendrocyte, or Schwann cell), granule cell, neuronal cell (or neuron), and stellate cell, as well as any neural precursor cells or neural progenitor cells thereof. In one embodiment of the present invention, the differentiated neural cells are derived from ES cells.

Progenitor cells (also referred to herein as "precursor cells") are parent cells which, during development and differentiation, give rise to distinct cell lineages by a series of cell divisions. "Neural progenitor cells" or "neural precursor cells", for example, have acquired a neural-cell fate or character, in that they are committed to a cell lineage that can develop, eventually, into fully-differentiated neural cells of the CNS or PNS. However, such neural precursor/progenitor cells may not yet be dedicated to a particular type, or subclass, of neural cell. Initially, for example, neural progenitor cells may acquire an anterior/posterior character (e.g., neural progenitor cells of a forebrain or midbrain character) and/or a rostral/caudal or dorsal/ventral character (e.g., rostral neural progenitor cells). Thereafter, they may assume a positional identity (e.g., cerebellar progenitor cells, cerebral progenitor cells, and spinal progenitor cells).

Partially-differentiated neural progenitor cells may become committed to a cell line that will differentiate into a specific type of neural cell (e.g., they may be progenitor cells of astrocytes, ganglion cells, granule cells, neurons, oligodendrocytes, Schwann cells, and stellate cells), and, thereafter, may give rise to fully-differentiated neural cells (e.g., astrocyte, ganglion cells, granule cells, neurons (e.g., dorsal root ganglion (DRG) neurons; motor neurons; peripheral neurons; spinal cord neurons, such as LH2-positive dorsal spinal neurons; and dorsal or ventral interneurons), oligodendrocytes, Schwann cells, and stellate cells). Moreover, through the course of differentiation, a neural progenitor cell may become repositioned, or may change its character (e.g., positional) or identity, without differentiating into a fully-differentiated neural cell. For example, an earlier-stage neural progenitor cell, which initially has a forebrain/midbrain character, may caudalize or rostralize, or assume a dorsal spinal identity, as it differentiates into a later-stage neural progenitor cell. A neural progenitor cell that has changed its character or identity, without differentiating all the way to a fully-differentiated neural cell, is referred to herein as a "repositioned neural progenitor cell".

In view of the foregoing, the neural progenitor cell, or partially-differentiated neural cell, of the present invention may be a cell, with a neural-cell fate or identity, that has acquired a directional or positional character and/or that has committed to developing into a particular class of neural cell, but is not a fully-differentiated neural cell. In one embodiment, the neural progenitor cells of the present invention are derived from ES cells.

In one embodiment of the present invention, the differentiated neural cell is a fully-differentiated motor neuron (e.g., a post-mitotic motor neuron or a spinal motor neuron). In another embodiment of the present invention, the differentiated neural cell is genetically marked, in that it expresses enhanced green fluorescent protein (eGFP), as described herein. The eGFP genetic marker may be particularly useful in a method for isolating and/or purifying a population of differentiated neural cells, or in a method for monitoring repopulation of a spinal cord, as described below.

Differentiation of the appropriate starting material (e.g., ES cells or early-stage neural cells) into partially- or fully-differentiated neural cells may be detected by known cellular or molecular procedures, and assays and methods disclosed herein. For example, as discussed below, the various stages of neural differentiation may be determined using gene or protein markers. Similarly, stages of neural differentiation may be analyzed by studying ESTs and the patterns of gene expression—techniques that are well known in the art.

The method of the present invention comprises contacting an embryonic stem cell with a rostralizing or caudalizing embryonic signalling factor, and a dorsalizing or ventralizing embryonic signalling factor, in amounts effective to produce a differentiated neural cell. As used herein, a "factor" shall include a protein, polypeptide, peptide, nucleic acid (including DNA or RNA), antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion.

As further used herein, an "embryonic signalling factor" is a factor that carries information (a signal) to cells in an embryo during the course of development and differentiation. Such information, for example, may relate to the direction or position of cells in an embryo, and may determine the path of differentiation that will be followed by those cells that receive the information. The embryonic signalling factor of the present invention may be, for example, a morphogenic agent or a neural factor. Examples of embryonic signalling factors for use in the present invention, include, without limitation, a retinoid (e.g., retinoic acid (RA)) and its receptor, bone morphogenic proteins (BMPs) (e.g., BMP1 through to BMP7, including BMP2 and BMP4) and their receptors, fibroblast growth factors (FGFs) (e.g., alpha FGF, FGF8, FGF10, HBGF1, basic FGF, beta FGF, and HBGF) and their receptors, a Wnt protein (e.g., Wnt3a or Wnt5a) and its receptor, hedgehog proteins (e.g., DHh, sonic hedgehog (SHh), and Indian hedgehog (1Hh)) and their receptors, agonists of hedgehog signalling (e.g., Hh-Ag1.3), and other activators of a hedgehog signalling pathway.

Additionally, as used herein, the term "rostralizing embryonic signalling factor" refers to a factor that induces, or contributes to, development in the direction of the top, or superior position, of an object or subject. Contrastingly, a "caudalizing embryonic signalling factor" is a factor that induces, or contributes to, development in the direction of the bottom, tail, or inferior position of an object or subject. Embryonic signalling factors that contribute to the assignment of rostrocaudal identity may result in the differentiation of ES cells into neural progenitor cells. Examples of rostralizing and caudalizing embryonic signalling factors for use in the present invention, include, without limitation, a retinoid (such as RA), BMP, FGF, Wnt, and their receptors. RA is known to play a role in assigning rostrocaudal identity during development. Recently, it has been shown that Wnt signalling also plays a role in assigning rostrocaudal identity (Nordström et al., Progressive induction of caudal neural character by graded Wnt signaling. *Nat. Neurosci.*, 5(6):525-32, 2002). Thus, in one embodiment of the present invention, the rostralizing embryonic signalling factor is a retinoid (e.g., RA), Wnt, or one or their receptors. In another embodiment of the invention, the caudalizing embryonic signalling factor is a retinoid (e.g., RA), Wnt, or one of their receptors.

The term "dorsalizing embryonic signalling factor", as used herein, refers to a factor that induces, or contributes to, development in the direction of the back or posterior position of an object or subject. The term "ventralizing embryonic signalling factor", as used herein, is a protein or other agent that induces, or contributes to, development in the direction of the front or anterior position of an object or subject. Embryonic signalling factors that contribute to the assignment of dorsoventral identity may result in the differentiation of ES cells into neural progenitor cells or into fully-differentiated neural cells. Examples of dorsalizing and ventralizing embryonic signalling factors for use in the present invention include, without limitation, BMP, Wnt, hedgehog proteins, agonists of hedgehog signalling, other activators of a hedgehog signalling pathway, and their receptors. SHh signalling, for example, is known to provide spinal progenitor cells with the identity of motor neuron progenitor cells.

In one embodiment of the present invention, the dorsalizing embryonic signalling factor is BMP, Wnt, or a receptor thereof. In another embodiment of the present invention, the ventralizing embryonic signalling factor is an activator of a hedgehog signalling pathway. As used herein, "hedgehog" refers to any member of the hedgehog family of proteins now known or later discovered (e.g., desert hedgehog (DHh), sonic hedgehog (SHh), and Indian hedgehog (IHh)). As further used herein, "hedgehog signalling pathway" refers to the cascade of biochemical signalling that includes, is initiated by, or directly or indirectly results from release of a hedgehog protein, particularly signalling that relates to direction or position of cells in an embryo during development and differentiation. An "activator" of a hedgehog signalling pathway includes a factor that effects, increases, induces, initiates, or stimulates release of a hedgehog protein; a factor that effects or produces biochemical signalling within a hedgehog signalling pathway; and a factor that increases, induces, initiates, or stimulates signalling within a hedgehog signalling pathway. By way of example, the activator of hedgehog signalling may be a hedgehog protein (e.g., DHh, SHh, or IHh), a hedgehog receptor, or an agonist of a hedgehog signalling pathway (e.g., Hh-Ag1.3 or a Frizzled protein, such as Frizzled 8 or mFrz8CRD-IgG). An "agonist" of a hedgehog signalling pathway, as used herein, is a factor that has affinity for, and stimulates physiologic activity at, cell receptors normally stimulated by naturally-occurring substances, such that signalling in a hedgehog signalling pathway within the cell is increased, initiated, stimulated, or induced.

The embryonic signalling factors, BMP, FGF, Wnt, DHh, SHh, IHh, and agonists of hedgehog signalling pathways are proteins. As used herein, "BMP" includes both a BMP protein and a BMP analogue; "FGF" includes both an FGF protein and an FGF analogue; "Wnt" includes both a Wnt protein and a Wnt analogue; "SHh" includes both an SHh protein and an SHh analogue; "DHh" includes both a DHh protein and a DHh analogue; and "IHh" includes both an IHh protein and an IHh analogue. Unless otherwise indicated, "protein" shall include a protein, protein domain, polypeptide, or peptide. A particular protein's "analogue", as used herein, is a functional variant of the protein, having that protein's biological activity and 60% or greater (preferably, 70% or greater) amino-acid-sequence homology with the protein. An "analogue" includes a variant of the protein that has a homologous three-dimensional conformation. As further used herein, the term "biological activity" refers to the signalling activity of the BMP, FGF, Wnt, DHh, SHh, or IHh protein during development and differentiation, as described below.

Additionally, as used herein, "conservative substitutions" are those amino acid substitutions which are functionally equivalent to the substituted amino acid residue, either because they have similar polarity or steric arrangement, or because they belong to the same class as the substituted residue (e.g., hydrophobic, acidic, or basic). The term "conservative substitutions", as defined herein, includes substitutions having an inconsequential effect on the ability of a protein of the present invention to effect signalling during development and differentiation.

As discussed herein, BMP, FGF, Wnt, DHh, SHh, and IHh are proteins. In contrast, retinoids are derivatives of vitamin A; and retinoic acid (RA), or vitamin A, is an acid of the aldehyde molecule, retinal, that is believed to be a morphogen. RA is readily available; it may be obtained, for example, from Sigma Chemical Co. (St. Louis, Mo.). The other factors of the present invention may be produced synthetically or recombinantly, or isolated from native cells. Preferably, proteins are produced recombinantly, using conventional techniques and cDNA encoding the proteins. SHh and IHh (as well as Hh-Ag1.3) also may be obtained from Curis, Inc. (Cambridge, Mass.).

The method of the present invention comprises contacting an embryonic stem cell with a rostralizing and/or caudalizing embryonic signalling factor and a dorsalizing or ventralizing embryonic signalling factor. The embryonic signalling factors are provided in amounts effective to produce a differentiated neural cell. These amounts may be readily determined by the skilled artisan, based upon known procedures and methods disclosed herein. In a preferred embodiment of the present invention, the embryonic stem cell is contacted with the rostralizing and/or caudalizing embryonic signalling factor prior to contact with the dorsalizing or ventralizing embryonic signalling factor.

The inventors have demonstrated herein that neurons cultured in the presence of neurotrophic factors survive and elaborate processes. Accordingly, in another embodiment, the method of the present invention further comprises the step of contacting the embryonic stem cell with at least one neurotrophic factor, following contact with the dorsalizing or ventralizing embryonic signalling factor. As used herein, a "neurotrophic factor" is a factor involved in the nutrition or maintenance of neural tissue. Neurotrophic factors, may further the development and differentiation of committed neural progenitor cells, or they may induce or enhance the growth and survival of differentiated neural cells. A classic example of a neurotrophic factor is NGF (nerve growth factor). Other examples of neurotrophic factors for use in the present invention include, without limitation, GDNF, NGF, NT3, CNTF, and BDNF. These factors may be obtained from R&D Systems, Inc. (Minneapolis, Minn.). The neurotrophic factors of the present invention are provided in amounts effective to produce a fully-differentiated neural cell of the CNS or PNS (e.g., a neuron). This amount may be readily determined by the skilled artisan, based upon known procedures and methods disclosed herein.

In the method of the present invention, embryonic stem (ES) cells may be contacted with effective amounts of embryonic signalling factors in vitro, or in vivo in a subject. The embryonic signalling factors may be contacted with an ES cell by introducing the factors into the cell. Where contacting is effected in vitro, the factors may be added directly to the culture medium, as described herein. Alternatively, the factors may be contacted with an ES cell in vivo in a subject by introducing the factors into the subject (e.g., by introducing the factors into cells of the subject), or by administering the factors to the subject. The subject may be any embryonic or developed animal, but is preferably a mammal (e.g., a human, domestic animal, or commercial animal). More preferably, the subject is a human. Where the embryonic signalling factors are contacted with the ES cell in vivo, the subject is preferably an embryo. However, it is within the confines of the present invention for the ES cells to be transplanted into a fully-grown human or animal subject, and for the embryonic signalling factors then to be administered to the human in order to effect differentiation of the ES cells into differentiated neural cells in vivo in the subject.

The factors of the present invention may be contacted with an ES cell, either in vitro or in vivo in a subject, by known techniques used for the introduction and administration of proteins, nucleic acids, and other drugs, including, for example, injection and transfusion. When target ES cells are localized to a particular portion of a subject, it may be desirable to introduce the factors directly to the ES cells, by injection or by some other means (e.g., by introducing the factors into the blood or another body fluid).

Where the embryonic signalling factor is a protein or other molecule, it may be introduced into an ES cell directly, in accordance with conventional techniques and methods disclosed herein. Additionally, a protein embryonic signalling factor may be introduced into an ES cell indirectly, by introducing into the ES cell a nucleic acid encoding the factor, in a manner permitting expression of the protein inhibitor. The factor may be introduced into ES cells, in vitro or in vivo, using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of such viruses as retrovirus, HSV, adenovirus, adeno-associated virus, Semiliki Forest virus, cytomegalovirus, and vaccinia virus. The amount of nucleic acid to be used is an amount sufficient to express an amount of protein factor effective to produce a differentiated neural cell. These amounts may be readily determined by the skilled artisan. It is also within the confines of the present invention that a nucleic acid encoding a protein embryonic signalling factor may be introduced into suitable ES cells in vitro, using conventional procedures, to achieve expression of the protein factor in the ES cells. ES cells expressing protein embryonic signalling factor then may be introduced into a subject to produce a differentiated neural cell in vivo.

In accordance with the method of the present invention, embryonic signalling factors may be administered to a human or animal subject by known procedures, including, without limitation, oral administration, parenteral administration, and transdermal administration. Preferably, the factors are administered parenterally, by intracranial, intraspinal, intrathecal, or subcutaneous injection. The factors of the present invention also may be administered to a subject in accordance with any of the above-described methods for effecting in vivo contact between ES cells and embryonic signalling factors.

For oral administration, an embryonic signalling factor formulation may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), an embryonic signalling factor may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual.

For transdermal administration, an embryonic signalling factor may be combined with skin penetration enhancers, such as propylene glycol, polyethylene glycol, isopropanol, ethanol, oleic acid, N-methylpyrrolidone, and the like, which increase the permeability of the skin to the factor, and permit the factor to penetrate through the skin and into the bloodstream. The factor/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

The present invention provides a method for inducing differentiation of ES cells into differentiated neural cells (including spinal motor neurons), and for purifying and isolating the neural cells so generated using enhanced green fluorescent protein (eGFP) as a genetic marker. The method described herein for inducing differentiation of ES cells in vitro provides a source of neurons, or other neural cells of the CNS or PNS, that are available for transplant into a subject. Thus, this method is particularly useful for producing neural cells for use in treating conditions associated with nervous tissue degeneration.

The term "nervous tissue", as used herein, refers to tissue of the nervous system, which includes the differentiated neural cells of the present invention and progenitors thereof. As further used herein, "nervous tissue degeneration" means a condition of deterioration of nervous tissue, wherein the nervous tissue changes to a lower or less functionally-active form. It is believed that, by inducing differentiation of ES cells (e.g., into spinal motor neurons), the method described herein will be useful in repopulating various injured and/or degenerated nervous tissues (e.g., repopulation of a spinal cord) in a subject, through production of differentiated neural cells and subsequent transplant thereof into a subject in need of such transplantation.

Accordingly, the present invention provides a method for treating nervous tissue degeneration in a subject in need of treatment for nervous tissue degeneration, comprising inducing differentiation of ES cells into differentiated neural cells, in accordance with the methods described herein, and transplanting the differentiated neural cells into the subject, thereby treating the nervous tissue degeneration. By way of example, the method of the present invention may comprise the following steps: (a) obtaining or generating a culture of embryonic stem cells; (b) contacting the culture of embryonic stem cells with a rostralizing and/or caudalizing embryonic signalling factor, in an amount effective to produce neural progenitor cells; (c) contacting the neural progenitor cells with a dorsalizing or ventralizing embryonic signalling factor, in an amount effective to produce differentiated neural cells; (d) optionally, contacting the subclass of neural progenitor cells with at least one neurotrophic factor; and (e) transplanting the differentiated neural cells into the subject, in an amount effective to treat the nervous tissue degeneration. In one embodiment of the invention, the subject is an embryo. In another embodiment of the invention, the subject is a human. Preferably, the subject has nervous tissue degeneration.

Nervous tissue degeneration may arise in the central nervous system (CNS) or peripheral nervous system (PNS), and may be caused by, or associated with, a variety of disorders, conditions, and factors, including, without limitation, primary neurologic conditions (e.g., neurodegenerative diseases), CNS and PNS traumas and injuries, and acquired secondary effects of non-neural dysfunction (e.g., neural loss secondary to degenerative, pathologic, or traumatic events). Examples of CNS traumas include, without limitation, blunt trauma, hypoxia, and invasive trauma. Examples of acquired secondary effects of non-neural dysfunction include, without limitation, cerebral palsy, congenital hydrocephalus, muscular dystrophy, stroke, and vascular dementia, as well as neural degeneration resulting from any of the following: an injury associated with cerebral hemorrhage, developmental disorders (e.g., a defect of the brain, such as congenital hydrocephalus, or a defect of the spinal cord, such as spina bifida), diabetic encephalopathy, hypertensive encephalopathy, intracranial aneurysms, ischemia, kidney dysfunction, subarachnoid hemorrhage, trauma to the brain and spinal cord, treatment by such therapeutic agents as chemotherapy agents and antiviral agents, vascular lesions of the brain and spinal cord, and other diseases or conditions prone to result in nervous tissue degeneration.

In one embodiment of the present invention, the nervous tissue degeneration is a peripheral neuropathy in the PNS. As defined herein, the term "peripheral neuropathy" refers to a syndrome of sensory loss, muscle weakness, muscle atrophy, decreased deep-tendon reflexes, and/or vasomotor symptoms. In a subject who has a peripheral neuropathy, myelin sheaths (or Schwann cells) may be primarily affected, or axons may be primarily affected. The peripheral neuropathy may affect a single nerve (mononeuropathy), two or more nerves in separate areas (multiple mononeuropathy), or many nerves simultaneously (polyneuropathy).

Examples of peripheral neuropathies that may be treated by the methods disclosed herein include, without limitation, peripheral neuropathies associated with acute or chronic inflammatory polyneuropathy, amyotrophic lateral sclerosis (ALS), collagen vascular disorder (e.g., polyarteritis nodosa, rheumatoid arthritis, Sjögren's syndrome, or systemic lupus erythematosus), diphtheria, Guillain-Barré syndrome, hereditary peripheral neuropathy (e.g., Charcot-Marie-Tooth disease (including type I, type II, and all subtypes), hereditary motor and sensory neuropathy (types I, II, and III, and peroneal muscular atrophy), hereditary neuropathy with liability to pressure palsy (HNPP), infectious disease (e.g., acquired immune deficiency syndrome (AIDS)), Lyme disease (e.g., infection with *Borrelia burgdorferi*), invasion of a microorganism (e.g., leprosy—the leading cause of peripheral neuropathy worldwide, after neural trauma), leukodystrophy, metabolic disease or disorder (e.g., amyloidosis, diabetes mellitus, hypothyroidism, porphyria, sarcoidosis, or uremia), neurofibromatosis, nutritional deficiencies, paraneoplastic disease, peroneal nerve palsy, polio, porphyria, postpolio syndrome, Proteus syndrome, pressure paralysis (e.g., carpal tunnel syndrome), progressive bulbar palsy, radial nerve palsy, spinal muscular atrophy (SMA), a toxic agent (e.g., barbital, carbon monoxide, chlorobutanol, dapsone, emetine, heavy metals, hexobarbital, lead, nitrofurantoin, orthodinitrophenal, phenyloin, pyridoxine, sulfonamides, triorthocresyl phosphate, the vinca alkaloids, many solvents, other industrial poisons, and certain AIDS drugs (including didanosine and zalcitabine), trauma (including neural trauma—the leading cause of peripheral neuropathy, worldwide), and ulnar nerve palsy (Beers and Berkow, eds., *The Merck Manual of Diagnosis and Therapy*, $17^{th}$ ed. (Whitehouse Station, N.J.: Merck Research Laboratories, 1999) chap. 183). In a preferred embodiment of the present invention, the peripheral neuropathy is ALS or SMA.

In another embodiment of the present invention, the nervous tissue degeneration is a neurodegenerative disease. Examples of neurodegenerative diseases that may be treated by the methods disclosed herein include, without limitation, Alzheimer's disease, amyotrophic lateral sclerosis (Lou Gehrig's Disease), Binswanger's disease, Huntington's chorea, multiple sclerosis, myasthenia gravis, Parkinson's disease, and Pick's disease.

It is also within the confines of the present invention for the method described herein to be used to treat nervous tissue degeneration that is associated with a demyelinating condition. Examples of demyelinating conditions include, without limitation, acute disseminated encephalomyelitis (ADEM), acute transverse myelitis, acute viral encephalitis, adrenoleukodystrophy (ALD), adrenomyeloneuropathy, AIDS-vacuolar myelopathy, HTLV-associated myelopathy, Leber's hereditary optic atrophy, multiple sclerosis (MS), progressive multifocal leukoencephalopathy (PML), subacute sclerosing panencephalitis, and tropical spastic paraparesis.

The differentiated neural cells of the present invention may be transplanted into a subject in need of treatment by standard procedures known in the art and/or by methods described herein. By way of example, EBs (e.g., derived from pluripotent ES cells) may be induced with appropriate embryonic signalling factors (e.g., RA and Hh-Ag1.3), to produce differentiated neural cells. At an appropriate time post-induction (e.g., 3-4 days after induction), embryoid bodies (EBs) may be prepared for transplantation (e.g., partially triturated), and then transplanted into a subject (e.g., into the spinal cord of a chick, HH stage 15-17). To accommodate transplanted tissue, the subject may be suction-lesioned prior to implantation. Approximately ½-1 EB (or an EB equivalent) then may be implanted into a segment spanning 2-5 somites at rostral cervical, caudal cervical, thoracic, or lumbar regions of the subject.

In one embodiment of the present invention, the differentiated neural cell is transplanted into the spinal cord of a subject, thereby repopulating the subject's spinal cord, and the nervous tissue degeneration is a peripheral neuropathy associated with ALS or SMA. Where the transplanted neurons are spinal motor neurons, the rostralizing and caudalizing embryonic signalling factors are preferably retinoids (such as retinoic acid), and the dorsalizing or ventralizing embryonic signalling factor is preferably an activator of a hedgehog signalling pathway.

In the method of the present invention, differentiated neural cells are transplanted into a subject in need of treatment in an amount effective to treat the nervous tissue degeneration. As used herein, the phrase "effective to treat the nervous tissue degeneration" means effective to ameliorate or minimize the clinical impairment or symptoms of the nervous tissue degeneration. For example, where the nervous tissue degeneration is a peripheral neuropathy, the clinical impairment or symptoms of the peripheral neuropathy may be ameliorated or minimized by alleviating vasomotor symptoms, increasing deep-tendon reflexes, reducing muscle atrophy, restoring sensory function, and strengthening muscles. The amount of differentiated neural cells effective to treat nervous tissue degeneration in a subject in need of treatment will vary depending upon the particular factors of each case, including the type of nervous tissue degeneration, the stage of the nervous tissue degeneration, the subject's weight, the severity of the subject's condition, the type of differentiated neural cells, and the method of transplantation. This amount may be readily determined by the skilled artisan, based upon known procedures, including clinical trials, and methods disclosed herein.

In view of the above-described method for inducing differentiation of ES cells into differentiated neural cells, the present invention further provides a method for producing differentiated neural cells, comprising the steps of: (a) obtaining or generating a culture of ES cells; (b) contacting the culture of ES cells with a rostralizing and/or caudalizing embryonic signalling factor, in an amount effective to produce neural progenitor cells; (c) contacting the neural progenitor cells with a dorsalizing or ventralizing embryonic signalling factor, in an amount effective to produce a subclass of differentiated neural cells; and (d) optionally, contacting the differentiated neural cells with at least one neurotrophic factor. The present invention also provides a population of cells, comprising the differentiated neural cells produced by this method. In one embodiment, some or all of the cells express eGFP. Where the differentiated neural cells of the present invention are spinal motor neurons, the rostralizing and caudalizing embryonic signalling factors are preferably retinoids (such as retinoic acid), and the dorsalizing or ventralizing embryonic signalling factor is preferably an activator of a hedgehog signalling pathway.

In the method of the present invention, any of steps (b)-(d) may be performed in vitro, or in vivo in a subject. Following any in vitro steps, cells may be transplanted into a subject such that the remaining steps are performed in vivo. Accordingly, the method of the present invention further comprises the step of transplanting the neural progenitor cells or the differentiated neural cells into a subject. For example, a culture of ES cells may be contacted with a rostralizing and/or caudalizing embryonic signalling factor in vitro, to produce neural progenitor cells. The neural progenitor cells so produced then may be transplanted into a subject, such that steps (c) and (d) are carried out in vivo.

In an alternative method, a culture of ES cells may be contacted with a rostralizing and/or caudalizing embryonic signalling factor in vitro, to produce neural progenitor cells. The neural progenitor cells then may be contacted with a dorsalizing or ventralizing embryonic signalling factor in vitro, to produce differentiated neural cells. Thereafter, the differentiated neural cells may be transplanted into a subject, such that step (d) is performed in vivo.

In the further alternative, a culture of ES cells may be contacted with a rostralizing and/or caudalizing embryonic signalling factor in vitro, to produce neural progenitor cells; the neural progenitor cells may be contacted with a dorsalizing or ventralizing embryonic signalling factor in vitro, to produce differentiated neural cells; and, optionally, the differentiated neural cells may be contacted with at least one neurotrophic factor in vitro. The differentiated neural cells then may be transplanted into a subject. In one embodiment of the present invention, the neurons are transplanted into the spinal cord of the subject.

The present invention further provides a method for repopulating a spinal cord in a subject, comprising the steps of: (a) obtaining or generating a culture of ES cells; (b) contacting the culture of ES cells with a rostralizing and/or caudalizing embryonic signalling factor, in an amount effective to produce neural progenitor cells; (c) contacting the neural progenitor cells with a dorsalizing or ventralizing embryonic signalling factor, in an amount effective to produce differentiated neural cells; (d) optionally, contacting the differentiated neural cells with at least one neurotrophic factor; and (e) transplanting the differentiated neural cells into a spinal cord of the subject. The differentiated neural cells are transplanted into the spinal cord of the subject in an amount that is effective to repopulate the spinal cord. This amount may be readily determined by the skilled artisan, based upon known procedures and methods disclosed herein.

In a preferred embodiment of the present invention, the rostralizing and caudalizing embryonic signalling factors are retinoic acid, and the dorsalizing or ventralizing embryonic signalling factor is an activator of a hedgehog signalling pathway. This method of the present invention may be useful for treating subjects with nervous tissue degeneration, particularly peripheral neuropathies. Accordingly, in another embodiment of the present invention, the subject has a peripheral neuropathy. Preferably, the peripheral neuropathy is ALS or SMA. In yet another embodiment of the present invention, the transplanted differentiated neural cells express eGFP, thereby facilitating the monitoring of spinal cord repopulation.

The present invention further provides neural progenitor cells produced by a method comprising the steps of: (a) obtaining or generating a culture of ES cells; (b) contacting the culture of ES cells with a rostralizing and/or caudalizing embryonic signalling factor, in an amount effective to produce neural progenitor cells; and (c) optionally, contacting the neural progenitor cells with a dorsalizing or ventralizing embryonic signalling factor. In one embodiment of the present invention, the neural progenitor cells express enhanced green fluorescent protein (eGFP). Also provided are differentiated neural cells produced by a method comprising the steps of: (a) obtaining or generating a culture of embryonic stem cells; (b) contacting the culture of embryonic stem cells with a rostralizing and/or caudalizing embryonic signalling factor, in an amount effective to produce neural progenitor cells; (c) contacting the neural progenitor cells with a dorsalizing or ventralizing embryonic signalling factor, in an amount effective to produce differentiated neural cells; and (d) optionally, contacting the differentiated neural cells with at least one neurotrophic factor. In one embodiment of the invention, the differentiated neural cells express eGFP.

Because the selective degeneration of specific classes of CNS neurons underlies many neurological disorders, research into the growth, survival, and activity of neurons remains a priority. Unfortunately, however, live neurons are not readily available for such studies. For this reason, the present invention will be of particular importance to researchers in the fields of neuroscience and neurology, as it provides a potentially-unlimited source of neural cells to be studied. Accordingly, the present invention also provides for uses of the above-described neural progenitor cells and differentiated neural cells in particular areas of research.

The neural progenitor cells and differentiated neural cells of the present invention will be useful in the analysis of neuron (particularly, motor neuron) development, function, and death—research which is critical to a complete understanding of motor neuron disease. Furthermore, the neural progenitor cells and differentiated neural cells of the present invention will be useful in monitoring synaptic differentiation at sites of contact with target muscles. Finally, the neural progenitor cells and differentiated neural cells of the present invention will facilitate a direct comparison of normal, healthy motor neurons with degenerated motor neurons carrying one of the mutations detected in ALS or SMA patients (e.g., mutations in the superoxide dismutase (SOD) or survival motor neuron protein (SMN) genes). For such a comparison, both the healthy and the diseased neural cells may be produced using well-known techniques and methods described herein. Alternatively, cells carrying SOD or SMN mutations may be isolated from living or dead patients who have ALS or SMA.

As described herein, the inventors have constructed an ES-cell line from which living motor neurons could be identified by virtue of enhanced green fluorescent protein (eGFP) expression. A transgenic mouse line was generated in which an eGFP cDNA was expressed under the control of a 9-kB 5' region of the mouse HB9 gene that confers motor-neuron-specific transgene expression. Transgenic founder mice were screened by comparing the patterns of HB9 and eGFP expression. One mouse line, mHB9-Gfp1b, was found to express high levels of eGFP in the cell bodies of spinal motor neurons in E9.5-P10 mice, in a pattern that paralleled that of endogenous HB9. In addition, eGFP expression was detected at high levels in the axons and dendrites of motor neurons. An ES-cell line (HBG3) was derived from mHB9-Gfp1b transgenic mice; these cells transmitted the eGfp gene through the germ-line, and directed expression of eGFP in a similar motor-neuron-selective pattern.

Accordingly, the present invention further provides a transgenic non-human animal line containing embryonic stem (ES) cells for use in the methods of the present invention, wherein the ES cells express eGFP. Although the non-human animal may be any suitable animal (e.g., cat, cattle, dog, horse, goat, rodent, and sheep), it is preferably a rodent. More preferably, the non-human animal is a rat or a mouse. The transgenic non-human animal of the present invention may be produced by a variety of techniques for genetically engineering transgenic animals, including those known in the art. In one embodiment of the invention, the genome of the transgenic non-human animal comprises an enhanced green fluorescent protein (eGFP) gene. An animal line established from this transgenic animal would contain, in its embryos, ES cells expressing eGFP.

As used herein, the term "transgenic non-human animal" refers to a genetically-engineered non-human animal, produced by experimental manipulation, whose genome has been altered by introduction of a transgene. As further used herein, the term "transgene" refers to a nucleic acid molecule (e.g., DNA, a gene, or a fragment thereof) that has been introduced into the genome of an animal by experimental manipulation, wherein the introduced gene is not endogenous to the animal, or is a modified or mutated form of a gene that is endogenous to the animal. A modified or mutated form of an endogenous gene may be produced through human intervention (e.g., by introduction of a point mutation, introduction of a frameshift mutation, deletion of a portion or fragment of the endogenous gene, insertion of a selectable marker gene, insertion of a termination codon, etc.).

A transgenic non-human animal may be produced by several methods involving human intervention, including, without limitation, introduction of a transgene into an embryonic stem cell, newly-fertilized egg, or early embryo of a non-human animal; integration of a transgene into a chromosome of the somatic and/or germ cells of a non-human animal; and any methods described herein. In a preferred embodiment of the present invention, the transgenic non-human animal is produced by introduction of a transgene into an ES cell.

By way of example, the transgenic mouse line of the present invention may be established by pronucleus injection of a construct that uses a fragment (e.g., ~9 kB) comprising the 5' upstream region of the murine HB9 gene (Arber et al., Requirement for the homeobox gene Hb9 in the consolidation of motor neuron identity. *Neuron*, 23:659-764, 1999), followed by a 5' splice substrate (Choi et al., A generic intron increases gene expression in transgenic mice. *Mol. Cell Biol.*, 11:3070-74, 1991), an eGFP gene, and a bovine growth hormone polyadenylation signal. ES-cell lines then may be derived from mHB9-Gfp1b heterozygous blastocysts, as previously described (Abbondanzo et al., Derivation of embryonic stem cell lines. *Methods Enzymol.*, 225:803-23, 1993). A genetic line may be selected based upon its capacity to integrate into developing mouse blastocysts and its capacity for germline transmission. Embryonic stem cells then may be isolated from the transgenic animal, for use in the methods described herein.

In one embodiment of the present invention, the transgenic animal has a genome in which the superoxide dismutase (SOD) or survival motor neuron protein (SMN) gene is mutated (e.g., an SOD1-G93S mutation) or has been selectively inactivated, resulting in a disruption in its endogenous SOD or SMN gene. As used herein, a "disruption" refers to a mutation (i.e., a permanent, transmissable change in genetic material) in the SOD or SMN gene that prevents normal expression of functional SOD or SMN protein (e.g., it results in expression of a mutant SOD or SMN protein; it prevents expression of a normal amount of SOD or SMN protein; or it prevents expression of SOD or SMN protein). Examples of a disruption include, without limitation, a point mutation, introduction of a frameshift mutation, deletion of a portion or fragment of the endogenous gene, insertion of a selectable marker gene, and insertion of a termination codon. As used herein, the term "mutant" refers to a gene (or its gene product) which exhibits at least one modification in its sequence (or its functional properties) as compared with the wild-type gene (or its gene product). In contrast, the term "wild-type" refers to the characteristic genotype (or phenotype) for a particular gene (or its gene product), as found most frequently in its natural source (e.g., in a natural population). A wild-type animal, for example, expresses functional SOD or SMN protein.

Selective inactivation in the transgenic non-human animal of the present invention may be achieved by a variety of methods, and may result in either a heterozygous disruption (wherein one SOD allele or one SMN allele is disrupted, such that the resulting transgenic animal is heterozygous for the mutation) or a homozygous disruption (wherein both SOD or SMN alleles are disrupted, such that the resulting transgenic animal is homozygous for the mutation). In one embodiment of the present invention, the endogenous SOD or SMN gene of the transgenic animal is disrupted through homologous recombination with a nucleic acid sequence that encodes a region common to SOD or SMN gene products. By way of example, the disruption through homologous recombination may generate a knockout mutation in the SOD or SMN gene, particularly a knockout mutation wherein at least one deletion has been introduced into at least one exon of the SOD or SMN gene. Additionally, a disruption in the SOD or SMN gene may result from insertion of a heterologous selectable marker gene into the endogenous SOD or SMN gene.

One method for establishing a line of transgenic non-human animals expressing eGFP, and having a knockout mutation in the SOD or SMN gene, may comprise the following steps: (a) generating an SOD or SMN targeting vector; (b) introducing the targeting vector into a recipient cell of a non-human animal, to produce a treated recipient cell; (c) introducing the treated recipient cell into a blastocyst of a non-human animal, to produce a treated blastocyst; (d) introducing the treated blastocyst into a pseudopregnant non-human animal; (e) allowing the transplanted blastocyst to develop to term; (f) identifying a transgenic non-human animal whose genome comprises a knockout disruption in its endogenous SOD or SMN gene; (g) breeding the transgenic non-human animal to obtain a transgenic non-human animal exhibiting decreased expression of SOD or SMN protein relative to wild-type; and (h) crossing the transgenic non-human animal with a transgenic non-human animal whose genome contains an eGFP gene, in order to obtain a transgenic non-human animal expressing eGFP and exhibiting decreased expression of SOD or SMN protein relative to wild-type. A transgenic non-human animal expressing eGFP may be obtained in accordance with methods described above. It is also within the confines of the present invention to provide a transgenic non-human animal that overexpresses SOD or SMN polypeptide.

The eGFP-expressing transgenic animal lines of the present invention provide sources of ES cells and tissues for transplantations, chimeras, and double-marked recombination experiments. The transgenic animal line of the present invention also provide a genetic model of motor neuron degeneration. For example, where the genome of an animal from the transgenic animal line carries a mutation in its SOD gene, it may be used as a pharmacological model to screen for agents that may be useful in treating motor neuron degeneration, particularly ALS. While this model would exhibit a slow onset of degeneration, results are expected to be dramatic. Additionally, where the transgenic animal's genome carries a mutation in its SMN gene, it may be used as a pharmacological model to screen for agents that may be useful in treating motor neuron degeneration, particularly SMA. This model is expected to exhibit a quicker onset of degeneration.

ES cells derived from the transgenic non-human animal line of the present invention may be used in the methods described herein, including differentiation in vitro or in vivo, and reintroduction into a subject. Furthermore, ES cells derived from a transgenic animal line that expresses eGFP and ES cells derived from a transgenic animal line that carries a mutation in the SOD or SMN gene may be crossed. The behavior of mutant ES cells then may be followed by microscopic observation of developed animals or chimeric embryos in which cells and/or tissues express eGFP.

The present invention further provides a method for isolating a pure population of differentiated neural cells and/or purifying a population of differentiated neural cells, comprising the steps of: (a) obtaining or generating a culture of ES cells that express enhanced green fluorescent protein (eGFP); (b) contacting the culture of ES cells with a rostralizing and/or caudalizing embryonic signalling factor, in an amount effective to produce neural progenitor cells, wherein some or all of the neural progenitor cells also express eGFP; (c) contacting the neural progenitor cells with a dorsalizing or ventralizing embryonic signalling factor, in an amount effective to produce differentiated neural cells, wherein some or all of the differentiated neural cells also express eGFP; (d) optionally, contacting the differentiated neural cells with at least one neurotrophic factor; (e) detecting expression of eGFP in the differentiated neural cells; and (f) isolating the differentiated neural cells that express eGFP. In one embodiment of the invention, the differentiated neural cells are motor neurons. ES cells that express eGFP may be obtained from the transgenic animal of the present invention, as described above, or made in accordance with other methods disclosed herein.

According to the method of the present invention, expression of eGFP may be detected in differentiated neural cells by either in vitro or in vivo assay. As used herein, "expression" refers to the transcription of the eGFP gene into at least one mRNA transcript, or the translation of at least one mRNA into an eGFP protein. The differentiated neural cells may be assayed for eGFP expression by assaying for eGFP protein, eGFP cDNA, or eGFP mRNA. The appropriate form of eGFP will be apparent based on the particular techniques discussed herein.

Differentiated neural cells may be assayed for eGFP expression, and eGFP expression may be detected in differentiated neural cells, using assays and detection methods well known in the art. Because eGFP provides a non-invasive marker for labeling cells in culture and in vivo, expression of eGFP is preferably detected in differentiated neural cells using imaging techniques, particularly bright-field, phase, and fluorescence imaging techniques, as disclosed herein. Differentiated neural cells expressing high levels of eGFP then may be isolated from a cell suspension by sorting (e.g., by FACS sorting, using a Beckman-Coulter Altra flow cytometer), based upon their eGFP fluorescence and forward light scatter, as described below.

Other methods also may be used to detect eGFP expression in the differentiated neural cells of the present invention. Examples of such detection methods include, without limitation, hybridization analysis, imaging techniques, immunological techniques, immunoprecipitation, radiation detection, Western blot analysis, and any additional assays or detection methods disclosed herein. For example, differentiated neural cells may be assayed for eGFP expression using an agent reactive with eGFP protein or eGFP nucleic acid. As used herein, "reactive" means the agent has affinity for, binds to, or is directed against eGFP. As further used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. In one embodiment of the present invention, the agent reactive with eGFP is an antibody (e.g., αGFP (Molecular Probes, Inc., Eugene, Oreg.).

Following detection of eGFP expression in differentiated neural cells, the extent of eGFP expression in the cells may be measured or quantified, if desired, using one of various quantification assays. Such assays are well known to one of skill in the art, and may include immunohistochemistry, immunocytochemistry, flow cytometry, mass spectroscopy, Western blot analysis, or an ELISA for measuring amounts of eGFP protein.

The present invention further provides a method for identifying an agent for use in treating a condition associated with neuron (e.g., motor neuron) degeneration. As used herein, the term "neuron degeneration" means a condition of deterioration of neurons, wherein the neurons change to a lower or less functionally-active form. Examples of conditions associated with neuron degeneration include peripheral neuropathies, demyelinating conditions, and the primary neurologic conditions (e.g., neurodegenerative diseases), CNS and PNS traumas and injuries, and acquired secondary effects of non-neural dysfunction (e.g., neural loss secondary to degenerative, pathologic, or traumatic events) described herein.

The method of the present invention comprises the steps of: (a) obtaining or generating a culture of embryonic stem cells; (b) contacting the culture of embryonic stem cells with an amount of a retinoid (such as retinoic acid) effective to produce neural progenitor cells; (c) activating a hedgehog signalling pathway in the neural progenitor cells, to produce neurons, wherein some or all of the neurons are degenerated; (d) contacting the degenerated neurons with a candidate agent; and (e) determining if the agent enhances regeneration of some or all of the degenerated neurons. As used herein, the term "enhance regeneration" means augment, improve, or increase partial or full growth (or regrowth) of a neuron (including neurites and the myelin sheath) that has degenerated. As further used herein, the term "growth" refers to an increase in diameter, length, mass, and/or thickness of a neuron (including neurites and the myelin sheath). Regeneration of the neuron may take place in neurons of both the central nervous system and the peripheral nervous system. In one embodiment of the present invention, the agent enhances regeneration of degenerated motor neurons.

In the method of the present invention, degenerated neurons may be contacted with a candidate agent by any of the methods of effecting contact between factors (or agents) and cells, and any modes of introduction and administration, described herein. Regeneration, and enhanced regeneration, of neurons may be measured or detected by known procedures, including Western blotting for myelin-specific and axon-specific proteins, electron microscopy in conjunction with morphometry, and any of the methods, molecular procedures, and assays known to one of skill in the art. In addition, growth of myelin may be assayed using the g-ratio—one measure of the integrity of the axon:myelin association. The g-ratio is defined as the axonal diameter divided by the total diameter of the axon and myelin. This ratio provides a reliable measure of relative myelination for an axon of any given size (Bieri et al., Abnormal nerve conduction studies in mice expressing a mutant form of the POU transcription factor, SCIP. *J. Neurosci. Res.*, 50:821-28, 1997). Numerous studies have documented that a g-ratio of 0.6 is normal for most fibers (Waxman and Bennett, Relative conduction velocities of small myelinated and nonmyelinated fibres in the central nervous system. *Nature New Biol.*, 238:217, 1972).

In one embodiment of the present invention, genomic DNA in the degenerated neurons carries a mutation in an SOD or SMN gene. Such degenerated neurons may be isolated, for example, from a transgenic animal of the present invention, as described above, whose genome contains a mutated SOD or SMN gene. In another embodiment of the invention, the degenerated neurons express enhanced green fluorescent protein (eGFP). Such degenerated neurons may be isolated, for example, from a transgenic animal of the present invention, as described above, whose genome contains an eGFP gene. Degenerated neurons expressing both SOD and eGFP, or expressing both SMN and eGFP, may be produced by crossing ES cells containing an SOD or SMN mutation with ES cells containing an eGFP gene. It is expected that such neurons would allow for increased high-throughput drug screening.

Based upon the foregoing, the present invention also provides systems and methods for use in screening for, and identifying, modulators of neural differentiation. As used herein, a "modulator of neural differentiation" may be any agent or combination of agents that that has an antagonistic (inhibitory) or agonistic (facilitatory) effect on neural differentiation, including the neural differentiation of embryonic stem cells, embryoid bodies, neural progenitor cells, other early-stage neural cells, or any other starting material capable of differentiating into a neural cell, into partially-differentiated neural cells, fully-differentiated neural cells, and other later-stage neural cells. Thus, a modulator of differentiation may be an agonist or an antagonist. The modulators of the present invention, including any now known or later discovered, also may be natural or synthetic.

As further used herein, the term "agent" includes any protein, polypeptide, peptide, nucleic acid (including DNA or RNA), antibody, Fab fragment, F(ab')$_2$ fragment, molecule, compound, antibiotic, or drug, or any combination thereof. A Fab fragment is a univalent, antigen-binding fragment of an antibody, which is produced by papain digestion. An F(ab')$_2$ fragment is a divalent antigen-binding fragment of an antibody, which is produced by pepsin digestion.

It is expected that the modulators of the present invention will be useful in all of the inventive methods described above, including methods of inducing differentiation, methods of producing differentiated neural cells, methods for repopulating a spinal cord, and methods for treating nervous tissue degeneration. By way of example, agonists of expand differentiation would be particularly useful in facilitating differentiation of ES cells into differentiated neural cells. Such modulators are expected to increase the rate at which, and the efficiency with which, the above-described methods proceed to completion. For instance, as discussed below, the inventors have shown that the generation of motor neurons in EBs depends on both the caudalizing action of RA and the ventralizing action of Hh signals; the inventors have also shown that the efficiency of motor-neuron generation can be enhanced by elevating the level of Hh signalling in RA-exposed EBs. Therefore, agonists of differentiation of the present invention will be beneficial, in that they will decrease the time otherwise required to induce differentiation, to produce differentiated neural cells, to repopulate a spinal cord, or to treat nervous tissue degeneration in accordance with the methods described above.

Additionally, by way of example, antagonists of differentiation would be particularly useful in treating conditions associated with cell proliferation, including defects in cell proliferation (such as hyperplasia and neoplasia). As used herein, "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis. Because the antagonistic modulators of the present invention are expected to downregulate oncogenes and inhibit the proliferation of cells in a neoplasm, they will provide novel therapies for treating cancer.

When referring to the effect of the modulator on neural differentiation, the terms "inhibitory" and "facilitatory" encompass at least a small, but measurable, decrease or increase, respectively, in the rate of differentiation. In preferred embodiments, the rate of neural differentiation (e.g., differentiation of ES cells into differentiated neural cells) is decreased/increased by at least 20% over non-treated controls; in more preferred embodiments, the decrease/increase is at least 50%; in still more preferred embodiments, the decrease/increase is at least 70%; and in the most preferred embodiments, the decrease/increase is at least 80%. Preferably, the modulator of differentiation is facilitatory.

By way of example, the present invention provides an in vitro system for use in identifying a modulator of neural differentiation (e.g., differentiation of an embryonic stem cell into a differentiated neural cell), and a modulator identified by this system. The in vitro system of the present invention comprises: (a) embryonic stem cells (e.g., a frozen or thawed preparation, collection, or culture thereof); (b) a rostralizing or caudalizing embryonic signalling factor; and (c) optionally, a dorsalizing or ventralizing embryonic signalling factor. In one embodiment, the embryonic stem cells are murine embryonic stem cells. In another embodiment, the embryonic stem cells are human embryonic stem cells.

As described above, examples of rostralizing embryonic signalling factors include a retinoid (e.g., retinoic acid) and Wnt; examples of caudalizing embryonic signalling factors include a retinoid (e.g., retinoic acid) and Wnt; examples of dorsalizing embryonic signalling factors include BMP and Wnt; and examples of ventralizing embryonic signalling factors include activators of a hedgehog signalling pathway (e.g., a hedgehog protein or an agonist of hedgehog signalling, including SHh, Hh-Ag1.3, Frizzled 8, and mFrz8CRD). In certain cases, of course, the embryonic signalling factor may have numerous effects on the differentiation of ES cells. For example, retinoids and Wnt have been shown to have rostralizing and caudalizing effects; Wnt also has dorsalizing effects.

In one embodiment of the present invention, the components of the in vitro system are assembled in a kit, in which each component of the system is separately packaged. In another embodiment, some or all of the components of the in vitro system are in contact with one another. For example, the embryonic stem cells of the in vitro system may be brought into contact with a rostralizing or caudalizing embryonic signalling factor, to produce a neural progenitor cell. These neural progenitor cells may then be contacted with a dorsalizing or ventralizing embryonic signalling factor, to produce differentiated neural cells.

The in vitro system of the present invention may also comprise additional factors. For example, in one embodiment, the in vitro system further comprises at least one neurotrophic factor. In another embodiment, the in vitro system further comprises at least one conditioned medium. Examples of conditioned media for use in the present invention include, without limitation, Wnt3a conditioned medium and mFrz8CRD conditioned medium.

The present invention further provides a method for identifying a modulator of neural differentiation of embryonic stem cells (e.g., differentiation of an embryonic stem cell into a differentiated neural cell), comprising the steps of: (a) contacting an in vitro system with a candidate modulator; and (b) determining if the candidate modulator has an effect on neural differentiation of embryonic stem cells, wherein the in vitro system comprises: (a) embryonic stem cells (e.g., a preparation, collection, or culture thereof); (b) a rostralizing or caudalizing embryonic signalling factor; and (c) optionally, a dorsalizing or ventralizing embryonic signalling factor. Also provided is a modulator identified by this method. In accordance with this method of the present invention, the ES cells of the in vitro system are first grown to a desirable stage, and then brought into contact with the other components of the in vitro system (e.g., the rostralizing, caudalizing, dorsalizing, and/or ventralizing embryonic signalling factors), prior to, or concurrent with, the time when contact between the in vitro system and the candidate modulator is effected. The skilled artisan can determine whether any particular candidate is a modulator of ES-cell differentiation by any of several well-known methods, including comparison with non-treated controls.

The present invention also provides an in vitro system for use in identifying a modulator of neural differentiation (e.g., differentiation of an embryonic stem cell into a differentiated neural cell), and a modulator identified by this system. The in vitro system of the present invention comprises embryonic stem cells (e.g., a preparation, collection, or culture thereof) that have been contacted with: (a) a rostralizing or caudalizing embryonic signalling factor, to produce a collection of neural progenitor cells; and (b) optionally, a dorsalizing or ventralizing embryonic signalling factor. The factor in step (a) and the factor in step (b) may be contacted with the embryonic stem cells either simultaneously, or one after the other. In one embodiment, the in vitro system further comprises at least one neurotrophic factor. In another embodiment, the in vitro system further comprises at least one conditioned medium.

As discussed above, the embryonic stem cells in the in vitro system may, in certain embodiments, be murine embryonic stem cells or human embryonic stem cells. In one embodiment of the present invention, the neural progenitor cells are selected from the group consisting of progenitor cells of DRG neurons, progenitor cells of motor neurons, progenitor cells of peripheral neurons, progenitor cells of spinal cord neurons, and progenitor cells of ventral interneurons. In another embodiment, the neural progenitor cells differentiate into repositioned neural progenitor cells or fully-differentiated neural cells. Examples of fully-differentiated neural cells include, without limitation, astrocytes, neurons (e.g., motor neurons, including spinal motor neurons and other post-mitotic motor neurons), oligodendrocytes, and Schwann cells.

In addition, the present invention provides a method for identifying a modulator of neural differentiation of neural progenitor cells (e.g., differentiation of a neural progenitor cell into a fully-differentiated neural cell), comprising the steps of: (a) contacting an in vitro system with a candidate modulator; and (b) determining if the candidate modulator has an effect on neural differentiation of neural progenitor cells, wherein the in vitro system comprises embryonic stem cells (e.g., a preparation, collection, or culture thereof) that has been contacted with: (a) a rostralizing or caudalizing embryonic signalling factor, to produce a collection of neural progenitor cells; and (b) optionally, a dorsalizing or ventralizing embryonic signalling factor. Also provided is a modulator identified by this method.

In accordance with this method of the present invention, the neural progenitor cells of the in vitro system are first grown to a desirable stage, and then brought into contact with the other components of the in vitro system (e.g., the dorsalizing and/or ventralizing embryonic signalling factors), prior to, or concurrent with, the time when contact between the in vitro system and the candidate modulator is effected. In one embodiment of the present invention, the neural progenitor cells in the system differentiate into repositioned neural progenitor cells or fully-differentiated neural cells. The skilled artisan can determine whether any particular candidate is a modulator of neural-progenitor-cell differentiation by any of several well-known methods, including comparison with non-treated controls.

The present invention further provides a method for identifying a modulator of neural differentiation (e.g., differentiation of an embryonic stem cell into a differentiated neural cell), comprising the steps of: (a) obtaining or generating a collection of embryonic stem cells; (b) contacting the embryonic stem cells simultaneously with a rostralizing or caudalizing embryonic signalling factor and a dorsalizing or ventralizing embryonic signalling factor, in the presence of a candidate modulator; and (c) determining if the candidate modulator modulates neural differentiation of the embryonic stem cells. Also provided is a modulator identified by this method. In certain embodiments, the embryonic stem cells may be murine embryonic stem cells or human embryonic stem cells.

The skilled artisan can determine whether any particular candidate is a modulator of ES-cell differentiation by any of several well-known methods. By way of example, the determination in step (c) may be made by comparing neural differentiation (e.g., the rate of neural differentiation) of the embryonic stem cells in step (b) with neural differentiation (e.g., the rate of neural differentiation) of a second collection of embryonic stem cells that have been contacted with a rostralizing or caudalizing embryonic signalling factor, and a dorsalizing or ventralizing embryonic signalling factor, in the absence of the candidate modulator. In one embodiment of the present invention, the embryonic stem cells in step (b) are contacted with the rostralizing or caudalizing embryonic signalling factor prior to contact with the dorsalizing or ventralizing embryonic signalling factor. The method of the present invention may further comprise the step of contacting the embryonic stem cells in step (b) with at least one neurotrophic factor. The method of the present invention may also further comprise the step of contacting the embryonic stem cells in step (b) with at least one conditioned medium.

The present invention further provides a method for identifying a modulator of neural differentiation (e.g., differentiation of an embryonic stem cell into a differentiated neural cell), comprising the steps of: (a) obtaining or generating a first collection of embryonic stem cells and a second collection of embryonic stem cells; (b) contacting the first collection of embryonic stem cells with a rostralizing or caudalizing embryonic signalling factor and a dorsalizing or ventralizing embryonic signalling factor, in the presence of a candidate modulator; (c) contacting the second collection of embryonic stem cells with a rostralizing or caudalizing embryonic signalling factor and a dorsalizing or ventralizing embryonic signalling factor, in the absence of the candidate modulator; and (d) determining if the candidate modulator in step (b) modulates neural differentiation of embryonic stem cells by comparing neural differentiation (e.g., the rate thereof) of the embryonic stem cells in step (b) with neural differentiation (e.g., the rate thereof) of the embryonic stem cells in step (c). Also provided is a modulator identified by this method.

Additionally, the present invention provides a method for identifying a modulator of neural differentiation (e.g., differentiation of an embryonic stem cell into a differentiated neural cell), comprising the steps of: (a) obtaining or generating a collection of embryonic stem cells; (b) contacting the collection of embryonic stem cells with an amount of a rostralizing or caudalizing embryonic signalling factor effective to produce neural progenitor cells; (c) contacting the neural progenitor cells with a dorsalizing or ventralizing embryonic signalling factor, in the presence of a candidate modulator; and (d) determining if the candidate modulator modulates neural differentiation of the embryonic stem cells. In some embodiments of the present invention, the embryonic stem cells differentiate into fully-differentiated neural cells. Examples of such fully-differentiated neural cells include, without limitation, astrocytes, neurons, oligodendrocytes, and Schwann cells.

The present invention further provides a method for identifying a modulator of a Wnt signalling pathway. Also provided is a modulator (agonist or antagonist) identified by this method. As used herein, "Wnt" refers to any member of the Wnt family of proteins now known or later discovered, including, without limitation, Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9B, Wnt9A, Wnt10B, Wnt10A, Wnt11, Wnt14, Wnt15, and Wnt16. As further used herein, "Wnt signalling pathway" refers to the cascade of biochemical signalling that includes, is initiated by, or directly or indirectly results from release of a Wnt protein, particularly signalling that relates to direction or position of cells in an embryo during development and differentiation. Additionally, as used herein, a "modulator of a Wnt signalling pathway" may be any agent or combination of agents that has an antagonistic (inhibitory) or agonistic (facilitatory) effect on a Wnt signalling pathway.

The Wnt family is composed of approximately 20 glycosylated, highly-conserved, secreted extracellular signalling molecules that have corresponding receptors and antagonists. Wnt proteins regulate cell-to-cell interactions during embryogenesis; Wnt genes and Wnt signalling have also been implicated in cancer. Wnt signalling plays an important role in embryonic development; it causes tumorigenesis when aberrantly activated, and may also be involved in angiogenesis. Wnt signalling proceeds through at least two pathways: the well-understood canonical (Wnt/beta-catenin) pathway and the more recently discovered non-canonical (Wnt/calcium) pathway. Some Wnt proteins signal through the canonical pathway alone; others signal through both pathways. Each Wnt ligand activates a unique set of target genes that mediate a specific biological response. As currently understood, Wnt proteins bind to receptors of the Frizzled family on the cell surface. Through several cytoplasmic relay components, the signal is transduced to beta-catenin, which then enters the nucleus and forms a complex with TCF, thereby activating transcription of Wnt target genes.

Relevant genes involved in Wnt signalling may be classified according to function as follows: ligand, receptors, and related molecules (DKK1, DKK2, DKK3, DKK4, FRZB (FRP-3), FZD1, FZD2, FZD3, FZD4, FZD5, FZD6, FZD7, FZD8, FZD9, FZD10, LRP5, LRP6, PPN, SFRP2 (FRP-2), SFRP4 (FRP-4), SMOH, WIF1, WNT1, WNT2, WNT2B, WNT3, WNT3A, WNT4, WNT5A, WNT5B, WNT6, WNT7A, WNT7B, WNT8A, WNT10A, WNT11, WNT14, WNT15, and WNT16); intracellular molecules (AES (TLE/groucho), APC, AXIN1, AXIN2, BTRC (b-TrCP), CTBP1, CTBP2, CTNNB1 (b-catenin), CTNNBIP1 (ICAT), DVL2, EP300, FRAT1, FRAT2, GSK3A (GSKalpha), GSK3B (GSKbeta), LEF1, NKD1, NKD2, PPP2R5D (B56 PP2A), SOX17, TCF-3, TCF4, and TCF7 (Tcf-1)); target genes in the canonical (Wnt/b-catenin) pathway (transcription factors, including CDX1, EP300, FOSL1 (Fra-1), ID2, ID3, JUN, MSX1, MSX2, MYC, PITX2, T (brachyury), and TCF7 (Tcf-1); cell-cycle proteins, including CCND1, CCND2, and CCND3; growth factors, including BMP4, FGF4, GAS (gastrin), VEGF, WISP1, WISP2, and WISP3; extracellular proteins, including CLDN1 (claudin-1), FST (follistatin), GJAI (connexin43), MMP7, MMP26, and SFRP2; receptors, including CD44, EFNB1 (ephrinB1), FZD1, PLAUR (uPAR), and RET; intracellular signaling molecules, including AES (TLE/groucho) and AXIN2; and enzymes, including ENPP2 (autotaxin) and PTGS2 (Cox-2); and target genes in the non-canonical (Wnt/Ca2+ pathway) (COL1A1, EGR1, ICAM1, MYC, NOS2A (iNOS), PTGS2 (Cox-2), and VEGF).

Wnt signalling is discussed in the following reviews, the contents of which are hereby incorporated by reference herein: Cadigan and Nusse, Wnt signaling: a common theme in animal development. 11 (24):3286-305, 1997; van Es et al., You Wnt some, you lose some: oncogenes in the Wnt signaling pathway. *Curr. Opin. Genet. Dev.*, 13(1):28-33, 2003; Giles et al., Caught up in a Wnt storm: Wnt signaling in cancer. *Biochim. Biophys. Acta.*, 1653(1):1-24, 2003; van Gijn et al., The Wnt-frizzled cascade in cardiovascular disease. *Cardiovasc. Res.*, 1: 16-24, 2002; Goodwin and D'Amore, Wnt signaling in the vasculature. *Angiogenesis*, 5(1-2):1-9, 2002; Hatsell et al., Beta-catenin and Tcfs in mammary development and cancer. *J. Mammary Gland Biol. Neoplasia.*, 8:145-58, 2003; Imondi and Thomas, Neuroscience: the ups and downs of Wnt signaling. Science, 302: 1903-04, 2003; Katoh, M., Genome-wide search of human genes implicated in WNT signaling pathway using bioinformatics. *Genome Informatics*, 13:367-68, 2002; Malbon et al., Wnt signaling and heterotrimeric G-proteins: strange bedfellows or a classic romance? *Biochem. Biophys. Res. Commun.*, 287(3):589-93, 2001; Moon et al., The promise and perils of Wnt signaling through beta-catenin. *Science*, 296(5573): 1644-46, 2002; Nusse, R., Wnts and hedgehogs: lipid-modified proteins and similarities in signaling mechanisms at the cell surface. *Development*, 130(22):5297-305, 2003; Pandur et al., Increasingly complex: new players enter the Wnt signaling network. *Bioessays*, 24(10):881-84, 2002; Postigo, A. A., Opposing functions of ZEB proteins in the regulation of the TGF/BMP signaling pathway. *EMBO J.*, 22:2443-52, 2003; Povelones and Nusse, Wnt signalling sees spots. *Nat. Cell Biol.*, 4(11):E249-50, 2002; Veeman et al., A second canon: functions and mechanisms of beta-catenin-independent Wnt signaling. *Dev. Cell*, 5(3):367-77, 2003; and Wodarz and Nusse, Mechanisms of Wnt signaling in development. *Annu. Rev. Cell Dev. Biol.*, 14:59-88, 1998.

The method of the present invention comprises the steps of: (a) obtaining or generating a first collection of cells selected from the group consisting of embryonic stem cells (e.g., murine embryonic stem cells or human embryonic stem cells), embryoid bodies, and neural progenitor cells; (b) obtaining or generating a second collection of cells selected from the same group as the cells selected in step (a); (c) contacting the first collection of cells with a candidate modulator, in the presence of an activator of a Wnt signalling pathway; (d) contacting the second collection of cells with an activator of a Wnt signalling pathway; and (e) determining if the candidate modulator in step (b) modulates neural differentiation, wherein modulation of neural differentiation is indicative of modulation of a Wnt signalling pathway. By way of example, the modulating effect, if any, of the candidate modulator may be determined by comparing neural differentiation (e.g., the rate thereof) of the cells in step (b) with neural differentiation (e.g., the rate thereof) of the cells in step (c).

As used herein, an "activator" of a Wnt signalling pathway includes any factor, now known or later discovered, that effects, increases, induces, initiates, or stimulates release of a Wnt protein; a factor that effects or produces biochemical signalling within a Wnt signalling pathway; and a factor that increases, induces, initiates, or stimulates signalling within a Wnt signalling pathway. For example, the activator of Wnt signalling may be a Wnt protein (e.g., Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9B, Wnt9A, Wnt10B, Wnt10A, Wnt11, Wnt14, Wnt15, and Wnt16), a Wnt receptor, or an agonist of a Wnt signalling pathway. An "agonist" of a Wnt signalling pathway, as used herein, is a factor that has affinity for, and stimulates physiologic activity at, cell receptors normally stimulated by naturally-occurring substances, such that signalling in a Wnt signalling pathway within the cell is increased, initiated, stimulated, or induced.

In accordance with the method of the present invention, the cells in step (a) may differentiate into repositioned neural progenitor cells or fully-differentiated neural cells. In one embodiment, the fully-differentiated neural cells are motor neurons. In another embodiment, the cells in step (a) and step (b) are neural progenitor cells of a forebrain/midbrain character, and the cells in step (a) differentiate into repositioned neural progenitor cells of a caudalized character. In yet another embodiment of the present invention, the neural progenitor cells in step (a) and step (b) are generated from embryonic stem cells. In one embodiment, the embryonic stem cells are mouse embryonic stem cells. In another embodiment, the embryonic stem cells are human embryonic stem cells.

Examples of the activator of a Wnt signalling pathway include, without limitation, AES (TLE/groucho), adenomatous polyposis coli (APC), ARHU, ARHV, AXIN1, AXIN2, BMP4, BTRC (b-TrCP), CCND1, CCND2, CCND3, CD44, CDX1, CLDN1 (claudin-1), COL1A1, CTBP1, CTBP2, CTNNB1 (B-catenin), CTNNBIP1 (ICAT), DKK1, DKK2, DKK3, DKK4, Dsh, DVL2, EGR1, EFNB1 (ephrinB1), ENPP2 (autotaxin), EP300, FBXW1B, FGF4, FOSL1 (Fra-1), FRAT1, FRAT2, FRZB (FRP-3), FST (follistatin), FZD1, FZD2, FZD3, FZD4, FZD5, FZD6, FZD7, FZD8, FZD9, FZD10, GAS (gastrin), GIPC2, GIPC3, GJA1 (connexin43), GSK3A, glycogen synthase kinase-3β(GSK-3B), ICAM1, ID2, ID3, JUN, LEF1, LRP5, LRP6, MFRP, MMP7, MMP26, MSX1, MSX2, MYC, NKD1, NKD2, NOS2A (iNOS), PITX2, PLAUR (uPAR), serine/threonine protein phosphatase 2A (PP2A), PPN, PPP2R5D (B56 PP2A), PTGS2 (Cox 2), RET, SFRP2 (FRP-2), SFRP4 (FRP-4), SMOH, SOX17, T (brachyury), a TCF protein (e.g., TCF-3, TCF4, and TCF7 (Tcf-1)), VANGL1, VEGF, WIF1, WISP1, WISP2, WISP3, a Wnt protein (e.g., Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9B, Wnt9A, Wnt10B, Wnt10A, Wnt11, Wnt14, Wnt15, and Wnt16), a Wnt receptor, and any analogue or homologue thereof. In one embodiment of the present invention, the candidate modulator enhances neural differentiation.

The present invention also provides a method for identifying a modulator of neural differentiation. This method comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a) (i.e., where embryonic stem cells are selected in (a), embryonic stem cells are also selected in (b); where embryoid bodies are selected in (a), embryoid bodies are also selected in (b); and where neural progenitor cells are selected in (a), neural progenitor cells are also selected in (b)); (c) contacting the first collection of cells with a candidate modulator, in the presence of an activator of a Wnt signalling pathway; (d) contacting the second collection of cells with an activator of a Wnt signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c). Also provided is a modulator identified by this method.

Additionally, the present invention provides a method for identifying a modulator of Wnt-dependent neural differentiation, comprising the steps of: (a) obtaining or generating a collection of cells selected from the group consisting of embryonic stem cells, embryoid bodies, and neural progenitor cells; (b) contacting the collection of cells with a candidate modulator; and (c) determining if the candidate modulator modulates Wnt-dependent neural differentiation of the cells in the collection. Also provided is a modulator identified by this method. As used herein, a "modulator of Wnt-dependent neural differentiation" may be any agent or combination of agents that has an antagonistic (inhibitory) or agonistic (facilitatory) effect on Wnt-dependent neural differentiation. Wnt-dependent neural differentiation, and any modulation thereof, may be detected using techniques and assays well known in the art, including those described herein. In one embodiment of the present invention, the collection of cells in step (b) is further contacted with the candidate modulator in the presence of an activator of a Wnt signalling pathway.

The present invention further provides a method for identifying a modulator of a BMP signalling pathway. Also provided is a modulator (agonist or antagonist) identified by this method. As used herein, "BMP" refers to any member of the BMP family of proteins now known or later discovered, including, without limitation, BMP1, BMP2, BMP2b, BMP3 (ADMP), BMP4, BMP5, BMP6, BMP7, BMP8, BMP9, BMP10, BMP11, and BMPI 15. As further used herein, "BMP signalling pathway" refers to the cascade of biochemical signalling that includes, is initiated by, or directly or indirectly results from release of a BMP protein, particularly signalling that relates to direction or position of cells in an embryo during development and differentiation. Additionally, as used herein, a "modulator of a BMP signalling pathway" may be any agent or combination of agents that has an antagonistic (inhibitory) or agonistic (facilitatory) effect on a BMP signalling pathway.

Bone morphogenetic proteins (BMPs) are members of the transforming growth factor-β (TGB-β) superfamily that regulates a variety of biological responses during embryonic development and post-natal life. The TGF-β superfamily of cytokines influences a diverse range of normal cellular processes, including cell adhesion, cell proliferation, apoptosis, and secretion of extracellular matrix molecules. Additionally, they are key molecules in many developmental processes, including body-plan determination in embryos and organ morphogenesis in adults. Alteration of the TGB-β/BMP signalling pathway has been linked to various disease processes, including developmental abnormalities and cancer progression.

BMPs exert their effects by binding to two types of serine/threonine kinase BMP receptors. In particular, signals elicited by BMPs, and by other ligands of the TGF-beta superfamily, are generated after the formation of heteromeric receptor complexes consisting of type I and type II receptors. The type II receptor phosphorylates the type I receptor, thereby activating the type I receptor kinase. Activation of the type I receptor kinases leads to phosphorylation and translocation to the nucleus of intracellular signalling molecules (including Smad1, Smad5, and Smad8), as part of the canonical BMP signalling pathway. The phosphorylated Smad proteins form a multimeric complex that translocates to the nucleus and activates transcription—either through interaction with DNA binding proteins or through direct DNA binding. BMP effects are also mediated by activation of the mitogen-activated protein (MAP) kinase pathway, as part of the non-canonical BMP signalling pathway. TAK1, a member of the MAP kinase family, and its activator, TAB1, participate in the BMP signalling pathway.

BMP activity is highly regulated by diffusible BMP antagonists that prevent BMP interactions with BMP receptors, thereby modulating BMP effects in tissues. For example, extracellular signalling by BMPs is regulated by a number of secreted proteins, including such BMP-binding factors as chordin, noggin, follistatin, gremlin, and cerberus, and by upstream molecules that regulate chordin function, including twisted gastrulation and tolloid. Additionally, intracellular regulators of BMP signalling have been identified, including inhibitory Smads, BAMBI, Smurf1, and a number of nuclear proteins, such as Tob and OAZ.

Relevant genes involved in BMP signalling may be classified according to function as follows: TGB-β superfamily cytokines, including TGB-β (TGB-β1, TGB-β2, and TGB-β3), BMP and GDF (AMH, BMP1, BMP2, BMP3, BMP4, BMP5, BMP6, BMP7, BMP8, BMP10, BMP15, GDF1, GDF2 (BMP9), GDF3 (Vgr-2), GDF5 (CDMP-1), GDF8, GDF9, GDF10, and GDF11 (BMP11)), and activin (EBAF (leftyA), INHA (inhibin a), INHBA (inhibin BA), INHBB (inhibin BB), INHBC (inhibin BC), LEFTB (leftyB), and nodal); receptors, including ACVR1 (ALK2), ACVR1 B (ALK4), ACVR2, ACVR2B, ACVRL1 (ALK1), AMHR2, BMPR1A (ALK3), BMPR1B (ALK6), BMPR2, TGFBR2, TGFBR1 (ALK5), and TGFBR3; Smads, including MADH1

(smad1), MADH2 (smad2), MADH3 (smad3), MADH4 (smad4), MADH5 (smad5), MADH6 (smad6), MADH7 (smad7), and MADH9 (smad9); Smad target genes, including TGB-β/activin responsive genes (CDC25A, CDKN1A (p21Waf1/p21Cip1), CDKN2B (p15Ink2b), COL1A1, COL1A2, COL3A1, FOS, IGF1, IGFBP3, IL6, ITGB5 (integrin b5), ITGB7 (integrin b7), IVL (involucrin), JUN, JUNB, MYC, goosecoid, PDGFB, SERPINE1 (PAI-1), SNC73 (IgA), TGFB1I1, TGFB1, TGIF, TIMP1, TSC22), and BMP responsive genes (TCF8 (AREB6), BGLAP (osteocalcin), DLX2, ID1, ID2, ID3, ID4, JUNB, MADH6 (Smad6), STAT1, and SOX4); and molecules regulating signaling of TGB-B superfamily, including CER1 (cerberus), CHRD (chordin), CKTSF1B1 (gremlin), ENG (endoglin), EVI1 (Evi-1), FKBP1B, FST (follistatin), NBL1 (DAN), NMA, PLAU (uPA), RUNX1 (AML1), RUNX2, and TDGF1.

BMP signalling is discussed in the following reviews, the contents of which are hereby incorporated by reference herein: Botchkarev, V. A., Bone morphogenetic proteins and their antagonists in skin and hair follicle biology. *Journal of Investigative Dermatology*, 120:36-47, 2003; Massague et al., TGFb signaling in growth control, cancer, and heritable disorders. *Cell*, 103:295-309, 2000; Miyazono et al., Divergence and convergence of TGF-beta/BMP signaling. *J. Cell Physiol.*, 187 (3):265-76, 2001; Miyazono, K., Positive and negative regulation of TGF-beta signaling, *J. Cell Sci.*, 113 (7): 1101-09, 2000; Raju et al., SANE, a novel lem domain protein, regulates bone morphogenetic protein signaling through interaction with smad1. *J. Biol. Chem.*, 278(1):428-37, 2003; Ring and Cho, Specificity in transforming growth factor-b signaling pathways. *Am. J. Hum. Genet.*, 64:691-97, 1999; Wrana, J., Regulation of Smad activity. *Cell*, 100:189-92, 2000; and Yamaguchi et al., XIAP, a cellular member of the inhibitor of apoptosis protein family, links the receptors to TAB1-TAK1 in the BMP signaling pathway. *EMBO J.*, 18(1): 179-87, 1999.

The method of the present invention comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a BMP signalling pathway; (d) contacting the second collection of cells with an activator of a BMP signalling pathway; and (e) determining if the candidate modulator in step (b) modulates neural differentiation, wherein modulation of neural differentiation is indicative of modulation of a BMP signalling pathway. By way of example, the modulating effect, if any, of the candidate modulator may be determined by comparing neural differentiation (e.g., the rate thereof) of the cells in step (b) with neural differentiation (e.g., the rate thereof) of the cells in step (c).

As used herein, an "activator" of a BMP signalling pathway includes any factor, now known or later discovered, that effects, increases, induces, initiates, or stimulates release of a BMP protein; a factor that effects or produces biochemical signalling within a BMP signalling pathway; and a factor that increases, induces, initiates, or stimulates signalling within a BMP signalling pathway. For example, the activator of BMP signalling may be a BMP protein (e.g., BMP1, BMP2, BMP2b, BMP3 (ADMP), BMP4, BMP5, BMP6, BMP7, BMP8, BMP9, BMP10, BMP11, and BMP15), a BMP receptor, or an agonist of a BMP signalling pathway. An "agonist" of a BMP signalling pathway, as used herein, is a factor that has affinity for, and stimulates physiologic activity at, cell receptors normally stimulated by naturally-occurring substances, such that signalling in a BMP signalling pathway within the cell is increased, initiated, stimulated, or induced.

Examples of the activator of a BMP signalling pathway include, without limitation, activin, ActRII, ActRIIB, ACVR1 (ALK2), ACVRIB (ALK4), ACVR2, ACVR2B, ACVRL1 (ALK1), ADMP (anti-dorsalizing morphogenetic protein), ALK5, ALK7, ALK8, AMH, AMHR2, BAMBI, BGLAP (osteocalcin), a BMP protein (e.g., BMP1, BMP2, BMP2b, BMP3 (ADMP), BMP4, BMP5, BMP6, BMP7, BMP8, BMP9, BMP10, BMP11, and BMP15), a BMP receptor, BMPR1A (ALK3), BMPRIB (ALK6), BMPR11, BMPR2, CDC25A, CDKN1A (p21Waf1/p21Cip1), CDKN2B (p15Ink2b), CER1 (cerberus), CHRD (chordin), CKTSF1B1 (gremlin), COL1A1, COL1A2, COL3A1, DLX2, EBAF (leftyA), ENG (endoglin), EVI1 (Evi-1), Fast1, FKBP1B, FOS, FST (follistatin), gata, GDF1 (growth and differentiation factor 1), GDF2 (BMP9), GDF3 (Vgr-2), GDF5 (CDMP-1), GDF6, GDF8, GDF9, GDF10, GDF11 (BMPI 1), goosecoid, ID1, ID2, ID3, ID4, IGF1, IGFBP3, IL6, INHA (inhibin a), INHBA (inhibin BA), INHBB (inhibin BB), INHBC (inhibin BC), ITGB5 (integrin b5), ITGB7 (integrin b7), IVL (involucrin), JUN, JUNB, LEFTB (leftyB), MADH1 (smad1), MADH2 (smad2), MADH3 (smad3), MADH4 (smad4), MADH5 (smad5), MADH6 (smad6), MADH7 (smad7), MADH9 (smad9), Msx, MYC, NBLI (DAN), NMA, NODAL, Nodal-related Vg1, noggin, OAZ, PDGFB, PLAU (uPA), RUNX1 (AML1), RUNX2, SANE (Smad1 antagonistic effector), SERPINE1 (PAI-1), Ski, smad4b (smad10), smad8, Smurf1, Smurf2, SNC73 (IgA), Snow, somitabun, SOX4, STAT1, TAB1, TAK1, TβR11, TCF8 (AREB6), TDGF1, TGFβ (e.g., TGFβ1, TGFβ2, and TGFβ3), TGFBR2, TGFBR1 (ALK5), TGFBR3, TGFB1I1, TGIF, TIMP1, tob, tolloid/mini-fin, TSC22, TSG, Twsg1 (twisted gastrulation homolog 1), type I receptors, type II receptors, Vent, XIAP, Xngnr SoxD, Xnr3, and any analogue or homologue thereof. In one embodiment of the present invention, the candidate modulator enhances neural differentiation. In another embodiment, the candidate modulator modulates the BMP4 signalling pathway and inhibits neural differentiation.

In accordance with the method of the present invention, the cells in step (a) may differentiate into repositioned neural progenitor cells or fully-differentiated neural cells. In one embodiment of the present invention, the fully-differentiated neural cells are motor neurons. In another embodiment, the cells in step (a) and step (b) are neural progenitor cells, and the cells in step (a) differentiate into dorsal spinal motor neurons. In yet another embodiment of the present invention, the neural progenitor cells in step (a) and step (b) are generated from embryonic stem cells. In one embodiment, the embryonic stem cells are mouse embryonic stem cells. In another embodiment, the embryonic stem cells are human embryonic stem cells.

The present invention also provides a method for identifying a modulator of neural differentiation. This method comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a BMP signalling pathway; (d) contacting the second collection of cells with an activator of a BMP signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c). Also provided is a modulator identified by this method.

Additionally, the present invention provides a method for identifying a modulator of BMP-dependent neural differentiation, comprising the steps of: (a) obtaining or generating a collection of cells selected from the group consisting of embryonic stem cells, embryoid bodies, and neural progenitor cells; (b) contacting the collection of cells with a candidate modulator; and (c) determining if the candidate modulator modulates BMP-dependent neural differentiation of the cells in the collection. Also provided is a modulator identified by this method. As used herein, a "modulator of BMP-dependent neural differentiation" may be any agent or combination of agents that has an antagonistic (inhibitory) or agonistic (facilitatory) effect on BMP-dependent neural differentiation. BMP-dependent neural differentiation, and any modulation thereof, may be detected using techniques and assays well known in the art, including those described herein. In one embodiment of the present invention, the collection of cells in step (b) is further contacted with the candidate modulator in the presence of an activator of a BMP signalling pathway.

The present invention further provides a method for identifying a modulator of a Hh signalling pathway. Also provided is a modulator (agonist or antagonist) identified by this method. As used herein, "Hh" refers to any member of the Hh family of proteins now known or later discovered, including, without limitation, DHh, 1Hh, and SHh. As further used herein, "Hh signalling pathway" refers to the cascade of biochemical signalling that includes, is initiated by, or directly or indirectly results from release of a Hh protein, particularly signalling that relates to direction or position of cells in an embryo during development and differentiation. Additionally, as used herein, a "modulator of a Hh signalling pathway" may be any agent or combination of agents that has an antagonistic (inhibitory) or agonistic (facilitatory) effect on a Hh signalling pathway.

The hedgehog (Hh) signalling pathway is a highly-conserved cascade involved in many developmental processes. For example, the pathway regulates the development of numerous tissues and cell types. Mutational inactivation of the Hh pathway has also been demonstrated in human malignancies of the skin, cerebellum, and skeletal muscle, and in congenital diseases and defects. Thus, elements of the Hh pathway are potential drug targets for the treatment of degenerative diseases, like Parkinson's disease, and neoplasms.

Two main components of the Hh signalling pathway are Patched (Ptc), the cell-surface receptor protein to which the secreted signal binds, and Smoothened (Smo), an intracellular protein that activates genes in response to the Hh signal. In the absence of Hh, Ptc inhibits the activity of Smo; however, when Hh molecules are secreted by nearby cells, they bind to Ptc, unleashing Smo. Smo then transmits the signal through a chain of regulators, resulting in the activation of certain genes—some of which encode proteins that trigger growth. Important genes in the hedgehog signalling pathway include BMP2, BMP4, DHh, EN1 (engrailed), HIP, HNF3B (forkhead box A2), Ihh, PTCH1 (patched 1), PTCH2 (patched 2), SHh, WNT1, WNT2, and WSB1. Hh signalling is discussed in the following reviews, the contents of which are hereby incorporated by reference herein: Bak et al., The Hedgehog signaling pathway—implications for drug targets in cancer and neurodegenerative disorders. *Pharmacogenomics*, 4(4): 411-29, 2003; Kalderon, D., Hedgehog signaling: Costal-2 bridges the transduction gap. *Curr. Biol.*, 14(2):R67-9, 2004; McMahon, A. P., More surprises in the hedgehog signaling pathway. *Cell*, 100:185-88, 2000; and Wetmore, C., Sonic hedgehog in normal and neoplastic proliferation: insight gained from human tumors and animal models. *Curr. Opin. Genet. Dev.*, 13(1):3442, 2003.

The method of the present invention comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a Hh signalling pathway; (d) contacting the second collection of cells with an activator of a Hh signalling pathway; and (e) determining if the candidate modulator in step (b) modulates neural differentiation, wherein modulation of neural differentiation is indicative of modulation of a Hh signalling pathway. By way of example, the modulating effect, if any, of the candidate modulator may be determined by comparing neural differentiation (e.g., the rate thereof) of the cells in step (b) with neural differentiation (e.g., the rate thereof) of the cells in step (c). In one embodiment of the present invention, the Hh signalling pathway is the DHh signalling pathway, the IHh signalling pathway, or the SHh signalling pathway.

As used herein, an "activator" of a Hh signalling pathway includes any factor, now known or later discovered, that effects, increases, induces, initiates, or stimulates release of a Hh protein; a factor that effects or produces biochemical signalling within a Hh signalling pathway; and a factor that increases, induces, initiates, or stimulates signalling within a Hh signalling pathway. For example, the activator of Hh signalling may be a Hh protein (e.g., DHh, IHh, or SHh), a Hh receptor, or an agonist of a Hh signalling pathway. An "agonist" of a Hh signalling pathway, as used herein, is a factor that has affinity for, and stimulates physiologic activity at, cell receptors normally stimulated by naturally-occurring substances, such that signalling in a Hh signalling pathway within the cell is increased, initiated, stimulated, or induced.

Examples of the activator of a Hh signalling pathway include, without limitation, A2M (a2macroglobulin), AKT, androgen, ATF2, BAX, BCL2, BCL2A1 (Bf1-1/A1), BCL2L1 (Bcl-XL), BRCA1, BIRC1 (NAIP), BIRC2 (c-IAP2), BIRC3 (c-IAP1), BMP2, BMP4, calcium, CCND1 (cyclin D1), CD5, CDK2, CDKN1A (p21Waf1/p21Cip1), CDKN1B (p27), CDKN1C (p57Kip2), CDKN2A (p16Ink4), CDKN2B (p15 Ink2b), CDKN2C (p18-a cdk4 inhibitor), CDKN2D (p19), CDX1, CEBPB (C/EBP-beta), CSF2 (GM-CSF), CSN2 (β-casein), CTSD (cathepsin D), CYP19 (aromatase p450), EGFR, EGR1 (egr-1), EN1 (engrailed homologue 1), estrogen, FASN (fatty acid synthase), FLJ12541 (Stra6), FN1 (fibronectin), FOS (c-fos), GADD45A (gadd45), GYS1 (GS, glycogen synthase), a hedgehog protein (e.g., DHh, 1Hh, or SHh), HIP, HK2 (hexokinase II), a hedgehog receptor, HNF3B (forkhead box A2), HOXA1, HOXB1, HSF1 (tcf5), HSPB1 (hsp27), HSPCA (hsp90), ICAM1, IGFBP3, insulin, IL2, IL2RA (IL-2 Ra), IL4, IL4R, IR4R, Jak, JUNB (jun-B), JUN (c-jun), KLK2 (hGK2), KLK3 (PSA), LDL, LEP (Ob), MDM2, MIG, MMP-7 (matrilysin), MMP10 (stromelysin-2), MYC (c-myc), NFAT, NFKB1 (NFkB), NFKBIA (IkBa), NOS2 (iNOS), ODC1 (ornithine decarboxylase), p53, PECAM1, PGR (PR), phospholipase C, PI3 kinase, PIG3, PRKCA (PKCA), PRKCB1, PRKCE (PKCE), protein kinase C, PTCH1 (patched 1), PTCH2 (patched 2), PTGS2 (COX-2), RBP1 (CRBPI), RBP2 (CRABPII), retinoic acid, SCYA2 (mcp-1), SELE (ELAM-1/E-selectin), SELPLG (P-selectin), Smo, Src, TGFβ, TFRC (p90/transferrin receptor), TMEPA1, TNFA(TNFa), TNFRSF6 (Fas), TNFRSF10B (TrailR/DR5), TNFSF6 (FasL), TP53 (p53), VCAM1, WISP1, WISP2, WISP3, WNT1, WNT2, WSB1, ZNF147 (Efp), and any analogue or homologue thereof. In one embodiment of the present invention, the candidate modulator enhances neural differentiation.

In accordance with the method of the present invention, the cells in step (a) may differentiate into repositioned neural progenitor cells or fully-differentiated neural cells. In one embodiment, the fully-differentiated neural cells are motor neurons. In another embodiment, the cells in step (a) and step (b) are neural progenitor cells of a spinal caudal character, and the cells in step (a) differentiate into repositioned neural progenitor cells (e.g., repositioned neural progenitor cells of a ventral character, neural progenitor cells of ventral interneurons, or neural progenitor cells of motor neurons) or fully-differentiated motor neurons (e.g., spinal motor neurons). In yet another embodiment of the present invention, the neural progenitor cells in step (a) and step (b) are generated from embryonic stem cells. In one embodiment, the embryonic stem cells are mouse embryonic stem cells. In another embodiment, the embryonic stem cells are human embryonic stem cells.

The present invention further provides a method for identifying a modulator of neural differentiation. This method comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a Hh signalling pathway; (d) contacting the second collection of cells with an activator of a Hh signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c). Also provided is a modulator identified by this method.

Additionally, the present invention provides a method for identifying a modulator of Hh-dependent neural differentiation, comprising the steps of: (a) obtaining or generating a collection of cells selected from the group consisting of embryonic stem cells, embryoid bodies, and neural progenitor cells; (b) contacting the collection of cells with a candidate modulator; and (c) determining if the candidate modulator modulates Hh-dependent neural differentiation of the cells in the collection. Also provided is a modulator identified by this method. As used herein, a "modulator of Hh-dependent neural differentiation" may be any agent or combination of agents that has an antagonistic (inhibitory) or agonistic (facilitatory) effect on Hh-dependent neural differentiation. Hh-dependent neural differentiation, and any modulation thereof, may be detected using techniques and assays well known in the art, including those described herein. In one embodiment of the present invention, the collection of cells in step (b) is further contacted with the candidate modulator in the presence of an activator of a Hh signalling pathway.

The present invention further provides a method for identifying a modulator of an FGF signalling pathway. Also provided is a modulator (agonist or antagonist) identified by this method. As used herein, "FGF" refers to any member of the FGF family of proteins now known or later discovered, including, without limitation, FGFl, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, and FGF23. As further used herein, "FGF signalling pathway" refers to the cascade of biochemical signalling that includes, is initiated by, or directly or indirectly results from release of an FGF protein, particularly signalling that relates to direction or position of cells in an embryo during development and differentiation. Additionally, as used herein, a "modulator of an FGF signalling pathway" may be any agent or combination of agents that has an antagonistic (inhibitory) or agonistic (facilitatory) effect on an FGF signalling pathway.

Growth factors play an important role in biological processes, including embryogenesis, inflammation, and wound healing. These secreted proteins induce proliferation by binding to their cognate cell-surface receptors. Many growth factors have very versatile functions. For example, one factor may induce growth in one cell type, and then induce other responses (such as differentiation or migration) in another cell type. Unregulated expression of these growth factors often leads to the progression of certain disease states, including atherosclerosis and tumorigenesis.

There are 22 known members of the fibroblast growth factor (FGF) family in vertebrates. One of the defining features shared by this family is a high affinity for heparin and heparin-like glycosaminoglycans (HLGAGs). FGFs are vital intercellular signalling molecules that regulate numerous processes in embryogenesis and organogenesis. In particular, FGF signalling is required for cell proliferation/survival at the time of embryonic implantation (embryonic day E 4.0), and for cell migration during gastrulation (beginning at ~6.5).

There are four signal-transducing FGF receptors (FGFRs), all from the tyrosine kinase gene family. These four cell-surface receptors bind members of the FGF family with varying affinities. Like the FGFs, FGFRs also play important roles during embryogenesis and organogenesis. The extracellular region of the FGFR contains three immunoglobulin-like (Ig-like) domains: IgI, IgII, and IgIII. Three alternative versions of IgIII domains (known as domains IIIa, IIb, and Ic) exist in FGFRs1-3.

The binding of FGF to FGFR causes the autophosphorylation and activation of the receptor tyrosine kinase (RTK). The RTK then activates the Ras/MAPK signalling pathway. The RTK binds to an adaptor protein (Grb2 or Grb2-Sos complex), by way of its docking protein, Shp or FRS2. Sos then activates Ras, which, in turn, phosphorylates a series of MAP kinases (Raf, MEK, and ERK). ERK enters the nucleus and phosphorylates and activates transcription factors, such as ELK-1, which regulate various targets.

Many of the molecular components in the above pathway—such as Ras, GTPase, Raf kinase, and MAPK—are shared among different RTKs. Ras directly interacts with, and activates, Raf; in turn, Raf phosphorylates and activates MEK; MEK then phosphorylates and activates the MAP kinases, including ERK1 and ERK2. ERK is an extracellular-signal-regulated kinase that can enter the nucleus and phosphorylate certain transcription factors, like ELK-1, within the target cell.

Relevant genes involved in FGF signalling may be classified according to function as follows: FGF1, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, and FGF23. Genes that are relevant in the signalling of other growth factors include the following: genes from the epidermal growth factor (EGF) family (AREG (amphiregulin), DTR (HB-EGF), EGF, LOC145957 (neuregulin 4), NRG1, NRG2, and NRG3); genes from the platelet-derived growth factor (PDGF) family (FIGF (VEGFD), PDGFA, PDGFB, PDGFC, SCDGF-B (PDGFD), VEGF, VEGFB, and VEGFC); genes from the tumor growth factor (TGF) family (TGFA, TGFB1, TGFB2, and TGFB3); genes from the neuronal growth factors (BDGF, CNTF, GDNF, KLK2 (NGFA), MDK (midkine), NGFB, NRP1 (neuropilin 1), NRP2, NT6G, NTF3, and NTF5); genes from the cytokines (CSFI (M-CSF), CSF2 (GM-CSF), CSF3 (G-CSF), EPO, interleukins (IL1A, IL1B, IL2, IL3, IL4, IL5, IL6, IL7, IL8, IL9, IL10, IL11, IL12A, IL12B, IL13, IL14, IL15, IL16, IL17, IL17B, IL17C, IL17E, IL17F, IL18, IL19, IL20, and IL22), KITLG (SCF), LTA (TNF beta), and TNF); and other related growth-factor genes (CTGF, CXCL1 (MGSA), ECGF1 (PD-ECGF), GH1, GH2, HGF, IGF1, IGF2, INS, PGF (PLGF), and PTN).

FGF signalling is discussed in the following reviews, the contents of which are hereby incorporated by reference herein: Akhurst and Derynck, TGF-beta signaling in cancer—a double-edged sword. *Trends Cell Biol.*, 11(11):S44-51, 2001; Cross and Claesson-Welsh, FGF and VEGF function in angiogenesis: signalling pathways, biological responses and therapeutic inhibition. *Trends Pharmacol. Sci.*, 22(4):201-07, 2001; Danielsen and Maihle, The EGF/ErbB receptor family and apoptosis. *Growth Factors*, 20(1):1-15, 2002; Falls, D. L., Neuregulins: functions, forms, and signaling strategies. *Exp. Cell Res.*, 284(1)14-30, 2003; Lauta, V. M., A review of the cytokine network in multiple myeloma: diagnostic, prognostic, and therapeutic implications. *Cancer*, 97(10):2440-52, 2003; Ornitz and Itoh, Fibroblast growth factors. *Genome. Biol.*, 2(3):REVIEWS3005, 2001; and Yu et al., Platelet-derived growth factor signaling and human cancer. *J. Biochem. Mol. Biol.*, 36(1):49-59, 2003.

The method of the present invention comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of an FGF signalling pathway; (d) contacting the second collection of cells with an activator of an FGF signalling pathway; and (e) determining if the candidate modulator in step (b) modulates neural differentiation, wherein modulation of neural differentiation is indicative of modulation of an FGF signalling pathway. By way of example, the modulating effect, if any, of the candidate modulator may be determined by comparing neural differentiation (e.g., the rate thereof) of the cells in step (b) with neural differentiation (e.g., the rate thereof) of the cells in step (c).

As used herein, an "activator" of an FGF signalling pathway includes any factor, now known or later discovered, that effects, increases, induces, initiates, or stimulates release of a Wnt protein; a factor that effects or produces biochemical signalling within an FGF signalling pathway; and a factor that increases, induces, initiates, or stimulates signalling within an FGF signalling pathway. For example, the activator of FGF signalling may be an FGF protein (e.g., FGF1, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, and FGF23), an FGF receptor, or an agonist of an FGF signalling pathway. An "agonist" of an FGF signalling pathway, as used herein, is a factor that has affinity for, and stimulates physiologic activity at, cell receptors normally stimulated by naturally-occurring substances, such that signalling in an FGF signalling pathway within the cell is increased, induced, initiated, stimulated, or induced.

Examples of the activator of an FGF signalling pathway include, without limitation, activin, AREG (amphiregulin), BDGF, BEK, BMP, brachyury, BSN-CM, BTL, chordin, c-met, CNTF, Crk, CSF1 (M-CSF), CSF2 (GM-CSF), CSF3 (G-CSF), CTGF, CXCL1 (MGSA), DAG, DTR (HB-EGF), E2A-Pbx1, ECGF1 (PD-ECGF), EGF, ELK-1, EPO, ERK1, ERK2, an FGF protein (e.g., FGF1, FGF2, FGF3, FGF4, FGF5, FGF6, FGF7, FGF8, FGF9, FGF10, FGF11, FGF12, FGF13, FGF14, FGF16, FGF17, FGF18, FGF19, FGF20, FGF21, or FGF23), an FGF receptor (e.g., FGFR-1, IIIb & IIIc; FGFR-2, IIIb & IIIc; FGFR-3, IIIb & IIIc; and FGFR-4), FIGF (VEGFD), FRS2, GDNF, GH1, GH2, Grb2, Grb2-Sos, GTPase, heparin, HGF, HLGAG, HSPG, HTL, IGF1, IGF2, an interleukin (e.g., IL1A, IL1B, IL2, IL3, IL4, IL5, IL6, IL7, IL8, IL9, IL10, IL11, IL12A, IL12B, IL13, IL14, IL15, IL16, IL17, IL17B, IL17C, IL17E, IL17F, IL18, IL19, IL20, IL22), INS, IP3, KITLG (SCF), KLK2 (NGFA), LIF, LOC145957 (neuregulin 4), LTA (TNF beta), MAPK, MDK (midkine), MEK, MSX, NDK, NGFB, NRG1, NRG2, NRG3, NRP1 (neuropilin 1), NRP2, NT6G, NTF3, NTF5, PDGFA, PDGFB, PDGFC, PGF (PLGF), P13 kinase, PIP2, PKC, PLC, PTN, RACK1, Raf kinase, Ras, RTK, SCDGF-B (PDGFD), Shc, SHP1, SHP2, SNT-1, Sos, Spry, Src, TGFA, TGFB1, TGFB2, TGFB3, TNF, VEGF, VEGFB, VEGFC, WT1, Xbra, XER81, XFLRT3, Xpo, and any analogue or homologue thereof. In one embodiment of the present invention, the candidate modulator enhances neural differentiation.

In accordance with the method of the present invention, the cells in step (a) may differentiate into repositioned neural progenitor cells or fully-differentiated neural cells. In one embodiment, the fully-differentiated neural cells are motor neurons. In another embodiment, the neural progenitor cells in step (a) and step (b) are generated from embryonic stem cells. In one embodiment, the embryonic stem cells are murine embryonic stem cells. In another embodiment, the embryonic stem cells are human embryonic stem cells.

The present invention also provides a method for identifying a modulator of neural differentiation. This method comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of an FGF signalling pathway; (d) contacting the second collection of cells with an activator of an FGF signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c). Also provided is a modulator identified by this method.

Additionally, the present invention provides a method for identifying a modulator of FGF-dependent neural differentiation, comprising the steps of: (a) obtaining or generating a collection of cells selected from the group consisting of embryonic stem cells, embryoid bodies, and neural progenitor cells; (b) contacting the collection of cells with a candidate modulator; and (c) determining if the candidate modulator modulates FGF-dependent neural differentiation of the cells in the collection. Also provided is a modulator identified by this method. As used herein, a "modulator of FGF-dependent neural differentiation" may be any agent or combination of agents that has an antagonistic (inhibitory) or agonistic (facilitatory) effect on FGF-dependent neural differentiation. FGF-dependent neural differentiation, and any modulation thereof, may be detected using techniques and assays well known in the art, including those described herein. In one embodiment of the present invention, the collection of cells in step (b) is further contacted with the candidate modulator in the presence of an activator of an FGF signalling pathway.

The present invention further provides a method for identifying a modulator of a retinoid signalling pathway. Also provided is a modulator (agonist or antagonist) identified by this method. As used herein, "retinoid" refers to any member of the retinoid family now known or later discovered, including, without limitation, retinoic acid. As further used herein, "retinoid signalling pathway" refers to the cascade of biochemical signalling that includes, is initiated by, or directly or indirectly results from release of a retinoid, particularly signalling that relates to direction or position of cells in an embryo during development and differentiation. Additionally, as used herein, a "modulator of a retinoid signalling pathway" may be any agent or combination of agents that has an antagonistic (inhibitory) or agonistic (facilitatory) effect on a retinoid signalling pathway.

Retinoid signalling is involved in distinct stages of the developmental sequence of skeletogenesis. Retinoid signalling involves several components, including enzymes that control the synthesis and degradation of retinoic acid (RA), cytoplasmic RA-binding proteins, and nuclear receptors that modulate gene transcription; each component has been implicated in skeletal development. Most of the effects of retinoids on gene expression are mediated by nuclear retinoic acid receptors, or RARs (alpha, beta, and gamma), and retinoid X receptors, or RXRs (alpha, beta, and gamma), which function as retinoid-activated transcription factors. Manipulation of the retinoid signalling pathway significantly affects the expression of the skeletogenic master regulatory factors, Sox9 and Cbfa1.

Important genes in the retinoid signalling pathway include, without limitation, CDX1, CTSD (cathepsin D), Cyp26, EN1 (engrailed homolog 1), FLJ12541 (Stra6), HOX1, HOXA1, HOXB1, RAR, RBP1 (CRBPI), RBP2 (CRABPII), retinoids, and RXR. Retinoid signalling is discussed in the following reviews, the contents of which are hereby incorporated by reference herein: Chambon, P., The molecular and genetic dissection of the retinoid signaling pathway. *Recent Prog. Horn. Res.*, 50:317-32, 1995; Chambon, P., The retinoid signaling pathway: molecular and genetic analyses. *Semin. Cell Biol.*, 5(2): 115-25, 1994; Chiba et al., Distinct retinoid X receptor-retinoic acid receptor heterodimers are differentially involved in the control of expression of retinoid target genes in F9 embryonal carcinoma cells. *Mol. Cell Biol.*, 17:3013-20, 1997; and Weston et al., Revisiting the role of retinoid signaling in skeletal development. *Birth Defects Res. Part C Embryo Today*, 69(2): 156-73, 2003.

The method of the present invention comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a retinoid signalling pathway; (d) contacting the second collection of cells with an activator of a retinoid signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c), wherein modulation of neural differentiation is indicative of modulation of a retinoid signalling pathway. In one embodiment of the present invention, the retinoid signalling pathway is the retinoic acid signalling pathway.

As used herein, an "activator" of a retinoid signalling pathway includes any factor, now known or later discovered, that effects, increases, induces, initiates, or stimulates release of a retinoid; a factor that effects or produces biochemical signalling within a retinoid signalling pathway; and a factor that increases, induces, initiates, or stimulates signalling within a retinoid signalling pathway. For example, the activator of retinoid signalling may be retinoic acid or an agonist of a retinoid signalling pathway. An "agonist" of a retinoid signalling pathway, as used herein, is a factor that has affinity for, and stimulates physiologic activity at, cell receptors normally stimulated by naturally-occurring substances, such that signalling in a retinoid signalling pathway within the cell is increased, initiated, stimulated, or induced.

Examples of the activator of a retinoid signalling pathway include, without limitation, Cbfa1, CDX1, CTSD (cathepsin D), Cyp26, EN1(engrailed homolog 1), FLJ12541 (Stra6), HOX1, HOXA1, HOXB1, phorbol-12-myristate-13-acetate-activated protein kinase C, RAR, RBP1 (CRBPI), RBP2 (CRABPII), a retinoid, a retinoid receptor, RXR, Sox9, and any analogue or homologue thereof. In one embodiment of the present invention, the candidate modulator enhances neural differentiation.

In accordance with the method of the present invention, the cells in step (a) may differentiate into repositioned neural progenitor cells or fully-differentiated neural cells. In one embodiment, the fully-differentiated neural cells are motor neurons. In another embodiment, the cells in step (a) and step (b) are embryoid bodies, and the cells in step (a) differentiate into neural progenitor cells (which may further differentiate into motor neurons). In yet another embodiment of the present invention, the cells in step (a) and step (b) are neural progenitor cells of a midbrain character, and the cells in step (a) differentiate into repositioned neural progenitor cells of a caudal character or repositioned neural progenitor cells of spinal interneurons. These neural progenitor cells may then further differentiate into motor neurons. In still another embodiment, the embryoid bodies and neural progenitor cells in step (a) and step (b) are generated from embryonic stem cells (e.g., murine embryonic stem cells or human embryonic stem cells).

The present invention also provides a method for identifying a modulator of neural differentiation. This method comprises the steps of: (a) obtaining or generating a first collection of cells selected from the group consisting of embryonic stem cells, embryoid bodies, and neural progenitor cells; (b) obtaining or generating a second collection of cells selected from the same group as the cells selected in step (a); (c) contacting the first collection of cells with a candidate modulator, in the presence of an activator of a retinoid signalling pathway; (d) contacting the second collection of cells with an activator of a retinoid signalling pathway; and (e) determining if the candidate modulator in step (b) modulates neural differentiation. By way of example, the modulating effect, if any, of the candidate modulator may be determined by comparing neural differentiation (e.g., the rate thereof) of the cells in step (b) with neural differentiation (e.g., the rate thereof) of the cells in step (c). Also provided is a modulator identified by this method.

Additionally, the present invention provides a method for identifying a modulator of retinoid-dependent neural differentiation, comprising the steps of: (a) obtaining or generating a collection of cells selected from the group consisting of embryonic stem cells, embryoid bodies, and neural progenitor cells; (b) contacting the collection of cells with a candidate modulator; and (c) determining if the candidate modulator modulates retinoid-dependent neural differentiation of the cells in the collection. Also provided is a modulator identified by this method. As used herein, a "modulator of retinoid-dependent neural differentiation" may be any agent or combination of agents that has an antagonistic (inhibitory) or agonistic (facilitatory) effect on retinoid-dependent neural differentiation. Retinoid-dependent neural differentiation, and any modulation thereof, may be detected using techniques and assays well known in the art, including those described herein. In one embodiment of the present invention, the collection of cells in step (b) is further contacted with the candidate modulator in the presence of an activator of a retinoid signalling pathway.

The present invention is described in the following Examples, which are set forth to aid in the understanding of the invention, and should not be construed to limit in any way the scope of the invention as defined in the claims which follow thereafter.

EXAMPLES

Example 1

ES-Cell cultures

For some experiments, wild-type (MM13 or W9.5) or HB9::GFP transgenic-mouse-derived (HBG3) embryonic stem (ES) cells were grown on feeder layers of primary mouse embryonic fibroblasts in ES-cell medium (Dulbecco's Modified Eagle's Medium (DMEM) with 4500 mg/l glucose and 2250 mg/l Na-bicarbonate, supplemented with 1× nonessential amino acids, 1× nucleosides (all from Specialty Media, Lavellette, N.J.), 0.1 mM 2-mercaptoethanol (Sigma Chemical Co., St. Louis, Mo.)), 2 mM L-glutamine (Gibco BRL, Gaithersburg, Md.), 1× penicillin/streptomycin (Gibco), 15% FBS (HyClone, Logan, Utah), and 1000 µ/ml LIF (Chemicon, Temecula, Calif.). ES-cell colonies were partially dissociated with trypsin, 2 days after plating, and cultured in DFK5 medium consisting of DF medium (DMEM/F12 supplemented with glucose (4500 mg/l; Sigma), 2 mM L-glutamine (Gibco), 1× penicillin/streptomycin (Gibco), 0.1 mM 2-mercaptoethanol (Sigma), 1× insulin-transferrin-selenium supplement (Gibco), 20 nM progesterone (Sigma), and 60 µM putrescine (Sigma) mixed 1:1 with ESK10 medium (ES-cell medium without LIF and FBS, but supplemented with 10% Knockout Serum Replacement (Gibco)). Medium was replaced 2 days later with fresh medium supplemented with retinoic acid (RA) (100 nM to 2 µM) (Sigma), Sonic hedgehog protein (SHh-N; 300 nM) (Curis, Inc., Cambridge, Mass.), hedgehog agonist Hh-Ag1.3 (1-1000 nM) (Curis, Inc.), or hedgehog blocking antibody (5E1, 30 µg/ml). Embryoid bodies (EBs) were cultured for an additional 2-5 days. For some experiments, ES cells were grown on a monolayer of stromal PA6 cell line (Riken Cell Bank, Japan), in DFK5 medium alone, or supplemented with 2 µM RA, as described (Kawasaki et al., Induction of midbrain dopaminergic neurons from ES cells by stromal cell-derived inducing activity. Neuron, 28:31-40, 2000).

Some HBG3 ES-cell-derived EBs were dissociated with a papain dissociation system (Worthington Biochemical Corp., Freehold, N.J.) 4 days after induction, FACS sorted based on the endogenous eGFP expression, plated on Petri dishes or Terasaki wells coated with matrigel (BD), and cultured in F12 medium (Specialty Media) supplemented with 5% horse serum (Gibco), 1×B-27 supplement (Gibco), 1× insulin-transferrin-selenium supplement (Gibco), 20 nM progesterone (Sigma), and 60 µM putrescine (Sigma). A mixture of neurotrophic factors (GDNF, NT3, CNTF, and BDNF) (10 ng/ml; R&D Systems, Inc., Minneapolis, Minn.) was included in selected experiments.

For Examples 7-11, MM13 or HB9::GFP transgenic-mouse-derived (HBG3.1) (Wichterle et al., Directed differentiation of embryonic stem cells into motor neurons. Cell, 110:385-97, 2002) ES cells were grown on mouse embryonic fibroblasts in ES-cell medium (DMEM with 4500 mg/l glucose and 2250 mg/l Na-bicarbonate, supplemented with 1× nonessential amino acids, 1× nucleosides (all from Specialty Media), 0.1 mM 2-mercaptoethanol (Sigma), 2 mM L-glutamine (Gibco-BRL), 1× penicillin/streptomycin (Gibco-BRL), 15% FBS (HyClone), and 1000 u/ml LIF (Chemicon). ES-cell colonies were partially dissociated with trypsin, after 2 days, and cultured in differentiation medium (DMEM/F12 supplemented with glucose (4500 mg/l; Sigma), bicarbonate supplemented with 1× nonessential amino acids, 1× nucleosides (all from Specialty Media), 0.1 mM 2-mercaptoethanol (Sigma), 2 mM L-glutamine (Gibco-BRL), and 10% knockout serum replacement (Gibco)) for 2-8 days. Medium was replaced every 2 days. Medium was supplemented by factors, at the start of ES-cell aggregation/differentiation (day 0) or on day 2, as indicated below, and cultured for a further 2-8 days.

Example 2

Immunocytochemistry

Embryoid bodies (EBs) were fixed with 4% paraformaldehyde, and sectioned on acryostat. For immunostaining, the following antibodies were used: rabbit αHB9, αOlig2, αNkx2.2, αLhx3, αDbx1 (Pierani et al., Control of interneuron fate in the developing spinal cord by the progenitor homeodomain protein Dbx1. Neuron, 29(2):367-84, 2001), αIrx3, αGFP (1:2000, Molecular Probes, Inc., Eugene, Oreg.), αSox1 (1:500) (Pevny et al., Generation of purified neural precursors from embryonic stem cells by lineage selection. Curr. Biol., 8:971-74, 1998), αOtx2 (1:1000) (Mallamaci et al., OTX2 homeoprotein in the developing central nervous system and migratory cells of the olfactory area. Mech. Dev., 58:165-78, 1996), αHoxC5 (Liu et al., Assigning the positional identity of spinal motor neurons. Rostrocaudal patterning of Hox-c expression by FGFs, Gdf11, and retinoids. Neuron, 32:997-1012, 2001), and αChx10; mouse αPax7, αPax6, αHB9, αLim1, αNkx6.1, αNkx2.2, αEn1, αLim2 (mouse specific), αNCAM (mouse specific), αSC1 (chick specific), αNeuN (1:500, Chemicon), αTuj1 (1:2000) (BabCo, Berkeley, Calif.), αSyb (mouse specific; 1:1000) (Synaptic Systems), αSyn (1:1000, Synaptic Systems), and αNeurofilament; guinea pig α-Isl1, anti-Olig2, and anti-Hoxc6 (Liu et al., Assigning the positional identity of spinal motor neurons. Rostrocaudal patterning of Hox-c expression by FGFs, Gdf11, and retinoids. Neuron, 32:997-1012, 2001); goat-αChAT (1:200) (Chemicon), αVAChT (mouse specific; 1:1000) (Chemicon) (Novitch et al., Coordinate regulation of motor neuron subtype identity and pan-neuronal properties by the bHLH repressor Olig2. Neuron, 31:773-89, 2001, wherever not specified). FITC-, Cy3-, and Cy5-conjugated secondary antibodies were used (Jackson Immunoresearch). Images were obtained using a BioRad confocal microscope.

Example 3

Generation of EGFP Transgenic Mouse Lines

A transgenic mouse line was established by pronucleus injection of a construct that used a ~9 kB fragment comprising the 5' upstream region of the murine HB9 gene (Arber et al., Requirement for the homeobox gene Hb9 in the consolidation of motor neuron identity. *Neuron,* 23:659-764, 1999), followed by a 5' splice substrate (Choi et al., A generic intron increases gene expression in transgenic mice. *Mol. Cell Biol.,* 11:3070-74, 1991), an eGFP gene, and a bovine growth hormone polyadenylation signal. The ~9 kB Not1 fragment of HB9 is sufficient to direct eGFP expression to develop motor neurons in transgenic embryos examined from E9.5 to P10. In one transgenic line (mHB9-Gfp1b), the pattern of eGFP expression corresponded closely to the profile of expression of endogenous HB9. ES-cell lines were derived from mHB9-Gfp1b heterozygous blastocysts, as previously described (Abbondanzo et al., Derivation of embryonic stem cell lines. *Methods Enzymol.,* 225:803-23, 1993). One selected line (HBG3) was tested for its capacity to integrate into developing mouse blastocysts and its capacity for germline transmission.

Example 4

FACS Isolation of HBG3 ES-Cell-Derived Motor Neurons

HBG3 ES-cell embryoid bodies were dissociated using a papain dissociation system (Worthington Biochemical Corp.). Cells expressing high levels of eGFP were sorted from the cell suspension with a Beckman-Coulter Altra flow cytometer, based on their eGFP fluorescence and forward light scatter using the gate indicated in the plot. Typically, 20-30% of input cells expressed high levels of GFP. The analysis established that this eGFP-Hi cell group constituted a >95% pure population of motor neurons. The yield of a typical FACS sort is 3000-5000 GFP-Hi cells per EB.

Example 5

In Vivo Transplantation of HBG3 ES-Cell-Derived Motor Neurons

EBs derived from HBG3 ES cells were induced with 2 μM RA and 1 μM Hh-Ag1.3. At 3-4 days after induction, EBs were partially triturated and implanted into chick HH stage 15-17 spinal cord, which was suction-lesioned to accommodate transplanted tissue. Approximately ½-1 EB equivalent was implanted into a segment spanning 2-5 somites at rostral cervical, caudal cervical, thoracic, or lumbar regions of embryonic chick spinal cord. Some embryos were harvested at 3 days post-transplantation, fixed, sectioned on a vibratome, and stained with antibodies against eGFP and cell- or species-specific antibodies. Other embryos (receiving transplants into thoracic spinal cord) were harvested at 7 days. Their ribcages were dissected and stained as wholemount with rhodamine-conjugated α-bungarotoxin (2 μg/ml, Molecular Probes, Inc.) and antibodies against GFP, Syb, Syn, or VAChT.

Example 6

Directed Differentiation of ES Cells Into LH2-Positive Dorsal Spinal Neurons Embryonic stem (ES) cells were grown on mouse embryonic fibroblasts in ES-cell medium, as described in Example 1. ES-cell colonies were partially dissociated with 0.05% trypsin/EDTA, after 2 days, and cultured in DFNB medium (neurobasal medium (Gibco) mixed with DMEM (Specialty Media, EmbryoMax) and F12 (Gibco), in a 2:1:1 ratio, supplemented with 1×B27 supplement, 0.1 mM 2-mercaptoethanol (Sigma), 2 mM L-glutamine (Gibco), and 1× penicillin/streptomycin (Gibco)) (~$10^5$ cells/ml).

After 2 days in culture, embryoid bodies (EBs) were plated in DFNB medium supplemented with retinoic acid (100 nM to 1 μM) (Sigma). After 1-2 days in culture, in the presence of retinoic acid, EBs were collected, rinsed 2-3 times with PBS, and plated in DFNB medium supplemented with human BMP4 (10 ng/ml; R&D systems) or BMP7 (20 ng/ml). After an additional 4 days in culture, cells were fixed using 4% paraformaldehyde, and processed for immunocytochemistry.

Example 7

Preparation of Inducing Factors

Soluble Wnt3a and control-conditioned medium (Wilson et al., The status of Wnt signaling regulates neural and epidermal fates in the chick embryo. *Nature,* 411:325-30, 2001) were prepared, as previously described (Shibamoto et al., Cytoskeletal reorganization by soluble Wnt-3a protein signalling. *Genes Cells,* 3:659-70, 1998). Soluble Frizzled 8 (mFrz8CRD-IgG) and control-conditioned medium were prepared by transfecting HEK-293 cells with mfz8CRD-IgG (Hsieh et al., Biochemical characterization of Wnt-frizzled interactions using a soluble, biologically active vertebrate Wnt protein. *Proc. Natl. Acad. Sci. USA,* 96:3546-51, 1999) or LacZ reporter construct (Wilson et al., An early requirement for FGF signalling in the acquisition of neural cell fate in the chick embryo. *Curr. Biol.,* 10:421-29, 2000). The transfected HEK-293 cells were then incubated for 48 h in OPTI-MEM medium. mFrzCRD-1gG conditioned medium was used undiluted.

Example 8

Generation of Polyclonal Antibodies

An antibody directed against mouse Sox-1 was produced by immunizing rabbits with a KLH-coupled peptide, obtained from Covance Laboratories Ltd. (North Yorkshire, UK) having the following sequence: CQSRLHSLPQHYQ-GAGAG (SEQ ID NO:1).

Example 9

Immunohistochemistry

Immunohistochemical localization of proteins was performed, as previously described (Yamada et al., Control of cell pattern in the developing nervous system: polarizing activity of the floor plate and notochord. *Cell,* 64:635-47, 1991). Neural precursor (neural progenitor) cells were delineated by expression of rabbit anti-Sox1. Post-mitotic neurons were delineated using mouse anti-Pax6. Otx1/Otx2 and Eng1, which are co-expressed at the midbrain/hindbrain boundary, were used to define cells of a midbrain-like character (Davis and Joyner, Expression patterns of the homeo box-containing genes En-1 and En-2 and the proto-oncogene int-1 diverge during mouse development. *Genes Dev.,* 2:1736-44, 1988). Hox C6 and HoxC8 were used to delineate cells of a spinal-cord character. Krox20 (Covance) is expressed in hindbrain cells, in regions fated to give rise to rhombomeres 3 and 5; thus, co-expression of Sox1 and Otx1/Otx2, in the absence of Eng1 or Krox 20, was used to delineate an anterior/prosencephalic character (Lemaire and Kessel, Gastrulation and homeobox genes in chick embryos. *Mech. Dev.,* 67:3-16, 1997).

Example 10

Suppression and Induction of a Neural Character

In control experiments, 15-30% of cells attained a neural-cell fate when subjected to aggregation in differentiation medium. To suppress a neural-cell fate, medium was supplemented by Wnt3a conditioned medium (1×), BMP4 (10 ng/ml), or SU5402 (5 µM), at the start of ES-cell aggregation (day 0). To induce a neural-cell fate, medium was supplemented by mFRZ8CRD conditioned medium (2×) at the start of ES-cell aggregation (day 0). ES cells were differentiated for 4-8 days.

Example 11

Caudalization of a Neural Character

In control experiments, ES-cell-derived neural precursor cells expressed markers indicative of a forebrain/midbrain cell fate (Otx1/2 and Ent1/2). To caudalize these neural cells progressively, medium was supplemented by Wnt3a conditioned medium (0.5×, 1×, and 2×), 2 days following aggregation (day 2), and cultured for a further 2-6 days. To rostralize neural cells, medium was supplemented with mFRZ8CRD conditioned medium (2×), at start of ES-cell aggregation (day 0), and cultured for a further 2-6 days.

Example 12

Differentiation of Human ES Cells Into Motor Neurons

Human ES (hES) cells may be differentiated using a strategy similar to that employed to differentiate mouse ES cells into motor neurons. The hES-cell protocol has minor modifications from the mouse ES-cell protocol that result, primarily, from the different growth-factor requirements of hES cells, and the slower cell cycle and slower differentiation of hES cells, as compared to mouse ES cells.

In accordance with this modified protocol, human ES cells are expanded in hES-cell medium (e.g., KO-DMEM, 20% KNOCKOUT serum replacement (Invitrogen), 1 mM L-glutamine, 0.1 mM 2-mercaptoethanol, 1% non-essential amino acids, and 4 ng/ml human basic fibroblast growth factor (hbFGF)), on top of feeder cells. To initiate differentiation, hES cells are dissociated, and then plated in non-adherent culture dishes, in the presence of differentiation medium (hES-cell medium without FGF). Under these conditions, hES cells reaggregate and form floating spheres, or embryoid bodies (EBs). After ~6 days, the EBs are collected.

The EBs are plated in non-adherent culture dishes, in the presence of induction medium containing DMEM:F12:neurobasal medium (Invitrogen), in a 1:1:2 ratio, supplemented with all trans retinoic acid (1 µM), HhAg1.3 (1 µM), and knockout serum replacement (10%; Invitrogen) or B27 (1×; Invitrogen) supplement. The EBs are maintained in the induction medium for an additional ~12 days. After a total of ~18 days of differentiation, EBs contain a mixture of cells, including differentiated human motor neurons.

Summarized below are results obtained by the inventors in connection with the experiments of the above Examples. The results of the inventors' experiments indicate that retinoic acid has a caudalizing effect on neural progenitor cells in embryoid bodies (EBs), that motor neuron progenitor specification is hedgehog-dependent in caudalized EBs, that eGFP-labeled, ES-cell-derived neurons may be successfully generated and isolated, and that eGFP-labeled, ES-cell-derived motor neurons will differentiate in embryonic spinal cord.

RA Caudalizes Neural Progenitor Cells in Embryoid Bodies

To begin to examine the capacity of mouse ES cells to generate motor neurons, the inventors grew mouse ES cells in aggregate culture for 2 days, a procedure that results in the formation of embryoid bodies (EBs) (Bain et al., Embryonic stem cells express neuronal properties in vitro. *Dev. Biol.,* 168:342-57, 1995). EBs consisting initially of ~1000 cells were maintained in suspension culture for a further 1-7 days, in the presence or absence of added factors.

Under control conditions, EBs grown for 2-3 days contained few, if any, cells that expressed the pan-neural progenitor marker, Sox1 (FIG. 1B) (Pevny et al., Generation of purified neural precursors from embryonic stem cells by lineage selection. *Curr. Biol.,* 8:971-74, 1998; Wood et al., Comparative expression of the mouse Sox1, Sox2 and Sox3 genes from pre-gastrulation to early somite stages. *Mech. Dev.,* 86:197-201, 1999). Similarly, EBs examined at 5 days contained few, if any, neurons, assessed by expression of the neuronal nuclear marker, NeuN, and the neuronal β-tubulin isoform recognized by MAb TuJ1 (FIG. 1B and data not shown). In contrast, exposure of EBs to RA (100 nM to 2 µM) for 2-3 days resulted in the presence of many Sox1$^+$ cells (FIG. 1B); by 5 days, many NeuN$^+$, TuJ1$^+$ post-mitotic neurons were detected (FIG. 1B and data not shown). Thus, EBs derived from mouse ES cells can be induced to generate neurons. See, also, Bain et al., Embryonic stem cells express neuronal properties in vitro. *Dev. Biol.,* 168:342-57, 1995; and Xian et al., Peering into early neurogenesis with embryonic stem cells. *Trends Neurosci.,* 24:685-86, 2001).

The inventors next determined the rostrocaudal positional identity of the neural progenitor cells formed in RA-exposed EBs, by assaying expression of Otx2 and En1 —the co-expression of which is indicative of early midbrain positional identity (Davis et al., Expression patterns of the homeobox-containing genes En-1 and En-2 and the proto-oncogene int-1 diverge during mouse development. *Genes Dev.,* 2:1736-44, 1988; Mallamaci et al., OTX2 homeoprotein in the developing central nervous system and migratory cells of the olfactory area. *Mech. Dev.,* 58:165-78, 1996)- and the expression of Hox proteins Hoxc5, Hoxc6, and Hoxc8, which are markers of spinal cord positional identity (Belting et al., Multiple phases of expression and regulation of mouse Hoxc8 during early embryogenesis. *J. Exp. Zool.,* 282:196-222, 1998; Liu et al., Assigning the positional identity of spinal motor neurons. Rostrocaudal patterning of Hox-c expression by FGFs, Gdf11, and retinoids. *Neuron,* 32:997-1012, 2001). Cells in EBs exposed to RA for 3 days lacked Otx2 and En1 expression, and expressed Hoxc5 and Hoxc6, but not Hoxc8 (FIG. 1B and data not shown). This profile of neural Hox-c expression is indicative of cells with a rostral cervical spinal positional character (Belting et al., Multiple phases of expression and regulation of mouse Hoxc8 during early embryogenesis. *J. Exp. Zool.,* 282:196-222, 1998; Liu et al., Assigning the positional identity of spinal motor neurons. Rostrocaudal patterning of Hox-c expression by FGFs, Gdf11, and retinoids. *Neuron,* 32:997-1012, 2001).

Since exposure of ES cells to RA promotes both neural differentiation and the expression of spinal positional markers, this protocol does not permit a direct test of the caudalizing action of RA on ES-derived neural cells. Therefore, the inventors sought a means of neuralizing ES cells through an RA-independent pathway. To achieve this, the inventors used the PA6 stromal cell line as a source of neural inductive signals (Kawasaki et al., Induction of midbrain dopaminergic neurons from ES cells by stromal cell-derived inducing activity. *Neuron,* 28:31-40, 2000). Exposure of mouse ES cells to PA6 cell activity for 5 days induced numerous Sox1$^+$ cells, many of which co-expressed Otx2 and En1; in contrast, no cells expressed Hoxc5 or Hoxc6 (FIG. 1C and data not shown). Furthermore, by the sixth day, many Otx2$^+$, TuJ1$^+$ neurons were detected (FIG. 1C). Joint exposure of ES cells to PA6 cell activity and RA (2 μM) still induced many Sox1$^+$ cells; however, these cells lacked Otx2 and En1 expression, and many now expressed Hoxc5 and Hoxc6 (FIG. 1C and data not shown). Take together, these findings indicate that, as in vivo (Muhr et al., Convergent inductive signals specify midbrain, hindbrain, and spinal cord identity in gastrula stage chick embryos. *Neuron,* 23:689-702, 1999), neuralized ES cells of an initial midbrain-like positional character can be caudalized to a spinal-like positional character upon exposure to RA.

Figure 2:
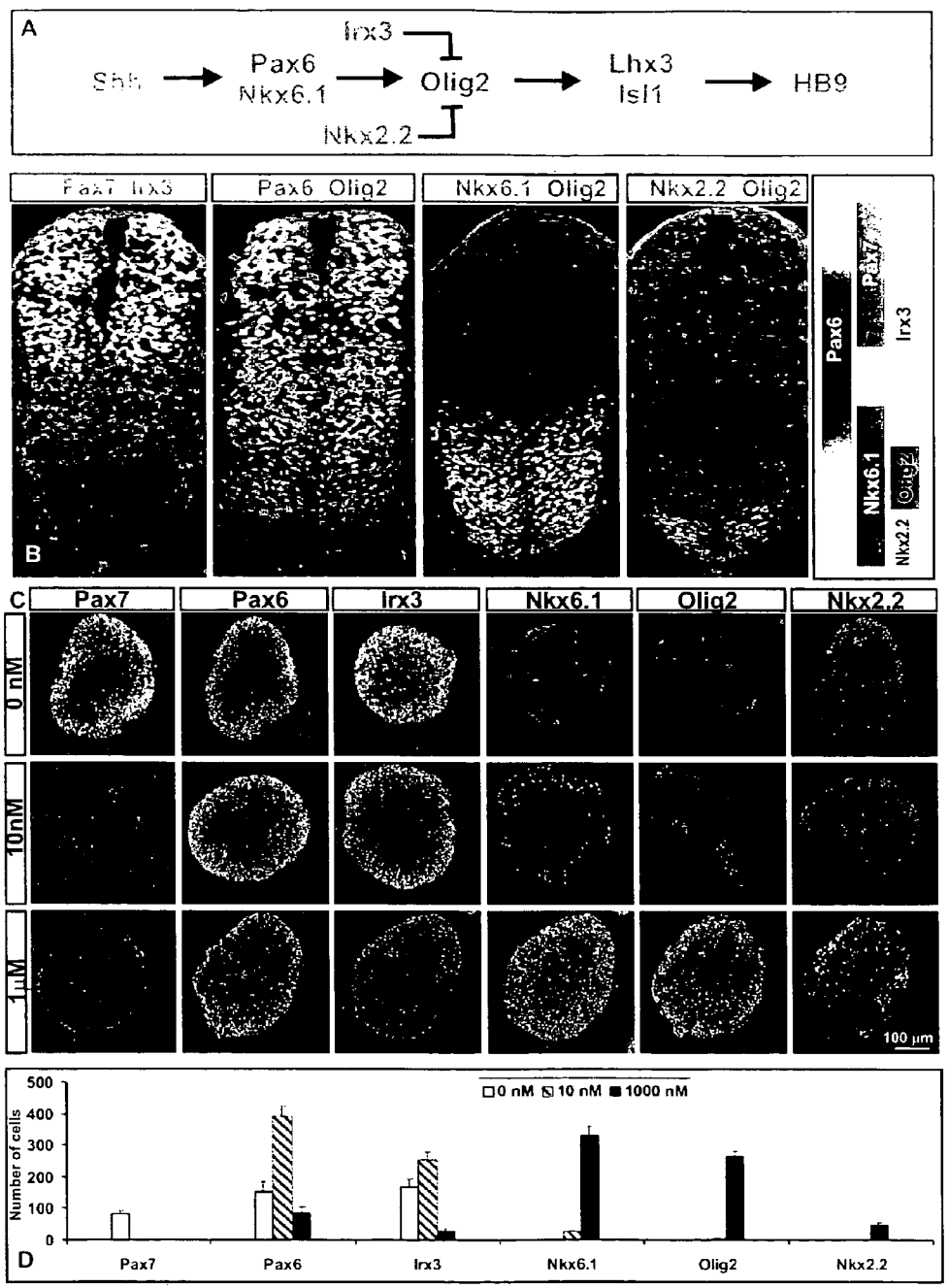
FIG. 2 illustrates hedgehog-dependent ventralization of neural progenitor cells in embryoid bodies (EBs). (A) Schematic outline of the SHh-activated transcriptional pathway of spinal motor neuron generation. The proteins that inhibit motor neuron generation are Irx3 and Nkx2.2. The remaining proteins are required for motor neuron generation. (B) Patterns of expression of HD and bHLH transcription factors in the caudal neural tube of E9.5 mouse embryos. The progenitor domain giving rise to motor neurons was marked by the co-expression of Olig2, Nkx6.1, and low levels of Pax6. (C) Profile of transcription factor expression in ES-cell-derived EBs grown for 3 days, either in the presence of RA (2 μM) alone or with 10 nM or 1 μM Hh-Ag1.3. (D) Quantification of transcription factor expression in EBs in the presence of RA and different concentrations of Hh-Ag1.3. Depicted are mean± s.e.m. values, per section, from 8 EBs assayed for each condition.

Motor Neuron Progenitor Specification is Hh-Dependent in Caudalized Embryoid Bodies To examine whether the neural progenitors with spinal positional character, which were present in RA-exposed EBs, can differentiate into motor neuron progenitors, the inventors monitored the expression of HD and bHLH transcription factors that define progressive steps in the specification of motor neuron progenitor identity (FIG. 2A). The expression of Pax7, Irx3, Dbx1, Pax6, Nkx6.1, Nkx2.2, and Olig2 delineated distinct sets of neural progenitor cells positioned along the dorso-ventral axis of the neural tube (Briscoe et al., Specification of neuronal fates in the ventral neural tube. *Curr. Opin. Neurobiol.,* 11:43-49, 2001; FIG. 2B). Spinal motor neuron progenitors were found within the pMN domain; they expressed Pax6, Nkx6.1, and Olig2, and excluded Pax7, Irx3, Dbx1, and Nkx2.2 (FIG. 2B and data not shown). EBs exposed to RA for 3 days contained many cells that expressed Pax7, Pax6, Irx3, and Dbx1, and few, if any, cells that expressed Nkx6.1, Olig2, or Nkx2.2 (FIGS. 2C and 2D and data not shown). This profile of transcription factor expression is characteristic of progenitor cells located in the dorsal and intermediate spinal cord that give rise to interneurons (FIG. 2B) (Lee et al., The specification of dorsal cell fates in the vertebrate central nervous system. *Annu. Rev. Neurosci.,* 22:261-94, 1999).

The induction of motor neuron progenitors depends on SHh activity (Briscoe et al., Specification of neuronal fates in the ventral neural tube. *Curr. Opin. Neurobiol.,* 11:43-49, 2001). Therefore, the inventors examined whether SHh signalling changes the profile of progenitor cell transcription factor expression in RA-exposed EBs. To activate the SHh signalling pathway, the inventors used a specific small molecule agonist of SHh signalling, Hh-Ag1.3 (Frank-Kamenetsky et al., Chemical genetics of Hh signaling: Identification and characterization of Smoothened agonists and antagonists. *Submitted,* 2002), or recombinant SHh-N protein (Roelink et al., Floor plate and motor neuron induction by different concentrations of the amino-terminal cleavage product of sonic hedgehog autoproteolysis. *Cell,* 81:445-55, 1995), with essentially identical results.

Figure 10:
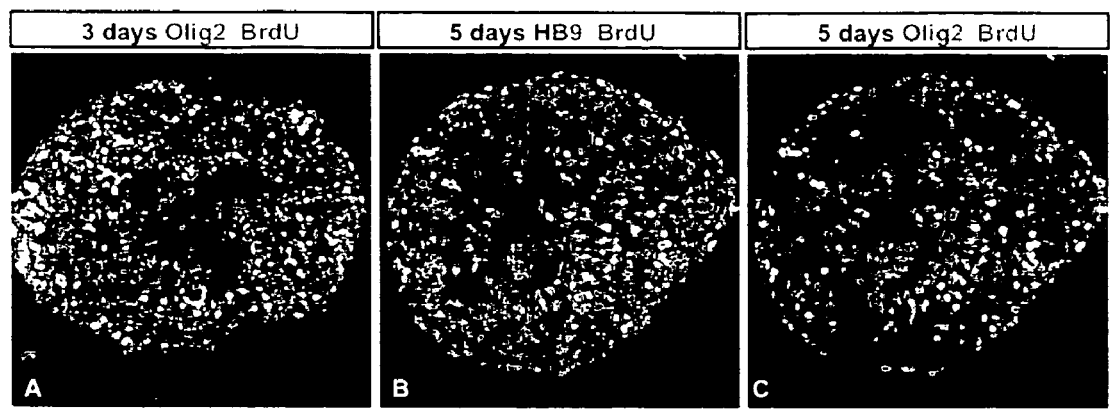
FIG. 10 shows that motor neuron progenitors in EBs incorporate BrdU. (A-C) BrdU labeling (20 μg/ml) for 1 h before fixation revealed large numbers of BrdU$^+$, Olig2$^+$ progenitors in EBs grown for 3 days in the presence of RA and Hh-Ag1.3. HB9$^+$ motor neurons in EBs grown for 5 days did not incorporate BrdU (B), but a small number of BrdU$^+$, Olig2$^+$ progenitors were still present (C).
Figure 11:
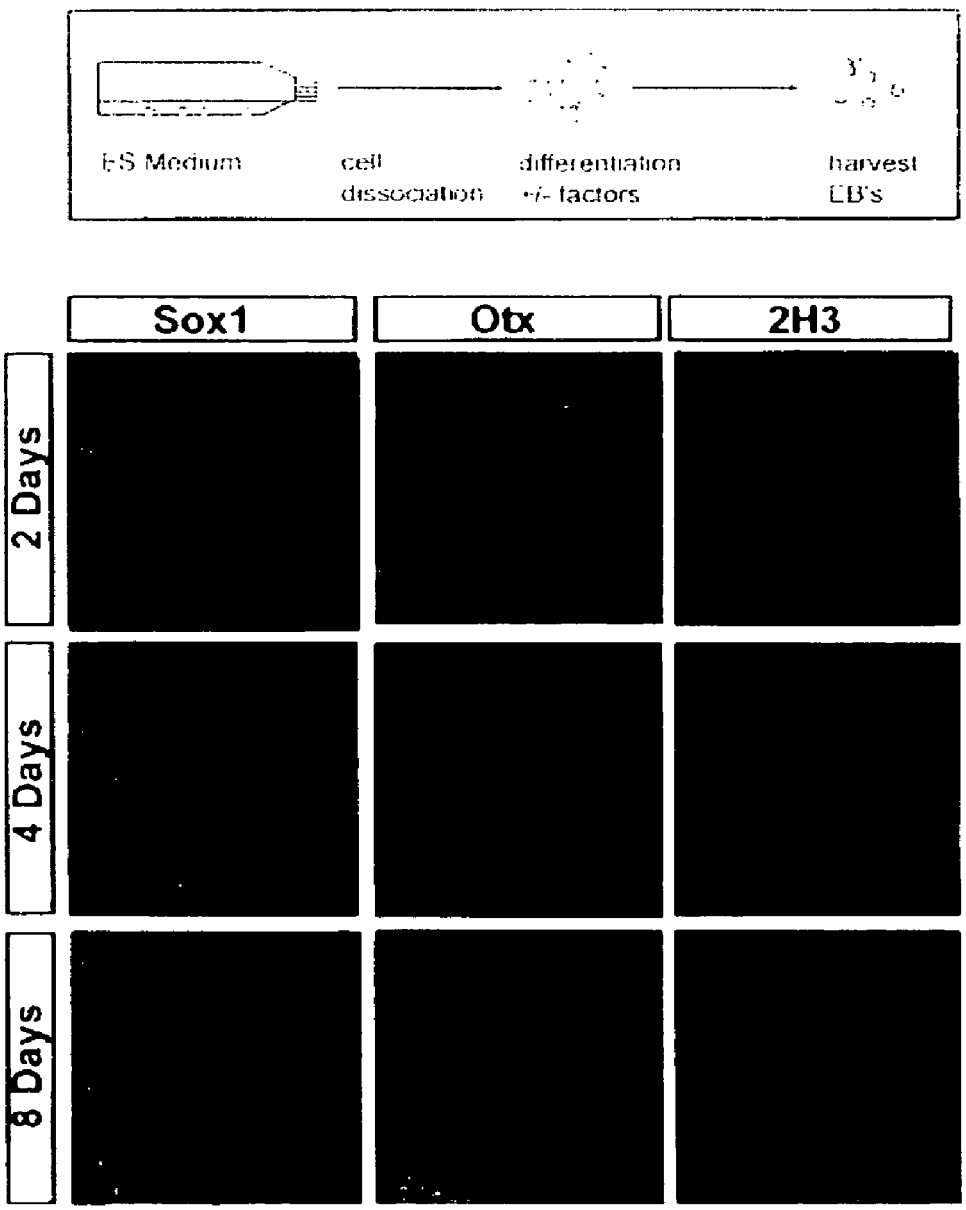
FIG. 11 shows that embryonic stem (ES) cells can acquire a neural-cell fate during differentiation. The top panel sets forth a schematic representation of experimental methods. ES cells were grown in the presence of ES medium containing LIF. Cells were then dissociated, and allowed to differentiate in the absence of LIF (differentiation medium). During this time, the cells aggregated to form embryoid bodies (EBs). Factors were added to the medium at different times during the culture; the cells were then harvested at 2, 4, or 8 days of culture. The bottom panel illustrates ES cells that acquired a neural-cell fate. EBs were grown in the presence of differentiation medium, harvested at 2, 4, and 8 days of differentiation, and analyzed for the expression of the following markers: Sox1 (neural precursor/progenitor), Otx (anterior neural (prospective forebrain and midbrain)), and 2H3 (post-mitotic neural). Cells within the culture acquired a neural precursor (progenitor) cell fate by 4 days of differentiation. Images were taken using the Zeiss axiovert 200 M microscope, with a 20× objective.
Figure 12:
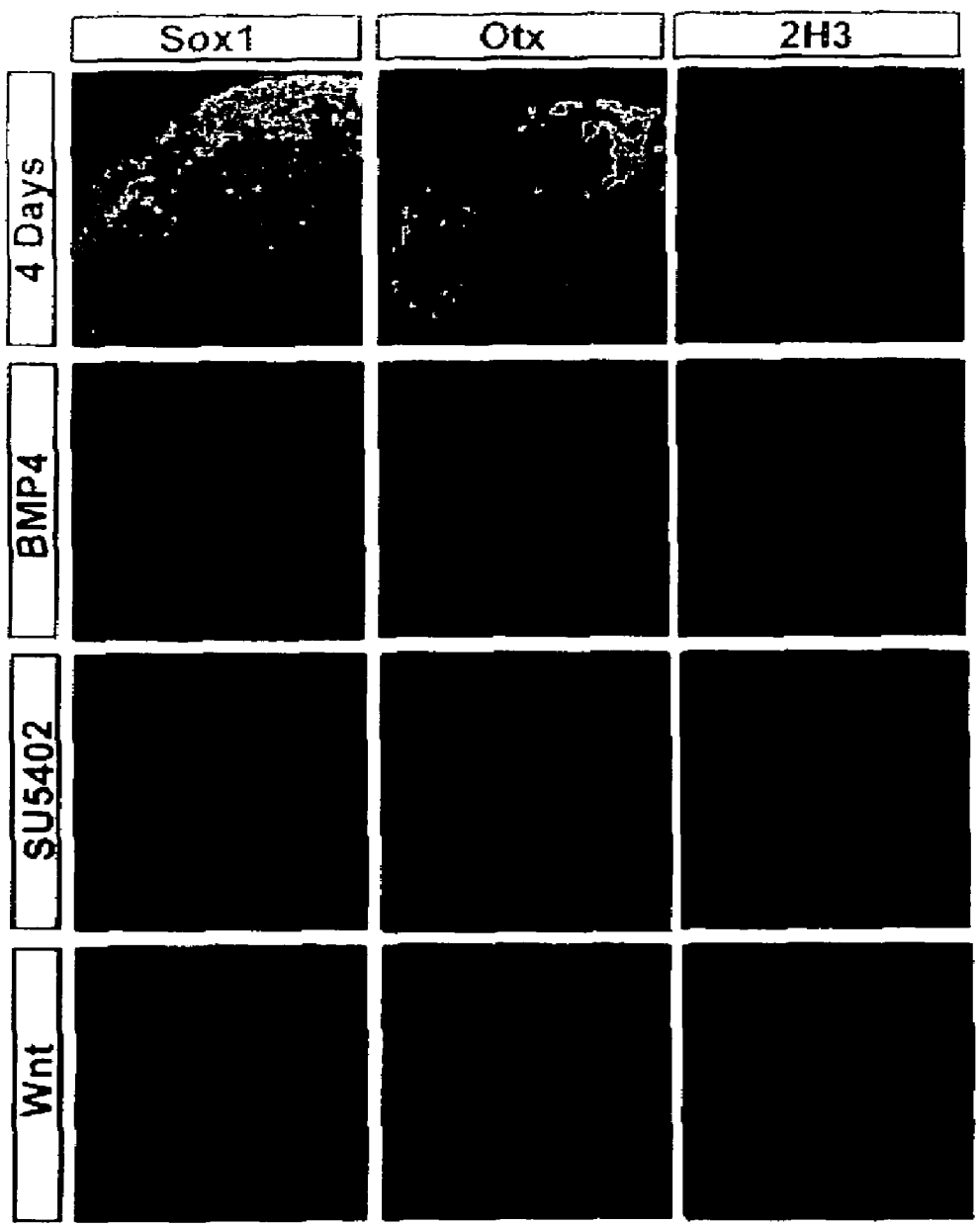
FIG. 12 demonstrates that attenuation of FGF signalling, or exposure to BMP (bone morphogenetic protein) or Wnt signalling, blocks neural-cell fate of ES cells. EBs were differentiated for 4 days in differentiation medium alone, or in differentiation medium supplemented with BMP4 protein, an FGF signalling inhibitor (SU5402), or Wnt3a. Cells within the culture could not acquire a neural precursor cell fate by 4 days of differentiation, when in the presence of the appropriate concentration of BMP4, SU5402, or Wnt3a for the entire duration of the culture. Images were taken using the Zeiss axiovert 200 M microscope, with a 20× objective. Sox1=neural precursor/progenitor marker; Otx=anterior neural (prospective forebrain and midbrain) marker; 2H3=post-mitotic neural marker
Figure 13:
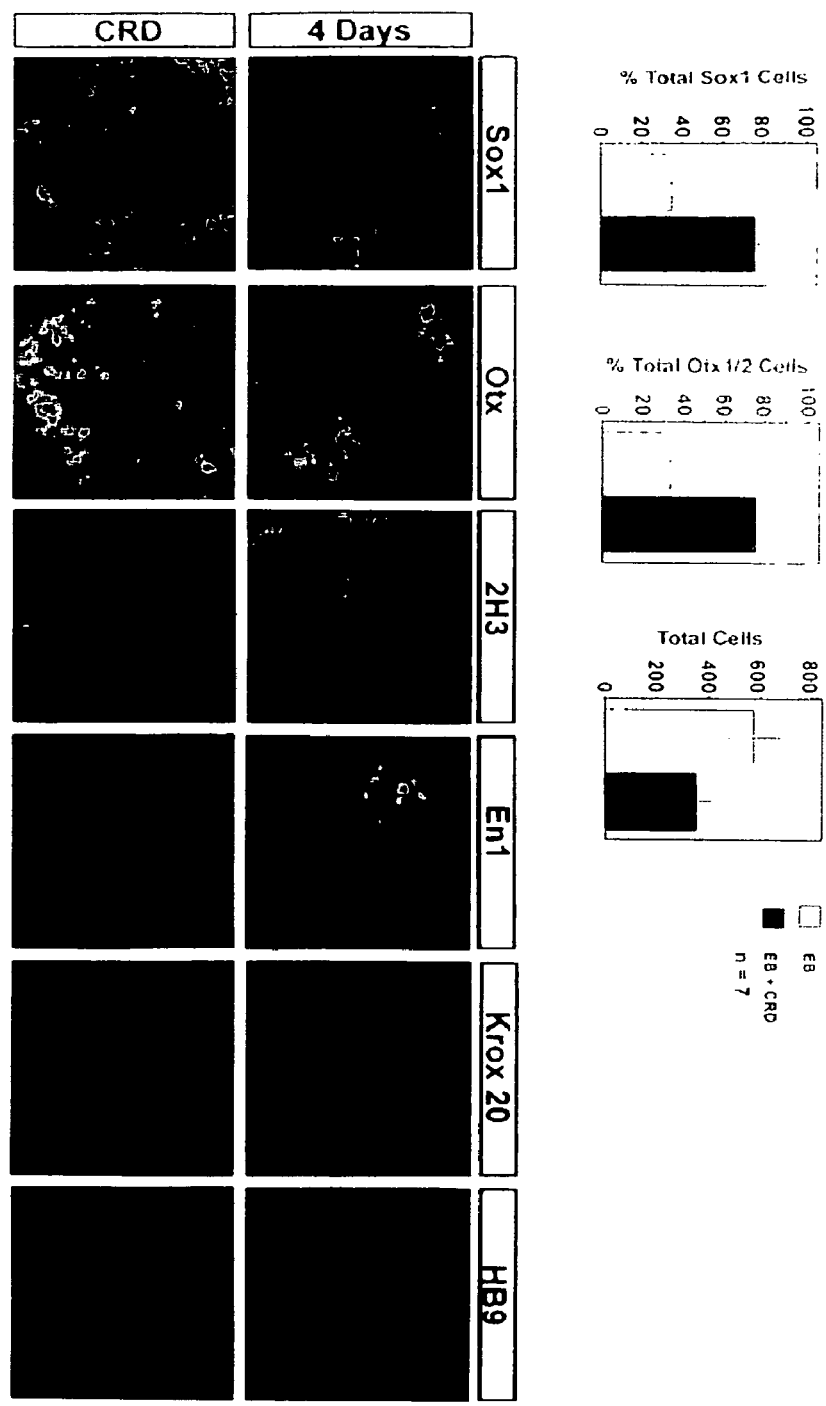
FIG. 13 shows that inhibition of Wnt signalling increases the proportion of Sox1$^+$ and Otx½$^+$ cells, and prevents the appearance of En½$^+$ cells. EBs were differentiated for 4 days in differentiation medium alone, or in differentiation medium supplemented with CRD—the cystein rich domain of the truncated Frizzled 8 receptor, which binds and sequesters Wnt protein, and, therefore, acts to attenuate Wnt signaling. As demonstrated by the panel at the left, EBs acquired a neural precursor cell fate that was anterior in character (specifically, the forebrain and midbrain, as evidenced by the expression of Otx and En1 (prospective midbrain)), when grown in control conditions. When EBs were differentiated in the presence of CRD, a higher proportion of cells became neural precursor cells (Sox1$^+$); the appearance of En1$^+$ cells (midbrain) was blocked, thereby indicating that these cells had been anteriorized. The graphs at the right represent the cell counts for this process. Gray represents control conditions, and black represents cells cultured in the presence of CRD. Krox20 is a marker for hindbrain cells, and HB9 is a marker for motor neurons. Images were taken using the Zeiss axiovert 200 M microscope, with a 20× objective. Sox1=neural precursor/progenitor marker; Otx=anterior neural (prospective forebrain and midbrain) marker; 2H3=post-mitotic neural marker
Figure 14:
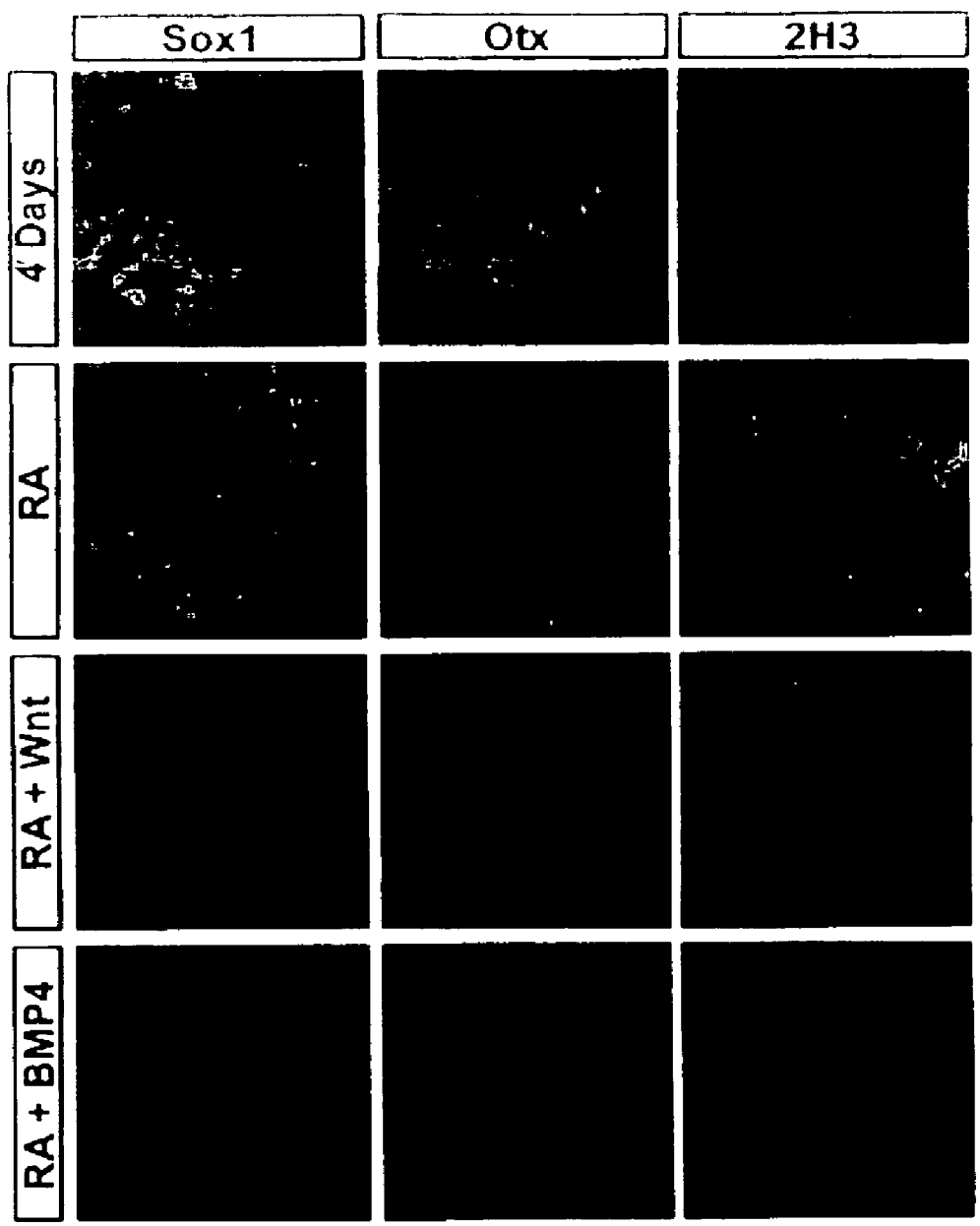
FIG. 14 illustrates that BMP or Wnt signalling blocks RA-induced neural cells. EBs were differentiated for 4 days in differentiation medium alone, or in differentiation medium supplemented with RA (retinoic acid), RA+Wnt3a, or RA+BMP4. In control conditions, EBs acquired a neural precursor cell fate. In the presence of RA, a higher proportion of cells expressed the neural precursor marker, Sox1. These neural cells became caudal (as evidenced by loss of Otx expression), and a higher proportion of cells were post-mitotic (as evidenced by 2H3 expression). When the EBs were cultured in the presence of RA+Wnt3a or RA+BMP4, no neural precursor or post-mitotic neural cells were present. These results indicate that Wnt3a and BMP4 block RA-induced and endogenous neural cells. Images were taken using the Zeiss axiovert 200 M microscope, with a 20× objective. Sox1=neural precursor/progenitor marker; Otx=anterior neural (prospective forebrain and midbrain) marker; 2H3=post-mitotic neural marker FIG. 15 demonstrates that exposure of ES cells to Wnt signalling, after 2 days of differentiation, results in caudalization of neural cells. A schematic representation of the expression pattern of neural markers is shown in the top panel. Solid lines represent the anterior/posterior region of expression within the developing nervous system for each marker. As shown in the bottom panel, EBs were differentiated for 4 days in differentiation medium alone, or in differentiation medium supplemented with Wnt3a. In control conditions, EBs acquired a neural precursor cell fate that was anterior in character (forebrain and midbrain). When EBs are differentiated in the presence of different concentrations of Wnt3a and/or are exposed at different times to Wnt3a, the cells within the culture become progressively caudalized to hindbrain and spinal cord character. Non-neural caudal cells may also be induced under these conditions. Here, EBs were cultured for 2 days in differentiation medium, and then cultured for a further 2 days in differentiation medium supplemented with Wnt3a. Pax6 is a marker for forebrain and spinal cord cells; HoxC5 is a marker for spinal cord/caudal non-neural cells; HoxC8 is a marker for spinal cord/caudal non-neural cells; and HoxC9 is a marker for spinal cord/caudal non-neural cells. Images were taken using the Zeiss axiovert 200 M microscope, with a 20× objective. C=cervical; B=brachial; T=thoracic; L=lumbar; Sox1=neural precursor/progenitor marker; Otx=anterior neural (prospective forebrain and midbrain) marker; 2H3=post-mitotic neural marker; Krox20=marker for hindbrain cells; HB9=marker for motor neurons
Figure 15:
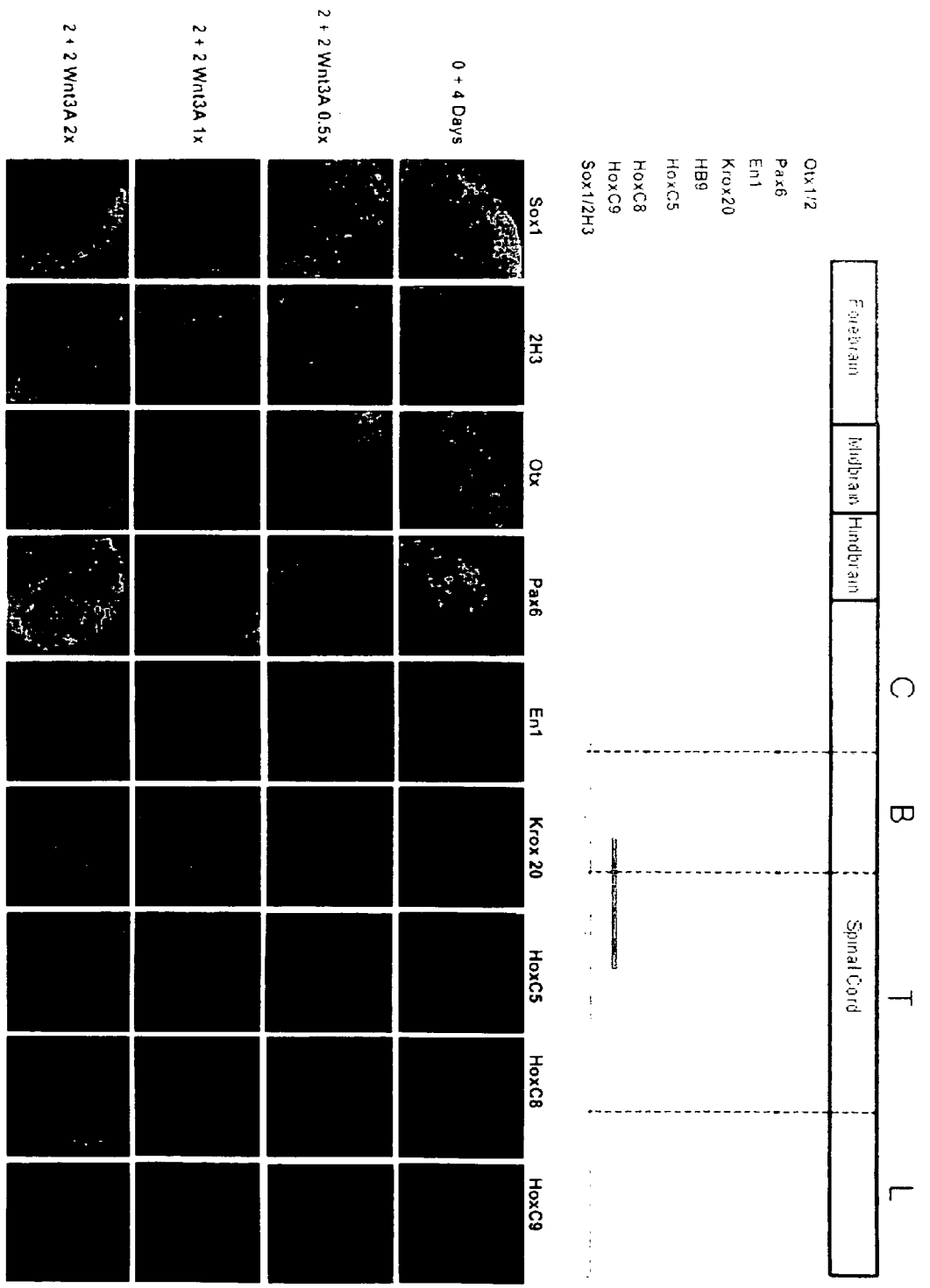
Figure 16:
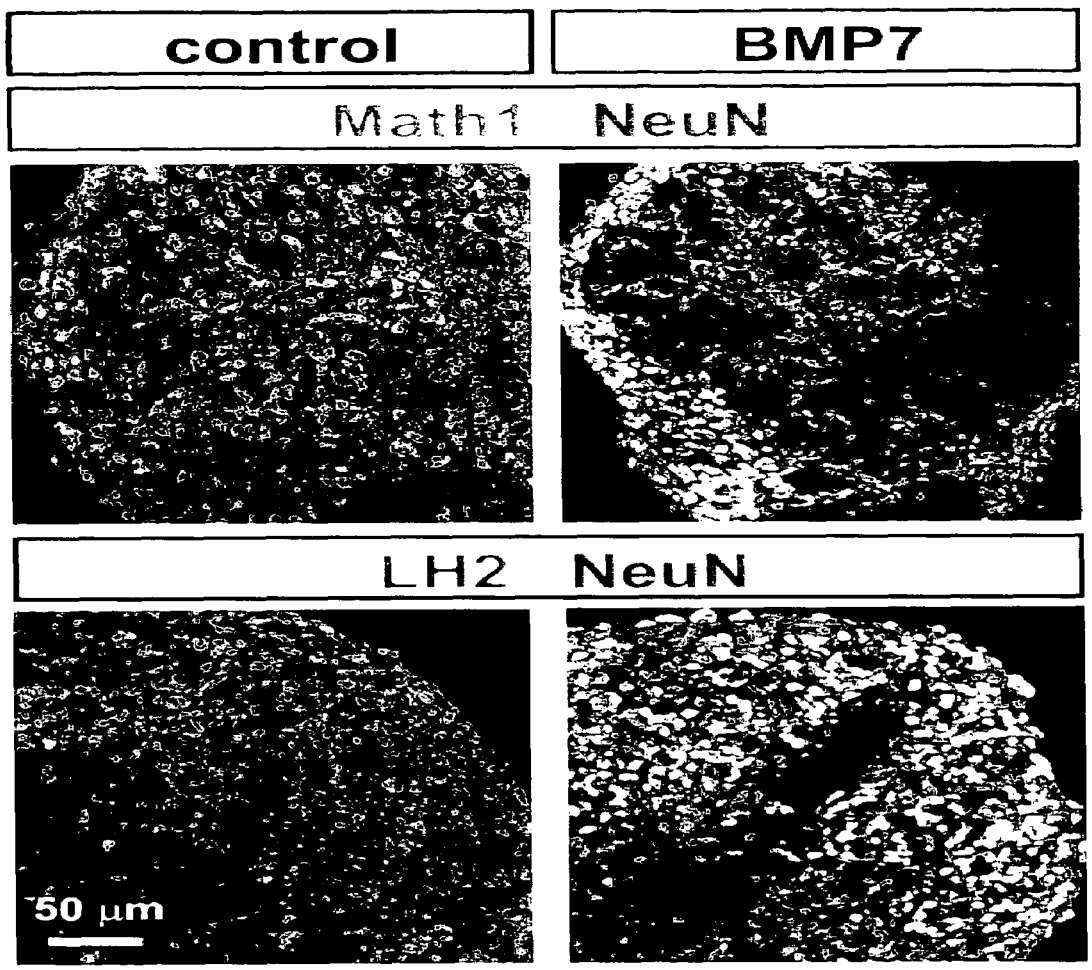
FIG. 16 shows that mouse ES cells differentiate into dorsal spinal neurons when grown in the presence of BMPs. Differentiated embryoid bodies were stained with antibodies against pan-neuronal marker NeuN, and with antibodies against markers expressed in a subset of dorsal spinal neurons (LH2) and their progenitors (Math 1). Immunoreactive cells were revealed by fluorescently-labeled secondary antibodies, and images were acquired using a confocal microscope. ES cells grown in control conditions did not differentiate into dorsal spinal neurons (absence of Math1 and LH2 expression). In contrast, numerous dorsal neurons and their progenitors were observed in embryoid bodies grown in the presence of BMP7. Images were taken using the Zeiss axiovert 200 M microscope, with a 20× objective.

Exposure of RA-treated EBs to 10 nM Hh-Ag1.3 for 3 days resulted in a marked change in the profile of transcription factor expression. Pax7 expression was completely repressed, the number of Pax6$^+$ and Irx3$^+$ cells was increased, the number of Dbx1$^+$ cells was reduced, and a few Nkx6.1$^+$ and Olig2$^+$ cells were detected (FIGS. 2C and 2D and data not shown). Exposure of RA-treated EBs to 1 μM Hh-Ag1.3 virtually eliminated Dbx1 expression, markedly reduced the number of Irx3$^+$ and Pax6$^+$ cells, and induced a large increase in the number of Nkx6$^+$ and Olig2$^+$ cells (FIGS. 2C and 2D). Many of the Olig2$^+$ cells in Hh-Ag1.3-exposed EBs incorporated BrdU (FIG. 10), indicating that they were cycling progenitors. At this concentration of Hh-Ag1.3, a few Nkx2.2$^+$ cells were also induced (FIGS. 2C and 2D), but no HNF3β$^+$ floor plate cells were detected (data not shown). The dorsal-to-ventral shift in the profile of expression of progenitor cell transcription factor markers in EBs in response to Hh signalling closely resembles the behavior of neural tube progenitors (Ericson et al., Two critical periods of Sonic Hedgehog signaling required for the specification of motor neuron identity. *Cell,* 87:661-73, 1996; Ericson et al., Pax6 controls progenitor cell identity and neuronal fate in response to graded SHh signaling. *Cell,* 90:169-80, 1997; Briscoe et al., A homeodomain protein code specifies progenitor cell identity and neuronal fate in the ventral neural tube. *Cell,* 101:435-45, 2000). In particular, high levels of SHh signalling generated many cells that expressed a profile of HD and bHLH protein expression characteristic of motor neuron progenitors.

Figure 3:
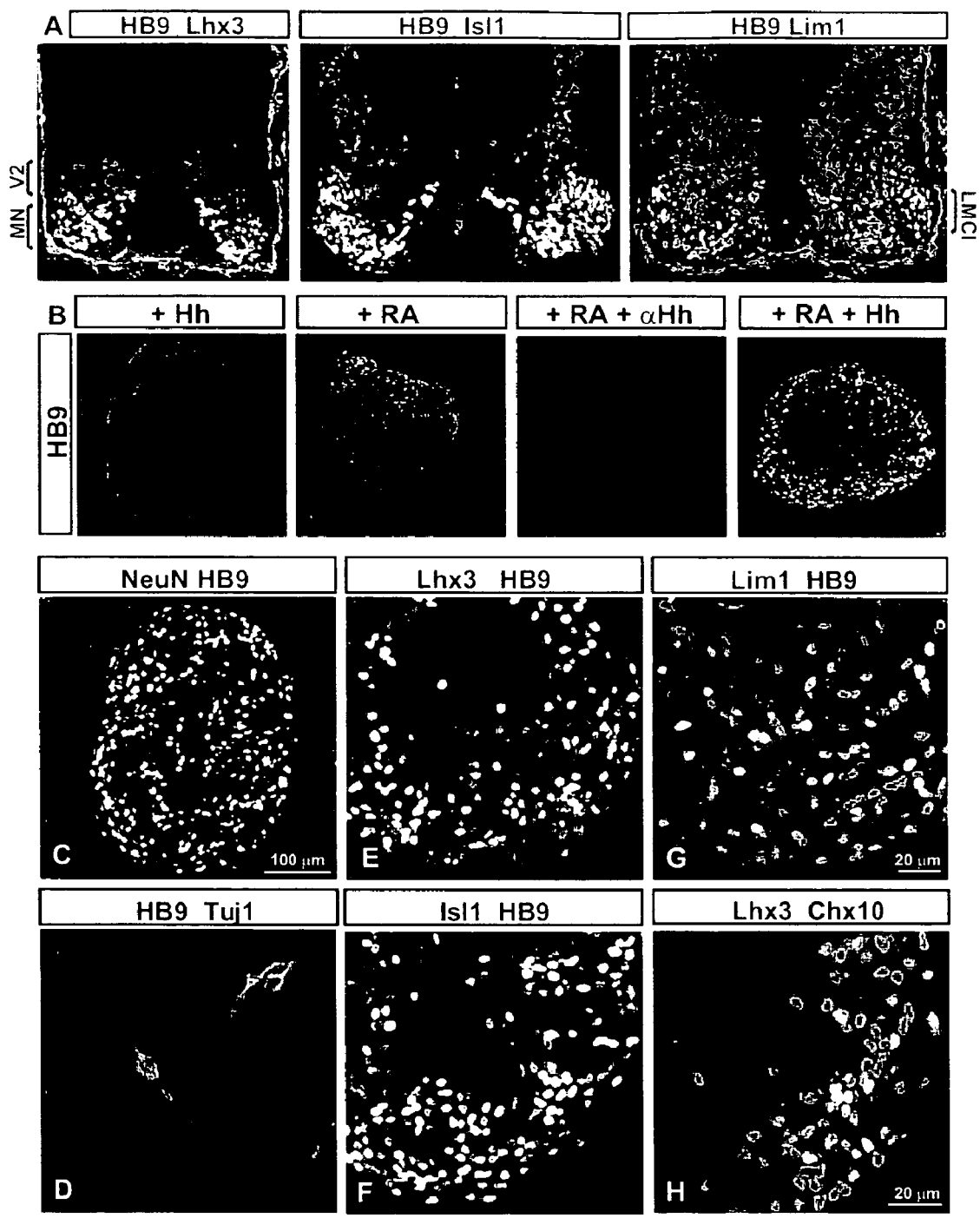
FIG. 3 depicts expression of motor neuron and interneuron transcription factors in embryoid bodies (EBs). (A) Co-expression of HB9 and Lhx3 defined newly-generated motor neurons. Lhx3 alone was expressed by V2 interneurons. Co-expression of HB9 and Isl1 defined subsets of motor neurons. Some lateral motor column (LMC) neurons expressed high levels of HB9 in the absence of Isl1; in contrast, other LMC neurons expressed Isl1, but only expressed HB9 at very low levels. Isl1 was also expressed by some dorsal interneurons. Co-expression of HB9 and Lim1 defined lateral LMC neurons. Many interneurons also expressed Lim1. (B) EBs grown for 5 days in the presence of Hh-Ag1.3 (1 μM), but not RA, did not contain HB9$^+$ neurons. EBs grown for 5 days in the presence of RA (2 μM), but not Hh-Ag1.3, contained a small number of HB9$^+$ neurons. EBs grown for 5 days in the presence of RA and anti-Hh antibody (mAb 5E1; 30 μg/ml) did not contain HB9$^+$ neurons. EBs grown for 5 days in the presence of RA and recombinant SHh-N (300 nM) contained many HB9$^+$ neurons. (C) Co-expression of HB9 and NeuN in neurons in EBs grown for 5 days in the presence of RA and Hh-Ag1.3 (1 μM). (D) Localization of HB9 in the nucleus of a TuJ1$^+$ neuron, obtained by dissociation of EBs grown for 5 days in the presence of RA, and cultured for a further 2 days. Other neurons that lacked HB9 expression were also present. (E) Co-expression of HB9 and Lhx3 in neurons in EBs grown for 5 days in the presence of RA and Hh-Ag1.3 (1 μM). Cells that expressed Lhx3 alone were V2 interneurons. (F) Co-expression of HB9 and Isl1 in motor neurons in EBs grown for 5 days in the presence of RA and Hh-Ag1.3 (1 μM). (G) HB9 and Lim1 were co-expressed in a small number of neurons in EBs grown for 5 days in the presence of RA and Hh-Ag1.3 (1 μM). Cells that expressed Lim1 alone were interneurons. (H) Co-expression of Chx10 and Lhx3 in V2 interneurons in EBs grown for 5 days in the presence of RA and Hh-Ag1.3 (1 μM).

To determine whether motor neurons were generated from the caudalized and ventralized progenitor cells present in RA- and Hh-exposed EBs, the inventors analyzed the expression of HB9, an HD protein expressed selectively and persistently by somatic motor neurons (Pfaff et al., Requirement for LIM homeobox gene Isl1 in motor neuron generation reveals a motor neuron-dependent step in interneuron differentiation. *Cell,* 84:309-20, 1996; Arber et al., Requirement for the homeobox gene Hb9 in the consolidation of motor neuron identity. *Neuron,* 23:659-764, 1999; Thaler et al., Active suppression of interneuron programs within developing motor neurons revealed by analysis of homeodomain factor HB9. *Neuron,* 23:675-87, 1999) (FIG. 3A). RA-exposed EBs grown alone for 5 days did contain a few HB9$^+$ neurons (FIG. 3B; 7±2 HB9$^+$ neurons/section). To test whether these neurons were generated in a Hh-dependent manner, the inventors grew RA-exposed EBs in the presence of a function-blocking anti-Hh antibody (mAb 5E1 Ig, 30 μg/ml) (Ericson et al., Two critical periods of Sonic Hedgehog signaling required for the specification of motor neuron identity. *Cell,* 87:661-73, 1996). RA-exposed EBs grown in the presence of anti-Hh contained no HB9$^+$ neurons (FIG. 3B), indicating that an endogenous source of Hh is required for the differentiation of the few motor neurons found in RA-exposed EBs.

The inventors also examined whether the efficiency of motor neuron generation can be enhanced by elevating the level of Hh signalling in RA-exposed EBs. Exposure of RA-treated EBs to SHh (300 nM) or Hh-Ag1.3 (1 μM) resulted in a marked increase in the number of motor neurons generated: typically, 20-30% of cells in these EBs expressed HB9 (~5000 HB9$^+$ neurons; 509±57 HB9$^+$ neurons/section; ~10-15 sections per EB) (FIG. 3B and data not shown). These HB9$^+$ cells co-expressed NeuN and TuJ1 (FIGS. 3C and 3D), and did not incorporate BrdU (FIG. 10), indicating that they are post-mitotic neurons. No HB9+ neurons were generated in EBs treated with Hh-Ag1.3 (1 µM) for 5 days without RA exposure (FIG. 3B). Thus, the generation of motor neurons in EBs depends on both the caudalizing action of RA and the ventralizing action of Hh signals.

To assess the molecular character of post-mitotic motor neurons in more detail, the inventors examined the expression of 3 LIM HD proteins that are expressed by subsets of spinal motor neurons: Isl1, Lhx3, and Lim1 (Tsuchida et al., Topographic organization of embryonic motor neurons defined by expression of LIM homeobox genes. *Cell,* 79:957-70, 1994; Sharma et al., LIM homeodomain factors Lhx3 and Lhx4 assign subtype identities for motor neurons. *Cell,* 95:817-28, 1998; Kania et al., Coordinate roles for LIM homeobox genes in directing the dorsoventral trajectory of motor axons in the vertebrate limb. *Cell,* 102:161-73, 2000) (FIG. 3A). All three LIM HD proteins were expressed by HB9+ motor neurons in RA- and Hh-exposed EBs. Over 70% of HB9+ motor neurons co-expressed Isl1 and Lhx3 (FIGS. 3E and 3F), but a much smaller fraction (<5%) co-expressed Lim1 (FIG. 3G). No HB9+ neurons co-expressed Phox2b (data not shown), a marker of hindbrain visceral motor neurons (Pattyn et al., Control of hindbrain motor neuron differentiation by the homeobox gene Phox2b. *Development,* 127:1349-58, 2000). The low proportion of motor neurons that co-expressed HB9 and Lim1—a profile indicative of lateral motor column (LMC) neurons (Kania et al., Coordinate roles for LIM homeobox genes in directing the dorsoventral trajectory of motor axons in the vertebrate limb. *Cell,* 102:161-73, 2000)—was consistent with the rostral cervical identity of motor neurons, revealed by the profile of Hox-c protein expression (Belting et al., Multiple phases of expression and regulation of mouse Hoxc8 during early embryogenesis. *J. Exp. Zool.,* 282:196-222, 1998; Liu et al., Assigning the positional identity of spinal motor neurons. Rostrocaudal patterning of Hox-c expression by FGFs, Gdf11, and retinoids. *Neuron,* 32:997-1012, 2001).

Since SHh acts in a graded manner, ventral interneurons are induced at concentrations only slightly below that sufficient for motor neuron generation (Briscoe and Ericson, Specification of neuronal fates in the ventral neural tube. *Curr. Opin. Neurobiol.,* 11(1):43-49,2001). Therefore, the inventors examined whether ventral interneurons are also generated in RA-treated EBs exposed to 1 µM Hh-Ag1.3. Both Lhx3+, Chx10+ V2 interneurons and Lim1/2+ (likely V0 and V1) interneurons were detected in these EBs (FIGS. 3G and 3H and data not shown). Thus, as with primary neural tissue (Briscoe and Ericson, Specification of neuronal fates in the ventral neural tube. *Curr. Opin. Neurobiol.,* 11 (1):43-49, 2001), small variations in the level of Hh signalling to which cells in EBs are exposed results in the generation of both ventral interneurons and spinal motor neurons.

eGFP-Labeled, ES-Cell-Derived Motor Neurons May be Generated and Isolated

Figure 4:
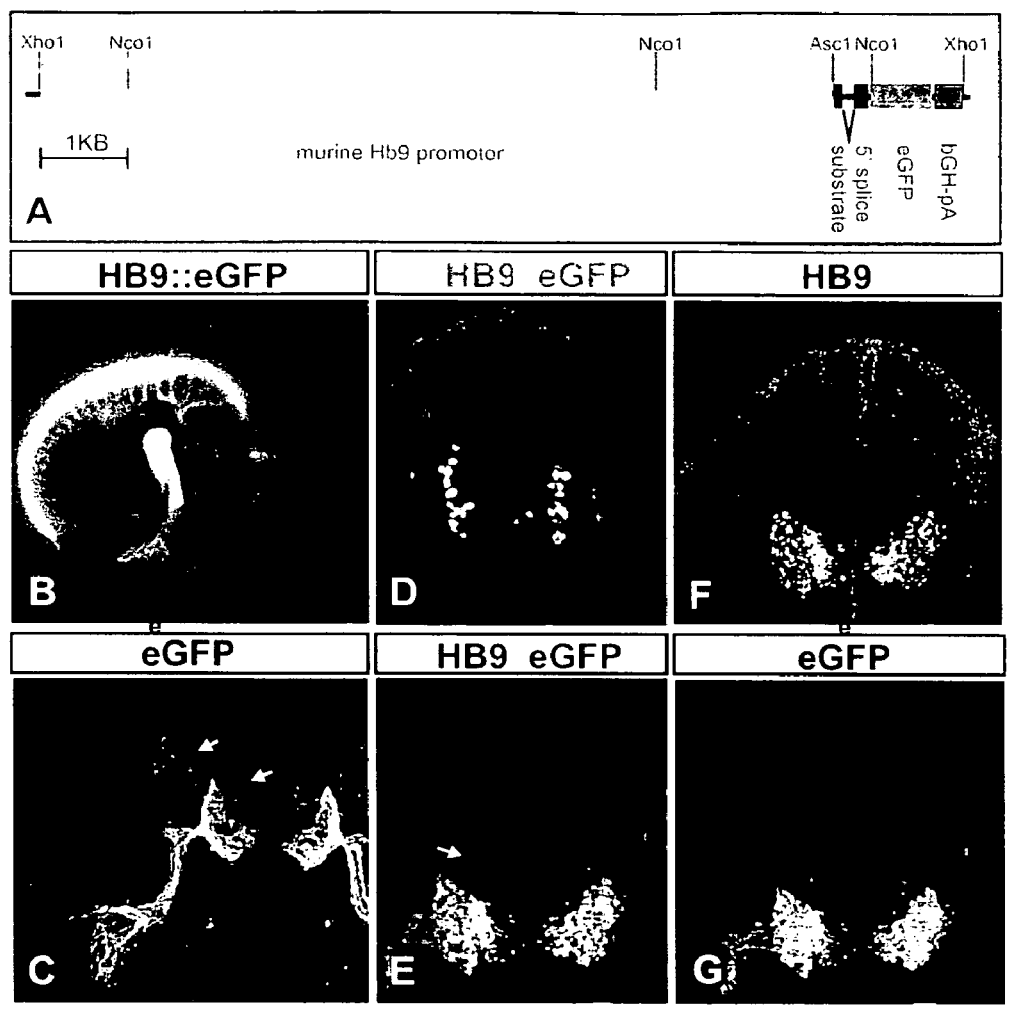
FIG. 4 illustrates eGFP-labeled motor neurons in the spinal cords of transgenic mouse embryos. (A) Construct for generation of mHB9-Gfp1b transgenic mouse line. (B) The pattern of enhanced green fluorescent protein (eGFP) expression in an E10.5 mHB9-Gfp1b mouse embryo. eGFP was highly expressed in the ventral spinal cord and in motor nerves extending from the spinal cord. (C) eGFP expression was detected in motor neuron cell bodies and dendrites in the ventral horn of E10.5 mHB9-Gfp1b embryos. eGFP expression was also detected in motor neuron axons exiting the spinal cord via the ventral root. In this line, at E10.5, but not later, very low expression was detected in dorsal root ganglion neurons (<20-fold that in motor neurons) and a subset of ventral interneurons (arrows in FIGS. 4C and 4E). (D) The pattern of HB9 and eGFP expression in forelimb-level spinal cord of mHB9-Gfp1b embryos at the time when first postmitotic motor neurons were generated (E9.5). eGFP expression mimicked that of HB9 in motor neuron cell bodies. (E-G) The pattern of HB9 and eGFP expression in thoracic spinal cord of E10.5 mHB9-Gfp1b embryos. eGFP was co-expressed with HB9 in motor neurons. Note that newly-postmitotic motor neurons located close to the ventricular zone expressed lower levels of eGFP than did more mature motor neurons in lateral regions of the spinal cord.

The heterogeneity of ventral neurons induced in EBs by RA and Hh signalling prompted the inventors to develop a method for identifying, purifying, and manipulating ES-cell-derived motor neurons. The inventors designed an ES-cell line capable of giving rise to motor neurons, identifiable by expression of enhanced green fluorescent protein (eGFP). A transgenic mouse line was generated in which an eGfp cDNA was expressed under the control of a 9-kb 5' region of the mouse HB9 gene that confers motor-neuron-specific trans-gene expression (FIG. 4A) (Arber et al., Requirement for the homeobox gene Hb9 in the consolidation of motor neuron identity. *Neuron,* 23:659-764, 1999). Transgenic founder mice were screened by comparing the patterns of HB9 and eGFP expression. One mouse line, mHB9-Gfp1b, was found to express high levels of eGFP in the cell bodies of spinal motor neurons in E9.5-P10 mice, in a pattern that paralleled that of endogenous HB9 (FIGS. 4B-4G). In addition, eGFP expression was detected at high levels in the axons and dendrites of motor neurons (FIG. 4C and data not shown). An ES-cell line (HBG3) was derived from mHB9-Gfp1b transgenic mice; these cells transmitted the eGfp gene through the germ-line, and directed expression of eGFP in a similar motor-neuron-selective pattern (data not shown).

Figure 5:
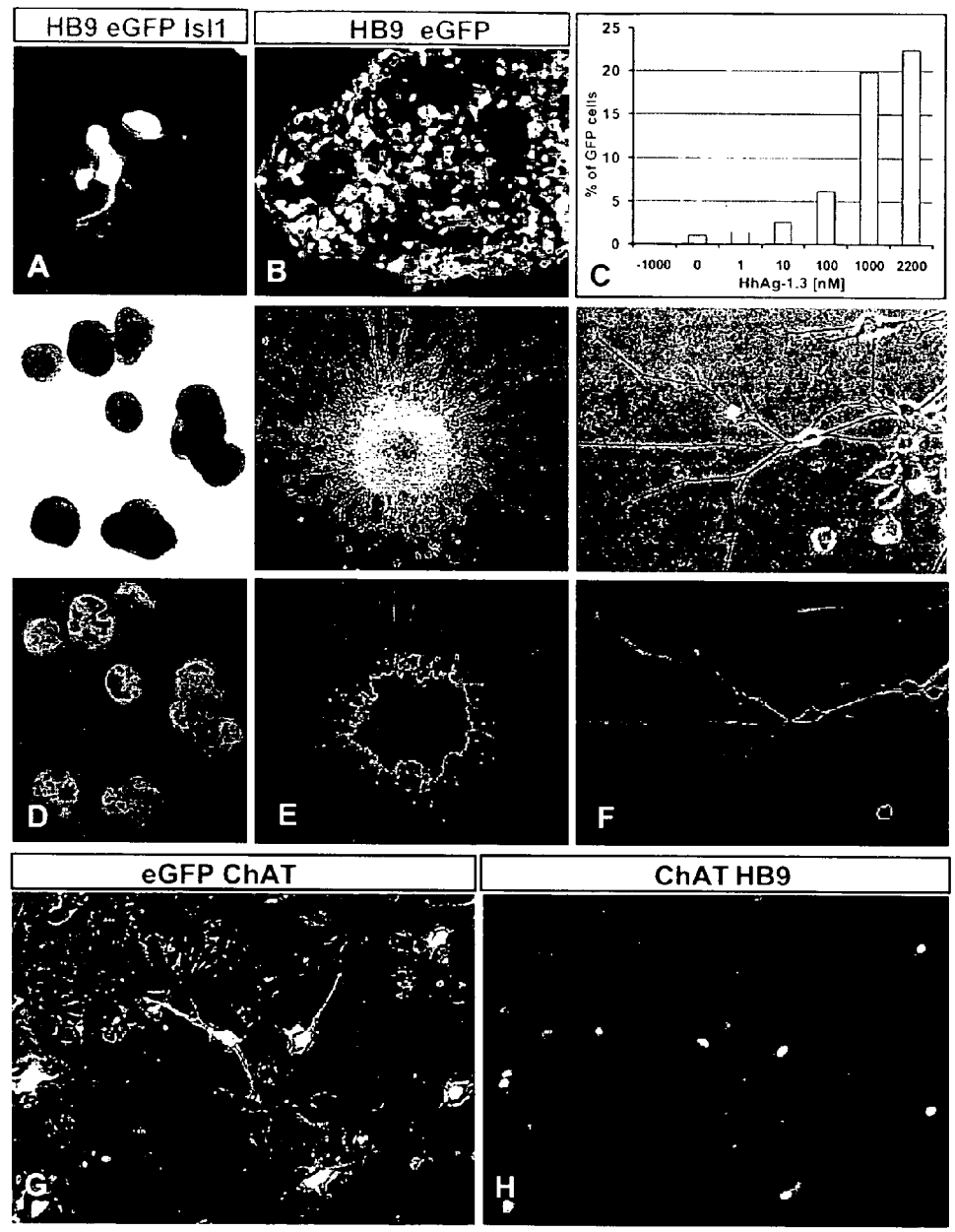
FIG. 5 depicts eGFP-labeled motor neurons derived in vitro from HBG ES cells. (A) HB9$^+$, Isl1$^+$ motor neurons in embryoid bodies (EBs) grown for 5 days, in the presence of RA, expressed eGFP in cell bodies and axons. (B) The number of eGFP$^+$ motor neurons increased upon exposure to Hh-Ag1.3 (1 μM). (C) Quantification of eGFP$^+$ motor neurons in EBs grown for 5 days in the presence of RA and increasing concentrations of Hh-Ag1.3 (0 to 2.2 μM). At 2.2 μM Hh-Ag1.3, 22.5% of cells in EBs expressed eGFP. At higher concentrations (10 μM), Hh-Ag1.3 became toxic for cells differentiating in EBs. The data point marked as "–1000" refers to a culture of EBs grown in the presence of 1 μM Hh-Ag1.3, but in the absence of RA. (D) Bright-field and fluorescence images showing eGFP expression in EBs grown for 5 days in the presence of RA and Hh-Ag1.3 (1 μM). (E) Phase and fluorescence images showing eGFP expression in embryoid bodies grown for 5 days in the presence of RA and Hh-Ag1.3 (1 μM), and plated on a matrigel substrate for a further 2 days. Many eGFP$^+$ motor axons emerged from these aggregates. (F) Phase and fluorescence images showing that eGFP labels neurites extending from motor neurons. (G, H) Co-expression of HB9, eGFP, and choline acetyltransferase (ChAT) in ES-cell-derived motor neurons grown in vitro for 7 days. ChAT$^+$ neurons that lacked HB9 and eGFP expression were probably interneurons.

The inventors found that HBG3 ES cells differentiated into motor neurons, under conditions of RA and Hh exposure, in a manner that resembled closely that of other mouse ES cells. EBs generated from HBG3 ES cells grown for 5 days in RA, but without Hh-Ag1.3, contained a few HB9+ motor neurons, and all of these co-expressed eGFP in their cell somata and neurites (FIG. 5A). The number of eGFP+/HB9+ motor neurons was increased upon exposure to Hh-Ag1.3, in a concentration-dependent manner (FIGS. 5B and 5C). Typically, eGFP+/HB9+ motor neurons constituted 20-30% of the total number of cells present in EBs exposed to RA and 1 µM Hh-Ag1.3 (1000; FIG. 5C). Exposure of EBs to Hh-Ag1.3 (1 µM) in the absence of RA failed to generate eGFP+/HB9+ motor neurons (~1000; FIG. 5C). Thus, HBG3 EB cells can also be induced to generate eGFP+/HB9+ motor neurons in an efficient manner, through activation of RA and Hh signalling pathways.

Figure 6:
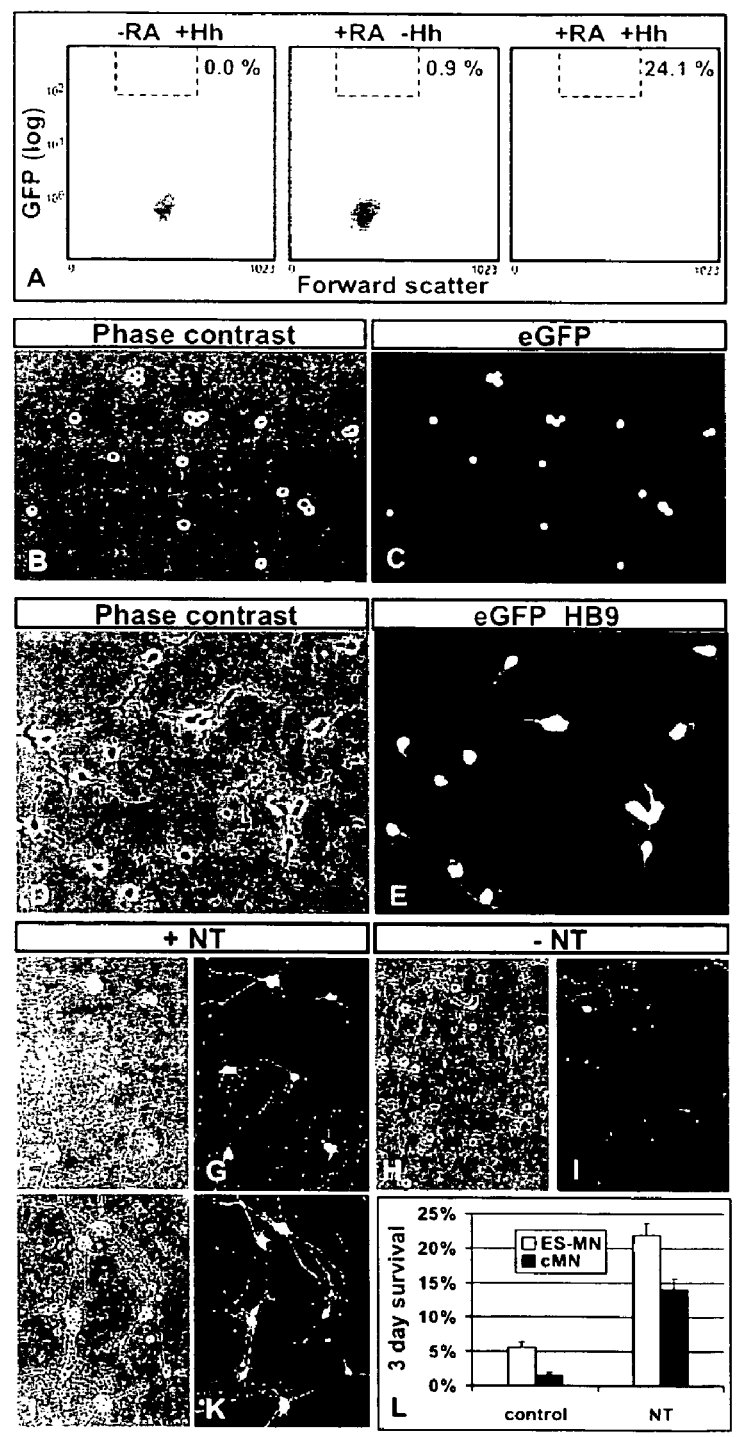
FIG. 6 illustrates isolation of eGFP$^+$ HBG3 ES-cell-derived motor neurons. (A) FACS analysis (cell-density plots) of HBG3 ES cells differentiated either in the presence of Hh-Ag1.3 (1 μM) alone, RA (2 μM) alone, or a combination of the two factors. The gate used for sorting motor neurons expressing high levels of eGFP is marked by a dashed rectangle. (B, C) Purified ES-cell-derived motor neurons, isolated by FACS sorting, expressed high levels of eGFP. (D, E) eGFP$^+$ neurons co-expressed HB9, and extended neurites when grown on a matrigel substrate for 24 h. (F, G) FACS-sorted ES-cell-derived motor neurons cultured in the presence of neurotrophic factors (NT3, BDNF, CNTF, and GDNF) survived for 3 days in vitro, and elaborated processes (F). Surviving motor neurons maintained expression of eGFP (G). (H, I) Most FACS-sorted ES-cell-derived motor neurons cultured in the absence of neurotrophic factors died within the first 3 days in vitro. (J, K) FACS-sorted primary rostral cervical motor neurons behaved in a manner similar to that of ES-cell-derived motor neurons. In the presence of neurotrophic factors, neurons survived and elaborated eGFP$^+$ processes. (L) Quantification of primary cervical motor neuron (cMN) and ES-cell-derived motor neuron (ES-MN) survival (percentage of plated cells) after 3 days in culture in the presence (NT) or absence (control) of neurotrophic factors. mean±s.e.m.; 6 wells scored

The inventors used eGFP expression to test whether HBG3 ES-cell-derived motor neurons undergo aspects of differentiation in vitro that are characteristic of embryo-derived motor neurons. RA- and Hh-exposed EBs (FIG. 5D) were dissociated into single cells or into small aggregates, and plated on a matrigel substrate in the presence of neurotrophic factors. ES-cell-derived motor neurons adhered, and extended long processes that could be visualized by eGFP expression (FIGS. 5R-5F). The morphological features of these ES-cell-derived motor neurons resembled those of eGFP-labeled motor neurons isolated from the embryonic spinal cord of mHB9-Gfp1b mice (FIGS. 6J and 6K and data not shown). Moreover, eGFP+/HB9+ motor neurons generated in vitro expressed choline acetyltransferase (FIGS. 5G and 5H), indicative of their cholinergic neurotransmitter status.

The inventors also examined the neurotrophic-factor-dependence of HBG3 ES-cell-derived motor neurons, in a direct comparison with primary embryonic motor neurons. The inventors dissociated RA- and Hh-exposed HBG3-derived EBs into a single cell suspension, and isolated cells that expressed high levels of eGFP using fluorescence-activated cell sorting (FACS) (FIG. 6A). In parallel, the inventors FACS-isolated primary embryonic motor neurons from rostral cervical spinal cord of E10.5 mHB9-Gfp1b embryos (data not shown). From either source, >98% of neurons that expressed high levels of eGFP also co-expressed HB9 (FIGS. 6B and 6C), and these neurons extended long processes (FIGS. 6D and 6E and data not shown). The survival of purified eGFP+/HB9+ motor neurons generated from HBG3 ES cells (FIGS. 6F-6I and 6L) or isolated from E10.5 mHB9-Gfp1b embryos (FIGS. 6J-6L) exhibited a similar dependence on neurotrophic factors. See, e.g., Bloch-Gallego et al., Survival in vitro of motoneurons identified or purified by novel antibody-based methods is selectively enhanced by muscle-derived factors. *Development,* 111:221-32, 1991; and Camu et al., Purification of embryonic rat motoneurons by panning on a monoclonal antibody to the low-affinity NGF receptor. *J. Neurosci. Methods,* 44:59-70, 1992.

ES-Cell-Derived eGFP+ Motor Neurons Differentiate in Embryonic Spinal Cord

The survival and differentiation of HBG3 ES-cell-derived motor neurons in vitro prompted the inventors to examine the behavior of these neurons when reintroduced into the spinal cord in vivo. EBs were isolated after 3-4 days of RA- and Hh-Ag1.3 exposure (when post-mitotic motor neurons first appear), dispersed into small aggregates, and implanted into the prospective rostral (or caudal) cervical, thoracic, or lumbar levels of the spinal cord of HH stages 15-17 chick embryos (FIG. 7A)—the stages at which differentiation of endogenous motor neurons begins (Hollyday et al., An autoradiographic study of the formation of the lateral motor column in the chick embryo. *Brain Res.,* 132:197-208, 1977). Operated embryos were permitted to develop for a further 3-7 days, to HH stages 27-36.

Figure 7:
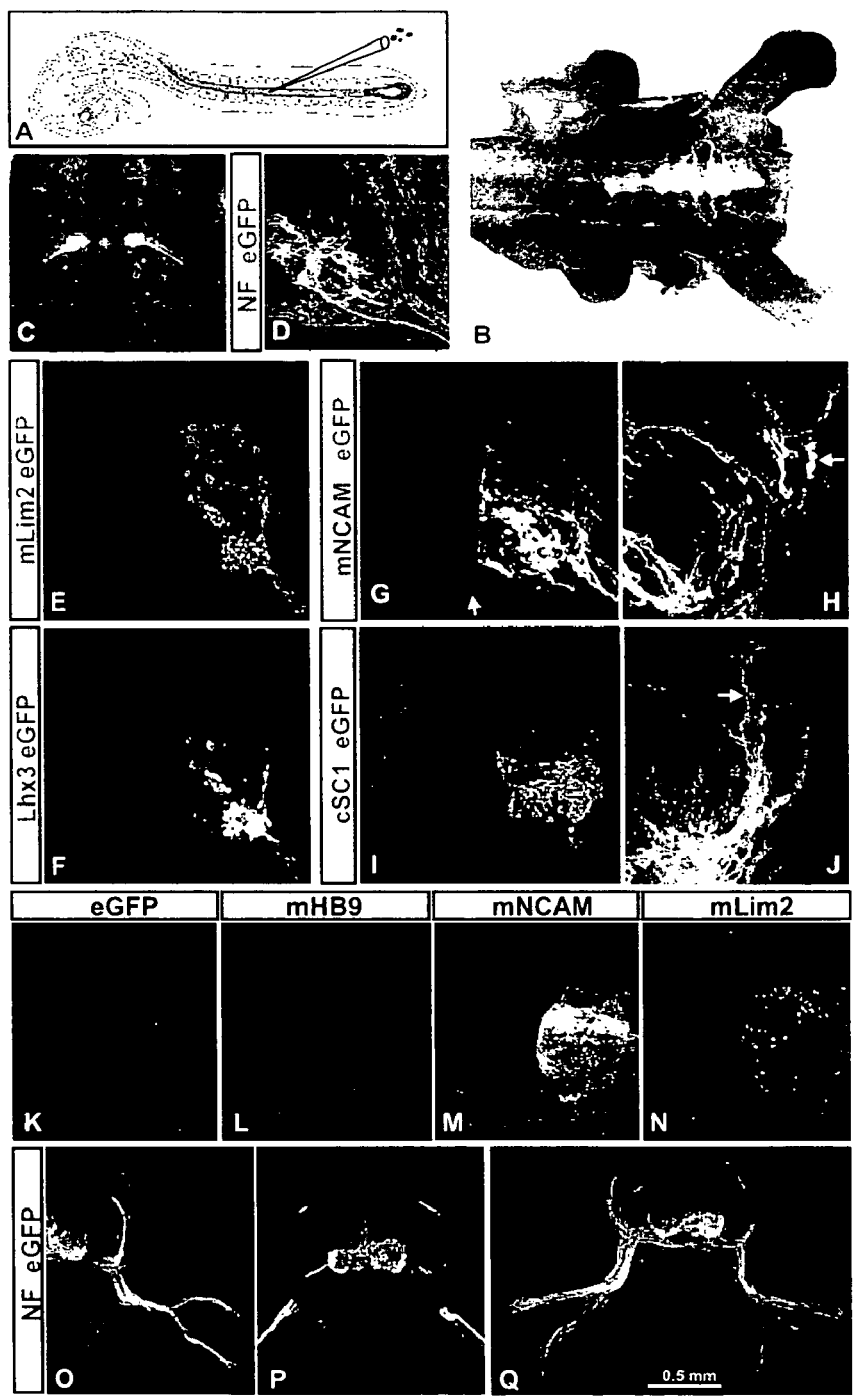
FIG. 7 depicts integration of transplanted ES-cell-derived motor neurons in vivo. (A) Schematic diagram showing implantation of HBG3 ES-cell-derived motor-neuron-enriched EBs into Hamburger-Hamilton (HH) stage 15 chick spinal cord. Spinal cord of the recipient chick embryo was suction-lesioned, and approximately ½-1 partially triturated EB was implanted into the ensuing space using a glass micropipette. (B) Bright-field/fluorescence image showing the position of eGFP$^+$ motor neurons (motor-neuron-enriched EBs were transplanted at HH stage 17) in the thoracic and lumbar spinal cord of a host chick embryo at HH stage 27 (ventral view). Note eGFP$^+$ axons emerging from the spinal cord. (C, D) Position of FACS-sorted motor neurons (transplanted into an HH stage 16 embryo) in thoracic spinal cord at stage 27. Transverse section revealed eGFP$^+$ motor neurons in the ventral spinal cord (D). (E-J) Transverse sections, through HH stage 27 chick spinal cord at rostral cervical level, after unilateral transplant of motor-neuron-enriched EBs at stage 15. Motor neurons were found primarily in the ventral horn of the spinal cord, segregated from transplanted interneurons labeled by mouse-specific Lim2 antibodies (E). Many ES-cell-derived motor neurons co-expressed eGFP and Lhx3 (F). Transplanted mouse ES-cell-derived motor neurons (G) and axons (arrow, H) were labeled by rodent-specific NCAM antibody, but they did not express the chick motor neuron marker protein, SC1 (I, J). Note that eGFP$^-$, NCAM$^+$ axons crossed the floor plate, but did not project out of the spinal cord (arrows, G, H). (K-N) Transverse sections of thoracic spinal cord at HH stage 27, which had received transplants of caudalized EBs (grown in the presence of RA (2 μM) and anti-Hh antibody (5E1, 30 μg/ml)), at HH stage 16. No mouse-derived motor neurons were detected, either by eGFP expression (K) or by mouse-specific HB9 antibodies (L). In contrast, many mouse-derived NCAM$^+$ (M) and Lim2$^+$ (N) neurons were present. (O-Q) Transverse sections, through HH stage 27 chick spinal cord at thoracic (O, P) or lumbar (Q) levels, which had received transplants of motor-neuron-enriched EBs at HH stage 16-17. eGFP$^+$ motor neuron cell bodies were concentrated in the ventral spinal cord. Some ectopic eGFP$^+$ motor neurons in grafted tissue remained trapped within the lumen of the spinal cord. eGFP$^+$ axons exited the spinal cord, primarily via the ventral root, and projected along all major nerve branches that supply axial (O-Q), body wall (O, P), and dorsal and ventral limb (O) muscle targets. The pathway of all peripheral axons was detected by neurofilament (NF) expression. Note the absence of eGFP$^+$ axons in the ventromedially-oriented nerves occupied by preganglionic motor axons.

Analysis of the spinal cord of operated embryos at HH stage 27 revealed the presence of many eGFP+/HB9+ motor neurons (FIGS. 7B-7J and 7O-7Q). Although the initial dorsoventral placement of EB grafts was not controlled, the inventors detected a striking segregation in the position of mouse motor neurons and interneurons in the chick spinal cord, when examined 3-7 days later (FIG. 7E). Almost invariably, eGFP+/HB9+ motor neurons were found in a ventrolateral position characteristic of that of endogenous motor neurons, whereas EB-derived Lim2+ interneurons (recognized by a rodent-specific antibody) were scattered along the dorsoventral axis of the spinal cord (FIG. 7E). The vast majority of eGFP+/HB9+ motor neurons co-expressed Lhx3 and lacked expression of Lim1, regardless of the segmental level of grafting (FIG. 7F and data not shown). Thus, the LIM HD profile of eGFP+/HB9+ ES-cell-derived motor neurons observed in vitro did not appear to be changed by in vivo grafting.

Since Olig2+ motor neuron progenitors were present in grafted EBs, it is possible that some or all of the eGFP+ motor neurons found in chick spinal cord derived from grafted progenitor cells that underwent terminal differentiated in situ. Accordingly, the inventors tested whether post-mitotic motor neurons that had been generated from HBG3 cells in vitro could also survive in the spinal cord in vivo. eGFP+/HB9+ ES-cell-derived motor neurons were isolated from dissociated EBs by FACS sorting, and then grafted into chick spinal cord. After 3 days, many eGFP+/HB9+ motor neurons were found in the ventral regions of the spinal cord (FIGS. 7C and 7D). Thus, post-mitotic ES-cell-derived motor neurons can also survive and differentiate in vivo.

Certain stem cell populations have been reported to undergo fusion with somatic cells (Terada et al., Bone marrow cells adopt the phenotype of other cells by spontaneous cell fusion. *Nature,* 416:542-45, 2002; Ying et al., Changing potency by spontaneous fusion. *Nature,* 416:545-48, 2002), prompting the inventors to test the possibility that HBG3-ES-cell-derived eGFP+/HB9+ motor neurons might have formed somatic hybrids with chick spinal cord neurons. The inventors found that eGFP+/HB9+ motor neuron cell bodies expressed neuronal surface proteins of mouse origin, such as NCAM (FIG. 7G)—which is recognized by a rodent-specific antibody —but did not express surface proteins of chick origin, such as SC1 (FIG. 7I)—which is recognized by a chick-specific antibody. Similarly, the axons of grafted motor neurons expressed mouse, but not chick, surface proteins (FIGS. 7H and 7J). These findings provide direct evidence against the occurrence of somatic cell fusion.

As an additional control, the inventors examined the fate of grafts of HBG3 EBs that had been neuralized and caudalized by in vitro exposure to RA, but prevented from ventralization by inclusion of anti-Hh antibody (5E1; 30 µg/ml). Many mouse NCAM+ cells and Lim2+ interneurons were found, but no eGFP+/HB9+ motor neurons were detected (FIGS. 7K-7N). Thus, cells present in RA-exposed EBs were not directed to a motor neuron fate in vivo upon exposure to signals provided by host chick tissues.

Additionally, the inventors examined whether the axons of HBG3 ES-cell-derived motor neurons extend out of the spinal cord. Many eGFP+ axons were detected in the ventral roots (FIGS. 7B, 7D, and 7O). Analysis of the pattern of peripheral projections of eGFP+ motor axons in HH stage 27 embryos revealed that HBG3 ES-cell-derived motor neurons, grafted at rostral cervical levels, projected to axial musculature (data not shown), that motor neurons grafted at thoracic levels projected towards both axial and body wall musculature (FIGS. 7O and 7P), and that motor neurons grafted at limb levels (caudal cervical or lumbar spinal cord) projected axons into both the dorsal and ventral halves of the limb (FIG. 7Q and data not shown). Thus, ES-cell-derived motor neurons are able to populate different segmental levels of the spinal cord, and to project along the major peripheral axonal pathways selected by host somatic motor neurons in vivo.

Figure 8:
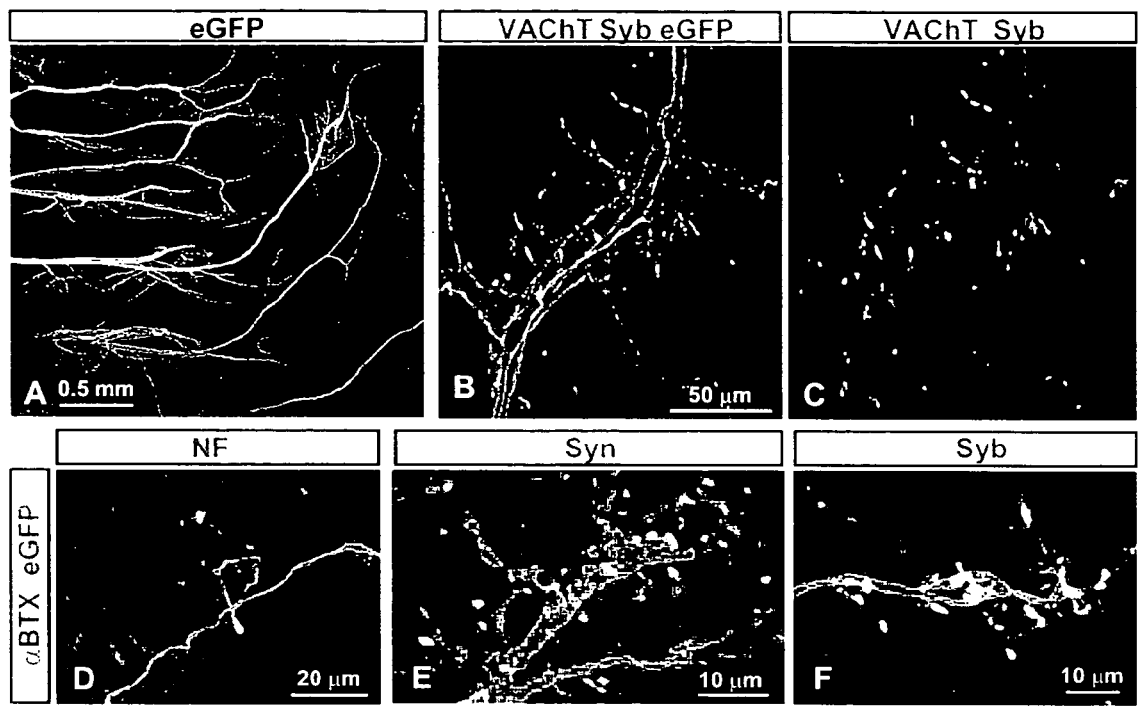
FIG. 8 illustrates synaptic differentiation of ES-cell-derived motor neurons in vivo. (A) Wholemount preparation of HH stage 35 chick embryonic rib cage. ES-cell-derived eGFP$^+$ axons innervated intercostal muscles. (B, C) Co-expression of synaptobrevin (Syb) and vesicular ACh transporter (VAChT) in the terminals of eGFP$^+$ axons at the site of nerve contact with muscle. The anti-Syb and VAChT antibodies recognized mouse proteins, but not chick proteins. (D) Expression of neurofilament (NF) and eGFP in fine nerve branches that supply the intercostal muscles. Note that some eGFP$^+$ axons lacked NF expression. The terminals of eGFP$^+$ axons coincided with ACh receptor clusters, as defined by α-bungarotoxin (αBTX) expression. (E) Coincidence of synaptotagmin expression and αBTX labeling at the terminals of eGFP$^+$ motor axons. (F) Coincidence of Syb expression and αBTX labeling at the terminals of eGFP$^+$ motor axons.
Figure 9:
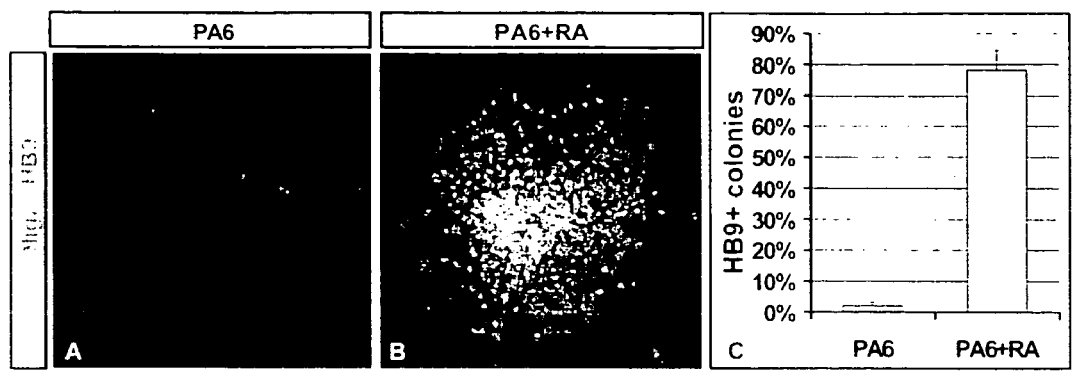
FIG. 9 shows that caudalized ES cells grown on PA6 cells differentiate into motor neurons. (A, B) ES cells grown on PA6 cells for 10 days did not differentiate into HB9$^+$ motor neurons (A). Addition of 2 μM RA to the culture medium on day 2 resulted in the generation of a large number of HB9$^+$ motor neurons, as well as Olig2-expressing progenitors (B). (C) Quantification of motor-neuron-containing ES cell colonies grown on PA6 cells for 10 days in the absence or presence of 2 μM RA. mean±s.d.; 3 wells

The inventors also found that the axons of eGFP+ motor neurons reach muscle targets. For example, extensive ingrowth and branching of eGFP+ motor axons was detected in the intercostal muscles at HH stages 30-35 (FIG. 8A). The inventors examined whether these eGFP+ motor axons exhibit aspects of terminal synaptic differentiation at sites of muscle contact. In particular, the inventors analyzed three markers of nerve terminal differentiation: synaptobrevin (Syb), which is recognized by a rodent-specific antibody); the vesicular ACh transporter (VAChT), which is recognized by a rodent-specific antibody); and synaptotagmin (Syn), which is recognized by an antibody that detects both rodent and chick protein). At sites of contact with muscles, eGFP+ motor axon branches displayed signs of presynaptic specialization, as revealed by focal expression of Syb, Syn, and VAChT (FIGS. 8B-8E).

The inventors next examined whether the presynaptic terminal specializations of eGFP+ motor axons were aligned with post-synaptic specialization of the muscle surface membrane, by analyzing the distribution of ACh receptors. Many of the terminal specializations of eGFP+ motor axons were aligned with focal clusters of ACh receptors on the muscle surface, as defined by rhodamine-α-bungarotoxin (Rh-α-BTX) labeling (FIG. 8F). Thus, the axons of ES-cell-derived motor neurons appeared to form synapses with target skeletal muscles in vivo.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for identifying a modulator of Hh-dependent motor neuron differentiation, comprising the steps of: (a) providing a first collection of embryonic stem cells and a second collection of embryonic stem cells; (b) contacting both collections of cells with an effective amount of retinoic acid to induce differentiation of the cells to form spinal progenitor cells; (c) activating a Hh signalling pathway in both collections of cells; (d) contacting the first collection of cells with a candidate modulator; and (e) determining if the candidate modulator in step (d) modulates motor neuron differentiation by comparing the motor neuron phenotypes of the cells in the first and second collections of cells produced by steps (b)-(d) where , if the motor neuron phenotypes of the cells in the first and second collections are different, it indicates that the candidate modulator is a modulator of Hh-dependent motor neuron differentiation.

2. The method of claim 1, where the motor neuron phenotype comprises expression of the motor neuron associated protein HB9.

3. The method of claim 1, where the motor neuron phenotype comprises expression of Green Fluorescent Protein, where expression of Green Fluorescent Protein is controlled by the HB9 promoter.

4. The method of claim 1, where the modulator has an agonistic effect on motor neuron differentiation whereby the rate of motor neuron differentiation in the first collection of cells, contacted with the modulator, is increased relative to the rate of motor neuron differentiation in the second collection of cells, as measured by the presence of one or more feature characteristic of a motor neuron phenotype.

5. A method for identifying a modulator of Hh-dependent motor neuron differentiation, comprising the steps of: (a) contacting a collection of embryonic stem cells with an effective amount of retinoic acid to induce differentiation of the cells to form spinal progenitor cells; (b) activating a Hh signalling pathway in the collection of cells; (c) contacting the collection of cells with a candidate modulator; and (d) determining if the candidate modulator increases the rate of motor neuron differentiation as measured by the presence of one or more feature characteristic of a motor neuron phenotype, wherein an increase in the rate of motor neuron differentiation indicates that the candidate modulator is an agonist of motor neuron differentiation.

6. The method of claim 5, where the phenotype comprises expression of the motor neuron associated protein HB9.

7. The method of claim 5, where the phenotype comprises expression of Green Fluorescent Protein, where expression of Green Fluorescent Protein is controlled by the HB9 promoter.

* * * * *

SEQUENCE LISTING

```
<160> NUMBER OF SEQ ID NOS: 1

<210> SEQ ID NO 1
<211> LENGTH: 18
<212> TYPE: PRT
<213> ORGANISM: artificial sequence
<220> FEATURE:
<223> OTHER INFORMATION: used to immunize rabbits, so as to produce
      anti-Sox1 antibody

<400> SEQUENCE: 1

Cys Gln Ser Arg Leu His Ser Leu Pro Gln His Tyr Gln Gly Ala Gly
1               5                   10                  15

Ala Gly
```